US010316329B2

(12) United States Patent
Baum et al.

(10) Patent No.: US 10,316,329 B2
(45) Date of Patent: Jun. 11, 2019

(54) PROTEINS TOXIC OR INHIBITORY TO LEPIDOPTERAN INSECTS

(71) Applicant: Monsanto Technology LLC, St. Louis, MO (US)

(72) Inventors: James Arthur Baum, Webster Groves, MO (US); David Joseph Bowen, Glencoe, MO (US); Catherine Alice Chay, Ballwin, MO (US); Artem G Evdokimov, Foristell, MO (US); Stanislaw Flasinski, Chesterfield, MO (US); Uma Rao Kesanapalli, Chesterfield, MO (US); Jeffrey R Nageotte, Billerica, MA (US); James Kevin Roberts, Chesterfield, MO (US); Brian Edward Weiner, St. Louis, MO (US)

(73) Assignee: Monsanto Technology LLC, St. Louis, MO (US)

(*) Notice: Subject to any disclaimer, the term of this patent is extended or adjusted under 35 U.S.C. 154(b) by 410 days.

(21) Appl. No.: 14/884,456

(22) Filed: Oct. 15, 2015

(65) Prior Publication Data

US 2016/0108427 A1  Apr. 21, 2016

Related U.S. Application Data

(60) Provisional application No. 62/064,998, filed on Oct. 16, 2014.

(51) Int. Cl.
| *C12N 15/82* | (2006.01) |
| *C07K 14/325* | (2006.01) |
| *A01N 63/02* | (2006.01) |
| *C07K 14/32* | (2006.01) |

(52) U.S. Cl.
CPC ......... *C12N 15/8286* (2013.01); *A01N 63/02* (2013.01); *C07K 14/32* (2013.01); *C07K 14/325* (2013.01); *Y02A 40/162* (2018.01)

(58) Field of Classification Search
None
See application file for complete search history.

(56) References Cited

U.S. PATENT DOCUMENTS

| 5,188,642 A | 2/1993 | Shah et al. |
| 5,312,910 A | 5/1994 | Kishore et al. |
| 5,500,365 A | 3/1996 | Fischhoff et al. |
| 5,510,471 A | 4/1996 | Lebrun et al. |
| 5,627,061 A | 5/1997 | Bany et al. |
| 5,633,435 A | 5/1997 | Bany et al. |
| 5,633,448 A | 5/1997 | Lebrun et al. |
| 5,728,925 A | 3/1998 | Herrera-Estrella et al. |
| 5,880,275 A | 3/1999 | Fischhoff et al. |
| 6,033,874 A | 3/2000 | Baum et al. |
| 6,107,279 A | 8/2000 | Estruch et al. |
| 6,501,009 B1 | 12/2002 | Romano et al. |
| 6,551,962 B1 | 4/2003 | Pershing et al. |
| 6,713,063 B1 | 3/2004 | Malvar et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,193,133 B2 | 3/2007 | Lassner et al. |
| 7,510,878 B2 | 3/2009 | Abad et al. |
| 7,772,465 B2 | 8/2010 | Abad et al. |
| 7,812,129 B1 | 10/2010 | Abad et al. |
| 7,927,598 B2 | 4/2011 | Malvar et al. |
| 8,609,936 B2 | 12/2013 | Baum et al. |
| 2006/0021087 A1 | 1/2006 | Baum et al. |
| 2006/0112447 A1 | 5/2006 | Bogdanova et al. |
| 2008/0172762 A1 | 7/2008 | Cerf et al. |
| 2009/0313721 A1 | 12/2009 | Abad et al. |
| 2010/0004176 A1 | 1/2010 | Sampson et al. |
| 2010/0017914 A1 | 1/2010 | Hart et al. |
| 2010/0077507 A1 | 3/2010 | Abad et al. |
| 2010/0077508 A1 | 3/2010 | Abad et al. |
| 2010/0137216 A1 | 6/2010 | Carozzi et al. |
| 2010/0160231 A1 | 6/2010 | Sampson et al. |
| 2010/0192256 A1 | 7/2010 | Abad et al. |
| 2010/0197592 A1 | 8/2010 | Heinrichs et al. |
| 2010/0269221 A1 | 10/2010 | Abad et al. |
| 2010/0317569 A1 | 12/2010 | Lira et al. |
| 2010/0319093 A1 | 12/2010 | Lira et al. |
| 2011/0030096 A1 | 2/2011 | Sampson et al. |
| 2011/0055968 A1 | 3/2011 | Cerf et al. |

(Continued)

FOREIGN PATENT DOCUMENTS

| EP | 0189707 A2 | 8/1986 |
| EP | 0218571 A2 | 4/1987 |

(Continued)

OTHER PUBLICATIONS

Rang et al, Appl. Environ. Microbiol. (2005) 71:6276-6281.*
Banyuls et al, Nature Scientific Reports (2018) 8:7539; p. 1-14.*
Della-Cioppa et al., "Translocation of the precursor of 5-enolpyruvylshikimate-3-phosphate synthase into chloroplasts of higher plants in vitro," *Proc. Natl. Acad. Sci. USA*, 83:6873-6877, (1986).
Estruch et al., "Vip3A, a novel *Bacillus thuringiensis* vegetative insecticidal protein with a wide spectrum of activities against lepidopteran insects," *Proc. Natl. Acad. Sci. USA*, 93:5389-5394 (1996).

(Continued)

*Primary Examiner* — Mykola V. Kovalenko
(74) *Attorney, Agent, or Firm* — Timothy K. Ball; Carine M. Doyle; Arnold & Porter Kaye Scholer LLP

(57) ABSTRACT

Nucleotide sequences are disclosed encoding novel, insecticidal TIC2160 and TIC3244 proteins, and variants thereof, and related proteins exhibiting Lepidopteran inhibitory activity, as well as fragments thereof. Particular embodiments provide compositions and transformed plants, plant parts, and seeds containing a polynucleotide construct encoding one or more of the toxin proteins within the TIC2160-related protein toxin class.

19 Claims, No Drawings

Specification includes a Sequence Listing.

(56) References Cited

U.S. PATENT DOCUMENTS

| | | |
|---|---|---|
| 2011/0112013 A1 | 5/2011 | Abad et al. |
| 2011/0154536 A1 | 6/2011 | Abad et al. |
| 2012/0047606 A1 | 2/2012 | Abad et al. |
| 2012/0117690 A1 | 5/2012 | Cerf et al. |
| 2012/0167259 A1 | 6/2012 | Liu et al. |
| 2012/0192310 A1 | 7/2012 | Abad et al. |
| 2012/0210462 A1 | 8/2012 | Bermudez et al. |
| 2012/0233726 A1 | 9/2012 | Abad et al. |
| 2013/0055469 A1 | 2/2013 | Sampson et al. |
| 2013/0097735 A1 | 4/2013 | Bowen et al. |
| 2013/0104259 A1 | 4/2013 | Sampson et al. |
| 2013/0117884 A1 | 5/2013 | Hargiss et al. |
| 2013/0167264 A1 | 6/2013 | Sampson et al. |
| 2013/0219570 A1 | 8/2013 | Lira et al. |
| 2013/0269060 A1 | 10/2013 | Baum et al. |
| 2013/0303440 A1 | 11/2013 | Sampson et al. |
| 2013/0310543 A1 | 11/2013 | Sampson et al. |
| 2014/0007292 A1 | 1/2014 | Cerf et al. |
| 2014/0033361 A1 | 1/2014 | Altier et al. |
| 2014/0033363 A1 | 1/2014 | Sampson et al. |
| 2014/0196175 A1 | 7/2014 | Sampson et al. |
| 2014/0223598 A1 | 8/2014 | Sampson et al. |
| 2014/0223599 A1 | 8/2014 | Sampson et al. |
| 2014/0245491 A1 | 8/2014 | Sampson et al. |
| 2014/0298538 A1 | 10/2014 | Heinrichs et al. |
| 2014/0366227 A1 | 12/2014 | Gatehouse et al. |
| 2014/0373195 A1 | 12/2014 | Sampson et al. |
| 2015/0264940 A1 | 9/2015 | Tan et al. |
| 2015/0366211 A1 | 12/2015 | Armstrong et al. |

FOREIGN PATENT DOCUMENTS

| | | | |
|---|---|---|---|
| EP | 0508909 A1 | 10/1992 | |
| EP | 0924299 A1 | 6/1999 | |
| WO | WO 2012/139004 A2 | 11/2012 | |
| WO | WO 2013/134523 A1 | 9/2013 | |
| WO | WO-2013134523 A1 * | 9/2013 | ......... C12N 15/8286 |
| WO | WO 2013/134523 A1 | 12/2013 | |
| WO | WO 2014/008054 A2 | 1/2014 | |

OTHER PUBLICATIONS

GenBank Accession No. AAC37037.1, "insecticidal protein [*Bacillus thuringiensis*]," (1996).

GenBank Accession No. AAV70653.1, "Vip3Ba1 [*Bacillus thuringiensis*]," (2005).

James, "Global Status of Commercialized Biotech/GM Crops: 2012," *ISAAA*, Brief No. 44 (2012).

Klee et al., "Cloning of an *Arabidopsis thaliana* gene encoding 5-enolpyruvylshikimate-3-phosphate synthase: sequence analysis and manipulation to obtain glyphosate-tolerant plants," *Mol Gen Genet*, 210:437-442 (1987).

EBI Accession No. GSP:BAT55925, "*Bacillus thuringiensis* toxin Axmi335 protein, SEQ:2.", Nov. 7, 2013.

International Search Report and Written Opinion dated Feb. 1, 2016, in International Application No. PCT/US2015/055802.

* cited by examiner

SEQUENCE LISTING

```
<160> NUMBER OF SEQ ID NOS: 44

<210> SEQ ID NO 1
<211> LENGTH: 2397
<212> TYPE: DNA
<213> ORGANISM: Bacillus thuringiensis
<220> FEATURE:
<221> NAME/KEY: misc_feature
<222> LOCATION: (1)..(2397)
<223> OTHER INFORMATION: Recombinant nucleotide sequence encoding the
      protein toxin TIC2160 derived from DNA isolated from the Bacillus
      thuringiensis strain EG8781.

<400> SEQUENCE: 1
atgcaaagga tgataattgt ggataataat aaattaaatg taagagcttt accaagcttt      60
```

```
attgattatt ttaacggtat ttatggattt gccactggta tcaaagatat tatgggaatg      120 attttaaaa cagatacagg tggtagtaat ttaacattag atgagatttt aaagaatcaa       180
aatttactaa atgatatctc aggtaagctc gatggaatta atggagattt aggggatctt      240
attgcacaag ggaacttgaa ttcagaatta gctaaggaat tgctaaaaat ctctaatgag      300
cagaatcaaa tgttaaatca tgttaatgct caacttaatg caatcaattc aacacttaat      360
atatatcttc caaaaattac atctatgtta aatgaggtga tgaagcaaaa ccatgtttta      420
agtctacaaa tagaatttct tagtaagcaa ttgcaggaaa tttcagataa acttgatatt      480
atcaacttaa acgtattgat taactctaca ttaacagaga ttactcctgc ttatcaacgt      540
attaaatatg taaacgaaaa atttgatgaa ttgacttcta ctgtagagaa aaatccaaaa      600
tcatatcaag ataacgttac taagaagtt attgaaaact taaatgagct aactgagttg       660
gcgaaaagtg ttaccaaaaa tgatatggat agttttgaat tttatcttca aactttccat      720
gatgtaatga ctggaaataa tttattcggc cgctcagcat taaaaactgc ttcagaatta      780
attacaaaag aaaatgtcac gacaagggga agtgagatag aaaagtttta aatttctta      840 attgttttaa cttctttaca agcaaaagct tttctcactt taactgcatg tcgaaagtta      900
ttaggtttaa cagatatcga ttatactcaa attatgaatc atcatataga tggtcaaaaa      960
agagaatttc gtattaatat tcttccaaca ctttctaata attttctaa tcctagttat       1020 tcaaaaaata gaggaagtga tatcgatgat ccaattgttg tgttagaagc agcacctgga     1080
tatgccttaa taggatttga aattctaaac gatccacttc caattttaaa aggatatcag      1140
gctaggttaa aaccaaatta tcaagttgac agggagtcga tgtcagaaac gatttatggg      1200
gacattcata aattatttg cccaaaacag ctggagcaaa aatattatat taaagatatt       1260
gaatttcctg agggctatgt aattactaaa atcgtttttg aaaaaaggct aaatcaattg      1320
gggtatgagg taacagcaaa tttttatgac ccgtctacag gaagtatcga tttaaataag     1380
gttaaagtag aatcttggaa ggaaaagtct tgcgaggagg attcctgcga agatgagtat      1440
agtattataa aggccgaaac ggatggcatt tatatgccat taggcgtagt aagtgagact      1500 ttttaaccc ctatttatgg ttttggatta acagttgacg aaaaaaatca aaaataact       1560 ttaacaggta atcctatttt acgtgaatcc ttactagaaa cagacttact taacaatgaa      1620
acatatttaa ttgcttcacc agacggttat attagtagta ttgtagaaaa ctggaatata      1680
acatcagata atactgggtc ttggagagca ataataata atgcatttgt cgataaggca      1740
gatactataa aaggatcaag ttctctgtat actcataaag atggggaatt ctcgcaattt      1800
attggaaata agctaaaacc taaaactaat tatgttattc aatatgttat aaaaggaaga     1860
cctgctattt atttaaaaaa taataaagat acttttattg aggataccaa aaataactt       1920 agcgattttc agactgtaac taaaaaattc aattcaggag taaatccttc ggaaatttat      1980 ttcctttta aaaatcaaag tgaatacgaa gcctggggaa ataactttat tattttagaa       2040
attaaatcgc ttgaattctt gccacaaatg ctgaagcctg aggattggat accatcagga      2100
aatgtgcaaa tgaaagatgg aggacgccta gagattttgg gagatggtta ttttaaacaa      2160
ttcattaaat tggaaaatga ttcaacctat catctaagat tatctgttaa gggaacaggt      2220
agggtatcta taattgatga atctaaatat ttacttttg taaatgttaa ggatgaagat        2280
cttactagag ttattaaaaa tacctcttca aagggtgagt gttttatagc tcttgagggt      2340
acttatgtag aaaaattcaag tactattttc tctaatgtat ctattgttaa agagtag       2397
```

<210> SEQ ID NO 2
<211> LENGTH: 798
<212> TYPE: PRT
<213> ORGANISM: Bacillus thuringiensis
<220> FEATURE:
<221> NAME/KEY: MISC_FEATURE
<222> LOCATION: (1)..(798)
<223> OTHER INFORMATION: Amino acid sequence of TIC2160 derived from
    Bacillus thuringiensis strain EG8781.

<400> SEQUENCE: 2

```
Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
            20                  25                  30

Gly Ile Lys Asp Ile Met Gly Met Ile Phe Lys Thr Asp Thr Gly Gly
        35                  40                  45

Ser Asn Leu Thr Leu Asp Glu Ile Leu Lys Asn Gln Asn Leu Leu Asn
    50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
    130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
                165                 170                 175

Ala Tyr Gln Arg Ile Lys Tyr Val Asn Glu Lys Phe Asp Glu Leu Thr
            180                 185                 190

Ser Thr Val Glu Lys Asn Pro Lys Ser Tyr Gln Asp Asn Val Thr Lys
        195                 200                 205

Glu Val Ile Glu Asn Leu Asn Glu Leu Thr Glu Leu Ala Lys Ser Val
    210                 215                 220

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
                245                 250                 255

Ala Ser Glu Leu Ile Thr Lys Glu Asn Val Thr Thr Arg Gly Ser Glu
            260                 265                 270

Ile Gly Lys Val Tyr Asn Phe Leu Ile Val Leu Thr Ser Leu Gln Ala
        275                 280                 285

Lys Ala Phe Leu Thr Leu Thr Ala Cys Arg Lys Leu Leu Gly Leu Thr
    290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
                325                 330                 335

Asn Pro Ser Tyr Ser Lys Asn Arg Gly Ser Asp Ile Asp Pro Ile
            340                 345                 350
```

```
Val Val Leu Glu Ala Ala Pro Gly Tyr Ala Leu Ile Gly Phe Glu Ile
                355                 360                 365

Leu Asn Asp Pro Leu Pro Ile Leu Lys Gly Tyr Gln Ala Arg Leu Lys
        370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Lys Gln Leu Glu Gln Lys Tyr Tyr
                405                 410                 415

Ile Lys Asp Ile Glu Phe Pro Glu Gly Tyr Val Ile Thr Lys Ile Val
                420                 425                 430

Phe Glu Lys Arg Leu Asn Gln Leu Gly Tyr Glu Val Thr Ala Asn Phe
            435                 440                 445

Tyr Asp Pro Ser Thr Gly Ser Ile Asp Leu Asn Lys Val Lys Val Glu
        450                 455                 460

Ser Trp Lys Glu Lys Ser Cys Glu Glu Asp Ser Cys Glu Asp Glu Tyr
465                 470                 475                 480

Ser Ile Ile Lys Ala Glu Thr Asp Gly Ile Tyr Met Pro Leu Gly Val
                485                 490                 495

Val Ser Glu Thr Phe Leu Thr Pro Ile Tyr Gly Phe Gly Leu Thr Val
            500                 505                 510

Asp Glu Lys Asn Gln Lys Ile Thr Leu Thr Gly Lys Ser Tyr Leu Arg
        515                 520                 525

Glu Ser Leu Leu Glu Thr Asp Leu Leu Asn Asn Glu Thr Tyr Leu Ile
        530                 535                 540

Ala Ser Pro Asp Gly Tyr Ile Ser Ser Ile Val Glu Asn Trp Asn Ile
545                 550                 555                 560

Thr Ser Asp Asn Thr Gly Ser Trp Arg Ala Asn Asn Asn Asn Ala Phe
                565                 570                 575

Val Asp Lys Ala Asp Thr Ile Lys Gly Ser Ser Ser Leu Tyr Thr His
            580                 585                 590

Lys Asp Gly Glu Phe Ser Gln Phe Ile Gly Asn Lys Leu Lys Pro Lys
        595                 600                 605

Thr Asn Tyr Val Ile Gln Tyr Val Ile Lys Gly Arg Pro Ala Ile Tyr
        610                 615                 620

Leu Lys Asn Asn Lys Asp Thr Leu Phe Glu Asp Thr Lys Asn Asn Phe
625                 630                 635                 640

Ser Asp Phe Gln Thr Val Thr Lys Lys Phe Asn Ser Gly Val Asn Pro
                645                 650                 655

Ser Glu Ile Tyr Phe Leu Phe Lys Asn Gln Ser Glu Tyr Glu Ala Trp
                660                 665                 670

Gly Asn Asn Phe Ile Ile Leu Glu Ile Lys Ser Leu Glu Phe Leu Pro
            675                 680                 685

Gln Met Leu Lys Pro Glu Asp Trp Ile Pro Ser Gly Asn Val Gln Met
        690                 695                 700

Lys Asp Gly Gly Arg Leu Glu Ile Leu Gly Asp Gly Tyr Phe Lys Gln
705                 710                 715                 720

Phe Ile Lys Leu Glu Asn Asp Ser Thr Tyr His Leu Arg Leu Ser Val
                725                 730                 735

Lys Gly Thr Gly Arg Val Ser Ile Ile Asp Glu Ser Lys Tyr Leu Leu
            740                 745                 750

Phe Val Asn Val Lys Asp Glu Asp Leu Thr Arg Val Ile Lys Asn Thr
        755                 760                 765

Ser Ser Lys Gly Glu Cys Phe Ile Ala Leu Glu Gly Thr Tyr Val Glu
```

```
    770                 775                 780

Asn Ser Ser Thr Ile Phe Ser Asn Val Ser Ile Val Lys Glu
785                 790                 795

<210> SEQ ID NO 3
<211> LENGTH: 2397
<212> TYPE: DNA
<213> ORGANISM: Bacillus thuringiensis
<220> FEATURE:
<221> NAME/KEY: misc_feature
<222> LOCATION: (1)..(2397)
<223> OTHER INFORMATION: Coding sequence encoding
<220> FEATURE:
<221> NAME/KEY: misc_feature
<222> LOCATION: (1)..(2397)
<223> OTHER INFORMATION: Recombinant nucleotide sequence encoding the
      protein toxin TIC3244 derived from DNA isolated from the Bacillus
      thuringiensis strain EG8639.

<400> SEQUENCE: 3
atgcaaagga tgataattgt ggataataat aaattaaatg taagagcttt accaagcttt     60
attgattatt ttaacggtat ttatggattt gccactggta tcaaagatat tatgggaatg    120
atttttaaaa cagatacagg tggtagtaat ttaacattag atgagatttt aaagaatcaa    180
aatttactaa atgatatctc aggtaagctc gatggaatta atggagattt aggggatctt    240
attgcacaag ggaacttgaa ttcagaatta gctaaggaat tgctaaaaat ctctaatgag    300
cagaatcaaa tgttaaatca tgttaatgct caacttaatg caatcaattc aacacttaat    360
atatatcttc caaaaattac atctatgtta aatgaggtga tgaagcaaaa ccatgtttta    420
agtctacaaa tagaatttct tagtaagcaa ttgcaggaaa tttcagataa acttgatatt    480
atcaacttaa acgtattgat taactctaca ttaacagaga ttactcctgc ttatcaacgt    540
attaaatatg taaacgaaaa atttgatgaa ttgacttcta ctgtagagaa aaatccaaaa    600
tcatatcaag ataacgttac taaagaagtt attgaaaact taaatgagct aactgagttg    660
gcgaaaagtg ttaccaaaaa tgatatggat agttttgaat tttatcttca aactttccat    720
gatgtaatga ctggaaataa tttattcggc cgctcagcat taaaaactgc ttcagaatta    780
attacaaaag aaaatgtcac gacaagggga agtgagatag gaaaagttta taatttctta    840
attgttttaa cttctttaca agcaaaagct tttctcactt taactgcatg tcgaaagtta    900
ttaggtttaa cagatatcga ttatactcaa attatgaatc atcatataga tggtcaaaaa    960
agagaatttc gtattaatat tcttccaaca ctttctaata atttttctaa tcctagttat   1020
tcaaaaaata gaggaagtga tatcgatgat ccaattgttg tgttagaagc agcacctgga   1080
tatgccttaa taggatttga aattctaaac gatccacttc caattttaaa aggatatcag   1140
gctaggttaa aaccaaatta tcaagttgac agggagtcga tgtcagaaac gatttatggg   1200
gacattcata aattattttg cccaaaacag ctggagcaaa aatattatat taaagatatt   1260
gaatttcctg agggctatgt aattactaaa atcgtttttg aaaaaaggct aaatcaattg   1320
gggtatgagg taacagcaaa tttttatgac ccgtctacag gaagtatcga tttaaataag   1380
gttaaagtag aatcttggaa ggaaaagtct tgcgaggagg attcctgcga agatgagtat   1440
agtattataa aggccgaaac ggatggcatt tatatgccat taggcgtagt aagtgagact   1500
tttttaaccc ctatttatgg ttttggatta acagttgacg aaaaaaatca aaaaataact   1560
ttaacaggta aatcctattt acgtgaatcc ttactagaaa cagacttact taacaatgaa   1620
acatatttaa ttgcttcacc agacggttat attagtagta ttgtagaaaa ctggaatata   1680
```

-continued

```
acatcagata atactgggtc ttggagagca ataataata atgcatttgt cgataaggca    1740
gatactataa aaggatcaag ttctctgtat actcataaag atggggaatt ctcgcaattt    1800
attggaaata agctaaaacc taaaactaat tatgttattc aatatgttat aaaaggaaga    1860
cctgctattt atttaaaaaa taataaagat actttatttg aggataccaa aaataacttt    1920
agcgattttc agactgtaac taaaaaattc aattcaggag taaatccttc ggaaatttat    1980
ttcctttttta aaaatcaaag tgaatacgaa gcctggggaa ataacttat tattttagaa    2040
attaaatcgc ttgaattctt gccacaaatg ctgaagcctg aggattggat accatcagga    2100
aatgtgcaaa tgaaagatgg aggacgccta gagattttgg gagatggtta ttttaaacaa    2160
ttcattaaat tggaaaatga ttcaacctat catctaagat tatctgttaa gggaacaggt    2220
agggtatcta taattgatga atctaaatat ttccttttg taaatgttaa ggatgaagat    2280
cttactagag ttattaaaaa tacctcttca aagggtgagt gttttatagc tcttgagggt    2340
acttatgtag aaaattcaag tactattttc tctaatgtat ctattgttaa agagtag      2397
```

<210> SEQ ID NO 4
<211> LENGTH: 798
<212> TYPE: PRT
<213> ORGANISM: Bacillus thuringiensis
<220> FEATURE:
<221> NAME/KEY: MISC_FEATURE
<222> LOCATION: (1)..(798)
<223> OTHER INFORMATION: Amino acid sequence of TIC3244 derived from the
      Bacillus thuringiensis strain EG8639.

<400> SEQUENCE: 4

```
Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
            20                  25                  30

Gly Ile Lys Asp Ile Met Gly Met Ile Phe Lys Thr Asp Thr Gly Gly
        35                  40                  45

Ser Asn Leu Thr Leu Asp Glu Ile Leu Lys Asn Gln Asn Leu Leu Asn
    50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
    130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
                165                 170                 175

Ala Tyr Gln Arg Ile Lys Tyr Val Asn Glu Lys Phe Asp Glu Leu Thr
            180                 185                 190

Ser Thr Val Glu Lys Asn Pro Lys Ser Tyr Gln Asp Asn Val Thr Lys
        195                 200                 205

Glu Val Ile Glu Asn Leu Asn Glu Leu Thr Glu Leu Ala Lys Ser Val
    210                 215                 220
```

-continued

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
            245                 250                 255

Ala Ser Glu Leu Ile Thr Lys Glu Asn Val Thr Thr Arg Gly Ser Glu
        260                 265                 270

Ile Gly Lys Val Tyr Asn Phe Leu Ile Val Leu Thr Ser Leu Gln Ala
    275                 280                 285

Lys Ala Phe Leu Thr Leu Thr Ala Cys Arg Lys Leu Leu Gly Leu Thr
290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
            325                 330                 335

Asn Pro Ser Tyr Ser Lys Asn Arg Gly Ser Asp Ile Asp Asp Pro Ile
        340                 345                 350

Val Val Leu Glu Ala Ala Pro Gly Tyr Ala Leu Ile Gly Phe Glu Ile
    355                 360                 365

Leu Asn Asp Pro Leu Pro Ile Leu Lys Gly Tyr Gln Ala Arg Leu Lys
370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Lys Gln Leu Glu Gln Lys Tyr Tyr
            405                 410                 415

Ile Lys Asp Ile Glu Phe Pro Glu Gly Tyr Val Ile Thr Lys Ile Val
        420                 425                 430

Phe Glu Lys Arg Leu Asn Gln Leu Gly Tyr Glu Val Thr Ala Asn Phe
    435                 440                 445

Tyr Asp Pro Ser Thr Gly Ser Ile Asp Leu Asn Lys Val Lys Val Glu
450                 455                 460

Ser Trp Lys Glu Lys Ser Cys Glu Glu Asp Ser Cys Glu Asp Glu Tyr
465                 470                 475                 480

Ser Ile Ile Lys Ala Glu Thr Asp Gly Ile Tyr Met Pro Leu Gly Val
            485                 490                 495

Val Ser Glu Thr Phe Leu Thr Pro Ile Tyr Gly Phe Gly Leu Thr Val
        500                 505                 510

Asp Glu Lys Asn Gln Lys Ile Thr Leu Thr Gly Lys Ser Tyr Leu Arg
    515                 520                 525

Glu Ser Leu Leu Glu Thr Asp Leu Leu Asn Asn Glu Thr Tyr Leu Ile
530                 535                 540

Ala Ser Pro Asp Gly Tyr Ile Ser Ser Ile Val Glu Asn Trp Asn Ile
545                 550                 555                 560

Thr Ser Asp Asn Thr Gly Ser Trp Arg Ala Asn Asn Asn Ala Phe
            565                 570                 575

Val Asp Lys Ala Asp Thr Ile Lys Gly Ser Ser Ser Leu Tyr Thr His
        580                 585                 590

Lys Asp Gly Glu Phe Ser Gln Phe Ile Gly Asn Lys Leu Lys Pro Lys
    595                 600                 605

Thr Asn Tyr Val Ile Gln Tyr Val Ile Lys Gly Arg Pro Ala Ile Tyr
610                 615                 620

Leu Lys Asn Asn Lys Asp Thr Leu Phe Glu Asp Thr Lys Asn Asn Phe
625                 630                 635                 640

Ser Asp Phe Gln Thr Val Thr Lys Lys Phe Asn Ser Gly Val Asn Pro

```
                      645                 650                 655
Ser Glu Ile Tyr Phe Leu Phe Lys Asn Gln Ser Glu Tyr Glu Ala Trp
                660                 665                 670

Gly Asn Asn Phe Ile Ile Leu Glu Ile Lys Ser Leu Glu Phe Leu Pro
            675                 680                 685

Gln Met Leu Lys Pro Glu Asp Trp Ile Pro Ser Gly Asn Val Gln Met
        690                 695                 700

Lys Asp Gly Gly Arg Leu Glu Ile Leu Gly Asp Gly Tyr Phe Lys Gln
705                 710                 715                 720

Phe Ile Lys Leu Glu Asn Asp Ser Thr Tyr His Leu Arg Leu Ser Val
                725                 730                 735

Lys Gly Thr Gly Arg Val Ser Ile Ile Asp Glu Ser Lys Tyr Phe Leu
            740                 745                 750

Phe Val Asn Val Lys Asp Glu Asp Leu Thr Arg Val Ile Lys Asn Thr
        755                 760                 765

Ser Ser Lys Gly Glu Cys Phe

```
gacatccaca agctgttctg ccctaagcaa ctggagcaga agtactacat caaggacatc    1260
gagttcccgg agggttacgt catcactaag atcgtcttcg agaagcggct gaaccagctt    1320
ggttacgagg tcactgctaa cttctacgac ccgagcactg gtagcatcga cctgaacaag    1380
gtcaaggtcg agagctggaa ggagaagtcc tgcgaggaag actcttgcga ggatgaatac    1440
tctatcatta aggcggagac tgatggtatc tacatgccgc ttggtgtcgt tagtgagact    1500
ttccttactc cgatctacgg tttcggtctt actgtcgatg agaagaacca gaagattact    1560
cttacgggca agtcttacct tcgggagtct ctcctggaga cggatctcct caacaatgag    1620
acgtacctta ttgcgtctcc ggacgggtac atcagttcta ttgtcgagaa ctggaacatt    1680
acgtctgata cacgggctct tggcgtgcg aacaataaca atgcgttcgt cgataaggca    1740
gatacgatta agggctcttc gtctctttac acgcataagg atggcgagtt ctctcagttc    1800
attgggaaca agctcaagcc gaagacgaat tatgtcattc aatacgtcat taagggtcgt    1860
ccagcaatct atcttaagaa taacaaggat acgctcttcg aggatacgaa gaataacttc    1920
tcggacttcc agactgtcac aaagaaattc aattcgggtg tcaatccatc ggaaatctac    1980
tttctcttca agaatcagtc ggagtatgag gcgtggggga acaacttcat catccttgag    2040
atcaagtcgt ggagttctt gccacaaatg ctcaagccag aggactggat tccatcgggc    2100
aatgttcaaa tgaaggatgg aggacgtttg gaaatcttgg gagatggata cttcaaacaa    2160
ttcatcaaac tggagaatga ttcaacatac catctaagac tatcagttaa aggaacagga    2220
cgggtttcaa tcatcgacga gtcaaagtac ctactattcg ttaatgttaa agatgaagac    2280
ctcacacgag tcatcaagaa cactagctca aagggagaat gtttcatagc actcgaagga    2340
acatacgtcg agaactcaag tacaatcttc agtaatgtgt ccatcgtaaa ggagtga      2397
```

<210> SEQ ID NO 6
<211> LENGTH: 2397
<212> TYPE: DNA
<213> ORGANISM: Artificial
<220> FEATURE:
<223> OTHER INFORMATION: Synthetic nucleotide sequence designed for
      expression in a plant cell encoding a TIC2160 protein toxin.

<400> SEQUENCE: 6

```
atgcagcgca tgatcatcgt ggacaacaac aagctgaacg tcagggccct cccgagcttc    60
atcgactact tcaacggcat ctacggcttc gccaccggca tcaaggacat catgggcatg    120
atcttcaaga ctgacaccgg cggtagcaac ctcacccctcg acgagatcct caagaaccag    180
aacctcctca cgacatctc cggcaagctc gacggcatca acggcgaccct cggcgaccct    240 atcgcccagg caacctcaa ctccgagctg gccaaggagc tgctcaagat ctccaacgag    300
cagaaccaga tgctcaacca cgtgaacgcc cagctcaacg ccatcaactc caccctcaac    360
atctacctcc cgaagatcac ctcgatgctc aacgaggtca tgaagcagaa ccacgtgctc    420
tccctccaga tcgagttcct ctccaagcag ctccaggaga tcagcgacaa gctcgacatc    480
attaacctca acgtgctcat caactccacc ctcaccgaga tcactccggc ctaccagcgc    540
atcaagtacg tgaacgagaa gttcgacgag ctgacctcca ccgtggagaa gaacccgaag    600
tcctaccagg acaacgtgac caaggaggtc atcgagaacc tcaacgagct gaccgagctg    660
gccaagtccg tgaccaagaa cgacatggac tccttcgagt tctacctcca gaccttccac    720
gacgtgatga ccggcaacaa tctgttcggc cgctccgccc tcaagaccgc ctccgaactc    780
atcaccaagg agaacgtgac caccccgtggc tccgagatcg gcaaggtgta caacttcctg    840
```

```
atcgtgctga cctccctgca agccaaggct ttcctgaccc tgaccgcttg ccgcaagctg    900
cttggcctga ccgacatcga ctacactcag atcatgaacc accacatcga cggccagaag    960
cgcgagttcc gcatcaacat cctgcccact ctgagcaaca acttcagcaa cccgagctac   1020
agcaagaacc gtggcagcga catcgacgac cccatcgtgg tcctggaggc tgcgcctggc   1080
tacgctctga tcggcttcga gatcctgaac gaccctctgc ctatcctcaa gggctaccag   1140
gctaggctca agccgaacta ccaagtggac cgggagagca tgagcgagac tatctacggt   1200
gacatccaca agctgttctg cccgaagcaa ctggagcaga agtactacat caaggacatc   1260
gagttcccgg agggttacgt catcaccaag atcgtcttcg agaagcggct gaaccagctt   1320
ggttacgagg tcactgctaa cttctacgac ccgagcactg gtagcatcga cctgaacaag   1380
gtcaaggtcg agagctggaa ggagaagtcc tgcgaggaag actcttgcga ggacgagtac   1440
agcatcatca aggcggagac tgatggcatc tacatgccgc ttggtgtcgt aagtgagact   1500
ttcctcactc cgatctacgg cttcggtctc actgtcgatg agaagaacca gaagattact   1560
ctcacgggca agtcttacct tcgggagtct ctcctggaga cggatctcct caacaatgag   1620
acgtacctta ttgcgtctcc ggacgggtac atcagttcca ttgtcgagaa ctggaacatc   1680
acgtctgaca acacgggctc ttggcgtgcg aacaataaca atgcgttcgt cgataaggca   1740
gatacgatca agggctcttc gtctctttac acgcataagg atggcgagtt ctctcagttc   1800
attgggaaca agctcaagcc gaagacgaac tatgtcattc agtacgtcat caagggtcgt   1860
ccagccatct atcttaagaa taacaaggac acgctcttcg aggatacgaa gaataacttc   1920
tcggacttcc agactgtcac caagaagttc aattcgggtg tcaatccatc ggaaatctac   1980
tttctcttca agaatcagtc ggagtatgag gcgtggggga acaacttcat catccttgag   2040
atcaagtcgc tggagttctt gccacagatg ctcaagccag aggactggat tccctcgggc   2100
aatgtccaaa tgaaggatgg aggacgtctg gaaatcttgg gagatggata cttcaaacag   2160
ttcatcaaac tggagaatga ttcaacctac catctaagac tatcagtcaa agggacaggg   2220
cgggtttcaa tcatcgacga gtcaaagtac ctactgttcg tgaatgtcaa agacgaagac   2280
ctcacacgag tcatcaagaa cactagctca aagggagagt gcttcatagc actcgaaggc   2340
acctacgtcg agaacagcag taccatcttc agtaatgtgt ccatcgtcaa ggagtga      2397
```

<210> SEQ ID NO 7
<211> LENGTH: 2397
<212> TYPE: DNA
<213> ORGANISM: Artificial
<220> FEATURE:
<223> OTHER INFORMATION: Synthetic nucleotide sequence designed for expression in a plant cell encoding a TIC3244 protein toxin.

<400> SEQUENCE: 7

```
atgcagcgca tgatcatagt ggacaacaac aagctcaacg tgcgtgccct gccctcgttc     60
atcgactact tcaacgggat ctacggcttc gcgacgggca tcaaggacat catgggcatg    120
atcttcaaga ctgacaccgg cgggtcgaac ctgacgctcg acgagatact gaagaaccag    180
aacctgctga acgacatcag cgggaagctc gacggcatca acggcgacct cggagacctc    240
attgcccagg gcaacctgaa cagcgagctt gccaaggagc tgctgaagat ctccaacgag    300
cagaaccaga tgctgaacca cgtgaacgcg cagcttaacg ccatcaactc gacgctcaac    360
atctacctgc cgaagatcac ctccatgctg aacgaggtca tgaagcagaa ccacgtcctc    420
tcgctgcaga tcgagttcct gagcaagcag ttacaggaga tcagcgacaa gctggacatc    480
```

```
atcaacctga acgtcctgat caactccacc ctcacggaga tcacgccagc gtaccagcgg      540
atcaagtacg tgaacgagaa gttcgacgag ctcacctcga ccgtggagaa gaacccgaag      600
tcgtaccagg acaacgtgac caaggaggtc atcgagaacc tgaacgagct gacggagctg      660
gcgaagtcag tgaccaagaa cgacatggac tccttcgagt tctacctgca gacgttccac      720
gacgtgatga cagggaacaa cctgttcggc cgctcggccc tgaagacggc gagcgagctg      780
atcaccaagg agaacgtgac aacgcgcggc tcggagatcg ggaaggtcta caacttcctc      840
atcgtgctca cctcgctcca ggccaaggcc ttcctgacct tgaccgcctg ccggaagctt      900
cttggcctca ccgacatcga ctacacccag atcatgaacc atcacatcga cggccagaag      960
cgtgagttcc gcatcaacat cctgcccacg ctgagcaaca acttctcgaa tccctcctac     1020
tccaagaaca gaggctccga cattgacgac ccgatcgtgg tgctggaggc tgcgccaggg     1080
tacgccctca taggcttcga gatcctgaac gacccgcttc ccatcctcaa gggctaccag     1140
gctaggttga agccaaacta ccaggtcgac cgggagtcca tgtccgaaac gatctacggc     1200
gacatccaca gttgttctg tcccaagcag ctcgagcaga agtactacat caaggacatt     1260
gagtttcccg agggctacgt catcactaag atcgtgtttg agaagcggct gaaccagctc     1320
ggctacgagg tcaccgcgaa cttctacgat ccctcgacag ggagcatcga cctgaacaag     1380
gtcaaagtgg agagctggaa ggagaagtcc tgcgaggagg actcctgcga ggacgagtac     1440
agcatcatca aggccgagac cgacggcatc tacatgccct gggcgtcgt gtctgagacc      1500 ttcctcactc cgatctacgg cttcgggctg acggtggacg agaagaacca gaagatcaca     1560
ctcacgggca agagctacct tcgagagtct ctccttgaga cagacctgct caacaacgag     1620
acatacctga tcgcgagccc ggatggctac atctcaagta ttgtggagaa ctggaacatc     1680
accagcgaca cacacggcag ctggagggcc aacaacaaca acgccttcgt ggacaaggcc     1740
gacacgatca agggctccag cagcctctac acgcacaagg acggcgagtt cagccagttc     1800
atcgggaaca agctcaagcc gaagacgaac tacgtcatcc agtacgtgat caagggtcgg     1860
ccggcaatct accctcaagaa caacaaagat acgctgttcg aggacaccaa gaacaacttc     1920
tccgacttcc agacggtcac taagaagttc aactccggcg tgaatccctc agagatctac     1980
ttcctgttca agaaccagag cgagtacgag gcctggggca caacttcat catcctcgag     2040 ataaagtccc tggagttcct cccgcagatg ctcaagccgg aggactggat ccctagcggc     2100
aacgtgcaga tgaaggacgg cggccggctg gagatcctcg tgacgggta cttcaagcag     2160 ttcatcaagc tcgagaacga ctccacctac cacctccgcc tcagcgtgaa agggaccggg     2220
cgcgtgtcca tcatcgacga gtccaagtac ttcctgttcg tcaacgtcaa ggacgaggac     2280
ctcaccaggg tcatcaagaa cacctcgtca aagggtgagt gcttcatcgc gctggaggc     2340 acctacgtgg agaacagcag caccatcttc tccaacgtct ccatcgtgaa ggagtga      2397
```

<210> SEQ ID NO 8
<211> LENGTH: 2367
<212> TYPE: DNA
<213> ORGANISM: Artificial
<220> FEATURE:
<223> OTHER INFORMATION: A sequence representing a recombinant
    polynucleotide derived from a TIC2160 gene, and encoding a TIC2160
    Deletion 8 variant protein (TIC2160_Del8).

<400> SEQUENCE: 8

```
atgcaaagga tgataattgt ggataataat aaattaaatg taagagcttt accaagcttt       60
```

```
attgattatt ttaacggtat ttatggattt gccactggta tcaaagatat tatgggaatg    120 attttaaaa cagatacagg tggtagtaat ttaacattag atgagatttt aaagaatcaa    180
aatttactaa atgatatctc aggtaagctc gatggaatta atggagattt aggggatctt    240
attgcacaag ggaacttgaa ttcagaatta gctaaggaat tgctaaaaat ctctaatgag    300
cagaatcaaa tgttaaatca tgttaatgct caacttaatg caatcaattc aacacttaat    360
atatatcttc caaaaattac atctatgtta aatgaggtga tgaagcaaaa ccatgtttta    420
agtctacaaa tagaatttct tagtaagcaa ttgcaggaaa tttcagataa acttgatatt    480
atcaacttaa acgtattgat taactctaca ttaacagaga ttactcctgc ttatcaacgt    540
attaaatatg taaacgaaaa atttgatgaa ttgcttcta ctgtagagaa aaatccaaaa    600
tcatatcaag ataacgttac taagaagtt attgaaaact taaatgagct aactgagttg    660
gcgaaaagtg ttaccaaaaa tgatatggat agttttgaat tttatcttca aactttccat    720
gatgtaatga ctggaaataa tttattcggc cgctcagcat taaaaactgc ttcagaatta    780
attacaaaag aaaatgtcac gacaagggga agtgagatag aaaagttta aatttctta    840 attgttttaa cttctttaca agcaaaagct tttctcactt taactgcatg tcgaaagtta    900
ttaggtttaa cagatatcga ttatactcaa attatgaatc atcatataga tggtcaaaaa    960
agagaatttc gtattaatat tcttccaaca cttttctaata atttttctaa tcctagttat   1020
tcaaaaaata gaggaagtga tatcgatgat ccaattgttg tgttagaagc agcacctgga   1080
tatgccttaa taggatttga aattctaaac gatccacttc caattttaaa aggatatcag   1140
gctaggttaa aaccaaatta tcaagttgac agggagtcga tgtcagaaac gatttatggg   1200
gacattcata aattattttg cccaaaacag ctggagcaaa atattatat aaagatatt    1260 gaatttcctg agggctatgt aattactaaa atcgttttg aaaaaaggct aaatcaattg   1320
gggtatgagg taacagcaaa ttttatgac ccgtctacag gaagtatcga tttaaataag   1380
gttaaagtag aatcttctga agctgagtat agtattataa aggccgaaac ggatggcatt   1440
tatatgccat taggcgtagt aagtgagact ttttaaccc ctatttatgg ttttggatta    1500
acagttgacg aaaaaaatca aaaaataact ttaacaggta aatcctattt acgtgaatcc   1560
ttactagaaa cagacttact taacaatgaa acatatttaa ttgcttcacc agacggttat   1620
attagtagta ttgtagaaaa ctggaatata acatcagata atactgggtc ttggagagca   1680
aataataata atgcatttgt cgataaggca gatactataa aaggatcaag ttctctgtat   1740
actcataaag atggggaatt ctcgcaattt attggaaata agctaaaacc taaaactaat   1800
tatgttattc aatatgttat aaaaggaaga cctgctattt atttaaaaaa taataaagat   1860
actttatttg aggataccaa aaataacttt agcgattttc agactgtaac taaaaaattc   1920
aattcaggag taaatccttc ggaaatttat ttcctttta aaaatcaaag tgaatacgaa   1980
gcctggggaa ataactttat tattttagaa attaaatcgc ttgaattctt gccacaaatg   2040
ctgaagcctg aggattggat accatcagga aatgtgcaaa tgaaagatgg aggacgccta   2100
gagattttgg gagatggtta ttttaaacaa ttcattaaat tggaaaatga ttcaacctat   2160
catctaagat tatctgttaa gggaacaggt agggtatcta taattgatga atctaaatat   2220 ttacttttg taaatgttaa ggatgaagat cttactagag ttattaaaaa tacctcttca   2280
aagggtgagt gttttatagc tcttgagggt acttatgtag aaaattcaag tactattttc   2340
tctaatgtat ctattgttaa agagtaa                                        2367
```

<210> SEQ ID NO 9
<211> LENGTH: 798
<212> TYPE: PRT
<213> ORGANISM: Artificial
<220> FEATURE:
<223> OTHER INFORMATION: An amino acid sequence translation of SEQ ID
      NO: 43 which encodes the TIC2160 variant, TIC2160_Del8 with an
      N-terminal His tag.

<400> SEQUENCE: 9

```
Met Gly Ser Ser His His His His His His Met Gln Arg Met Ile Ile
1               5                   10                  15

Val Asp Asn Asn Lys Leu Asn Val Arg Ala Leu Pro Ser Phe Ile Asp
            20                  25                  30

Tyr Phe Asn Gly Ile Tyr Gly Phe Ala Thr Gly Ile Lys Asp Ile Met
        35                  40                  45

Gly Met Ile Phe Lys Thr Asp Thr Gly Gly Ser Asn Leu Thr Leu Asp
50                  55                  60

Glu Ile Leu Lys Asn Gln Asn Leu Leu Asn Asp Ile Ser Gly Lys Leu
65                  70                  75                  80

Asp Gly Ile Asn Gly Asp Leu Gly Asp Leu Ile Ala Gln Gly Asn Leu
                85                  90                  95

Asn Ser Glu Leu Ala Lys Glu Leu Leu Lys Ile Ser Asn Glu Gln Asn
            100                 105                 110

Gln Met Leu Asn His Val Asn Ala Gln Leu Asn Ala Ile Asn Ser Thr
        115                 120                 125

Leu Asn Ile Tyr Leu Pro Lys Ile Thr Ser Met Leu Asn Glu Val Met
130                 135                 140

Lys Gln Asn His Val Leu Ser Leu Gln Ile Glu Phe Leu Ser Lys Gln
145                 150                 155                 160

Leu Gln Glu Ile Ser Asp Lys Leu Asp Ile Ile Asn Leu Asn Val Leu
                165                 170                 175

Ile Asn Ser Thr Leu Thr Glu Ile Thr Pro Ala Tyr Gln Arg Ile Lys
            180                 185                 190

Tyr Val Asn Glu Lys Phe Asp Glu Leu Thr Ser Thr Val Glu Lys Asn
        195                 200                 205

Pro Lys Ser Tyr Gln Asp Asn Val Thr Lys Glu Val Ile Glu Asn Leu
210                 215                 220

Asn Glu Leu Thr Glu Leu Ala Lys Ser Val Thr Lys Asn Asp Met Asp
225                 230                 235                 240

Ser Phe Glu Phe Tyr Leu Gln Thr Phe His Asp Val Met Thr Gly Asn
                245                 250                 255

Asn Leu Phe Gly Arg Ser Ala Leu Lys Thr Ala Ser Glu Leu Ile Thr
            260                 265                 270

Lys Glu Asn Val Thr Thr Arg Gly Ser Glu Ile Gly Lys Val Tyr Asn
        275                 280                 285

Phe Leu Ile Val Leu Thr Ser Leu Gln Ala Lys Ala Phe Leu Thr Leu
290                 295                 300

Thr Ala Cys Arg Lys Leu Leu Gly Leu Thr Asp Ile Asp Tyr Thr Gln
305                 310                 315                 320

Ile Met Asn His His Ile Asp Gly Gln Lys Arg Glu Phe Arg Ile Asn
                325                 330                 335

Ile Leu Pro Thr Leu Ser Asn Asn Phe Ser Asn Pro Ser Tyr Ser Lys
            340                 345                 350

Asn Arg Gly Ser Asp Ile Asp Asp Pro Ile Val Val Leu Glu Ala Ala
        355                 360                 365
```

-continued

Pro Gly Tyr Ala Leu Ile Gly Phe Glu Ile Leu Asn Asp Pro Leu Pro
    370                 375                 380

Ile Leu Lys Gly Tyr Gln Ala Arg Leu Lys Pro Asn Tyr Gln Val Asp
385                 390                 395                 400

Arg Glu Ser Met Ser Glu Thr Ile Tyr Gly Asp Ile His Lys Leu Phe
                405                 410                 415

Cys Pro Lys Gln Leu Glu Gln Lys Tyr Tyr Ile Lys Asp Ile Glu Phe
            420                 425                 430

Pro Glu Gly Tyr Val Ile Thr Lys Ile Val Phe Glu Lys Arg Leu Asn
        435                 440                 445

Gln Leu Gly Tyr Glu Val Thr Ala Asn Phe Tyr Asp Pro Ser Thr Gly
    450                 455                 460

Ser Ile Asp Leu Asn Lys Val Lys Val Glu Ser Ser Glu Ala Glu Tyr
465                 470                 475                 480

Ser Ile Ile Lys Ala Glu Thr Asp Gly Ile Tyr Met Pro Leu Gly Val
                485                 490                 495

Val Ser Glu Thr Phe Leu Thr Pro Ile Tyr Gly Phe Gly Leu Thr Val
            500                 505                 510

Asp Glu Lys Asn Gln Lys Ile Thr Leu Thr Gly Lys Ser Tyr Leu Arg
        515                 520                 525

Glu Ser Leu Leu Glu Thr Asp Leu Leu Asn Asn Glu Thr Tyr Leu Ile
    530                 535                 540

Ala Ser Pro Asp Gly Tyr Ile Ser Ser Ile Val Glu Asn Trp Asn Ile
545                 550                 555                 560

Thr Ser Asp Asn Thr Gly Ser Trp Arg Ala Asn Asn Asn Ala Phe
                565                 570                 575

Val Asp Lys Ala Asp Thr Ile Lys Gly Ser Ser Ser Leu Tyr Thr His
            580                 585                 590

Lys Asp Gly Glu Phe Ser Gln Phe Ile Gly Asn Lys Leu Lys Pro Lys
        595                 600                 605

Thr Asn Tyr Val Ile Gln Tyr Val Ile Lys Gly Arg Pro Ala Ile Tyr
    610                 615                 620

Leu Lys Asn Asn Lys Asp Thr Leu Phe Glu Asp Thr Lys Asn Asn Phe
625                 630                 635                 640

Ser Asp Phe Gln Thr Val Thr Lys Lys Phe Asn Ser Gly Val Asn Pro
                645                 650                 655

Ser Glu Ile Tyr Phe Leu Phe Lys Asn Gln Ser Glu Tyr Glu Ala Trp
            660                 665                 670

Gly Asn Asn Phe Ile Ile Leu Glu Ile Lys Ser Leu Glu Phe Leu Pro
        675                 680                 685

Gln Met Leu Lys Pro Glu Asp Trp Ile Pro Ser Gly Asn Val Gln Met
    690                 695                 700

Lys Asp Gly Gly Arg Leu Glu Ile Leu Gly Asp Gly Tyr Phe Lys Gln
705                 710                 715                 720

Phe Ile Lys Leu Glu Asn Asp Ser Thr Tyr His Leu Arg Leu Ser Val
                725                 730                 735

Lys Gly Thr Gly Arg Val Ser Ile Ile Asp Glu Ser Lys Tyr Leu Leu
            740                 745                 750

Phe Val Asn Val Lys Asp Glu Asp Leu Thr Arg Val Ile Lys Asn Thr
        755                 760                 765

Ser Ser Lys Gly Glu Cys Phe Ile Ala Leu Glu Gly Thr Tyr Val Glu
    770                 775                 780

Asn Ser Ser Thr Ile Phe Ser Asn Val Ser Ile Val Lys Glu
785                 790                 795

<210> SEQ ID NO 10
<211> LENGTH: 788
<212> TYPE: PRT
<213> ORGANISM: Artificial
<220> FEATURE:
<223> OTHER INFORMATION: An amino acid sequence translation of SEQ ID
      NO: 11 which encodes the TIC2160 variant, TIC2160_Del8.

<400> SEQUENCE: 10

Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
                20                  25                  30

Gly Ile Lys Asp Ile Met Gly Met Ile Phe Lys Thr Asp Thr Gly Gly
            35                  40                  45

Ser Asn Leu Thr Leu Asp Glu Ile Leu Lys Asn Gln Asn Leu Leu Asn
50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
                165                 170                 175

Ala Tyr Gln Arg Ile Lys Tyr Val Asn Glu Lys Phe Asp Glu Leu Thr
            180                 185                 190

Ser Thr Val Glu Lys Asn Pro Lys Ser Tyr Gln Asp Asn Val Thr Lys
        195                 200                 205

Glu Val Ile Glu Asn Leu Asn Glu Leu Thr Glu Leu Ala Lys Ser Val
210                 215                 220

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
                245                 250                 255

Ala Ser Glu Leu Ile Thr Lys Glu Asn Val Thr Thr Arg Gly Ser Glu
            260                 265                 270

Ile Gly Lys Val Tyr Asn Phe Leu Ile Val Leu Thr Ser Leu Gln Ala
        275                 280                 285

Lys Ala Phe Leu Thr Leu Thr Ala Cys Arg Lys Leu Leu Gly Leu Thr
290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
                325                 330                 335

Asn Pro Ser Tyr Ser Lys Asn Arg Gly Ser Asp Ile Asp Pro Ile
            340                 345                 350

```
Val Val Leu Glu Ala Ala Pro Gly Tyr Ala Leu Ile Gly Phe Glu Ile
        355                 360                 365

Leu Asn Asp Pro Leu Pro Ile Leu Lys Gly Tyr Gln Ala Arg Leu Lys
    370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Lys Gln Leu Glu Gln Lys Tyr Tyr
                405                 410                 415

Ile Lys Asp Ile Glu Phe Pro Glu Gly Tyr Val Ile Thr Lys Ile Val
                420                 425                 430

Phe Glu Lys Arg Leu Asn Gln Leu Gly Tyr Glu Val Thr Ala Asn Phe
        435                 440                 445

Tyr Asp Pro Ser Thr Gly Ser Ile Asp Leu Asn Lys Val Lys Val Glu
    450                 455                 460

Ser Ser Glu Ala Glu Tyr Ser Ile Ile Lys Ala Glu Thr Asp Gly Ile
465                 470                 475                 480

Tyr Met Pro Leu Gly Val Val Ser Glu Thr Phe Leu Thr Pro Ile Tyr
                485                 490                 495

Gly Phe Gly Leu Thr Val Asp Glu Lys Asn Gln Lys Ile Thr Leu Thr
                500                 505                 510

Gly Lys Ser Tyr Leu Arg Glu Ser Leu Leu Glu Thr Asp Leu Leu Asn
        515                 520                 525

Asn Glu Thr Tyr Leu Ile Ala Ser Pro Asp Gly Tyr Ile Ser Ser Ile
    530                 535                 540

Val Glu Asn Trp Asn Ile Thr Ser Asp Asn Thr Gly Ser Trp Arg Ala
545                 550                 555                 560

Asn Asn Asn Asn Ala Phe Val Asp Lys Ala Asp Thr Ile Lys Gly Ser
                565                 570                 575

Ser Ser Leu Tyr Thr His Lys Asp Gly Glu Phe Ser Gln Phe Ile Gly
                580                 585                 590

Asn Lys Leu Lys Pro Lys Thr Asn Tyr Val Ile Gln Tyr Val Ile Lys
        595                 600                 605

Gly Arg Pro Ala Ile Tyr Leu Lys Asn Asn Lys Asp Thr Leu Phe Glu
    610                 615                 620

Asp Thr Lys Asn Asn Phe Ser Asp Phe Gln Thr Val Thr Lys Lys Phe
625                 630                 635                 640

Asn Ser Gly Val Asn Pro Ser Glu Ile Tyr Phe Leu Phe Lys Asn Gln
                645                 650                 655

Ser Glu Tyr Glu Ala Trp Gly Asn Asn Phe Ile Ile Leu Glu Ile Lys
                660                 665                 670

Ser Leu Glu Phe Leu Pro Gln Met Leu Lys Pro Glu Asp Trp Ile Pro
        675                 680                 685

Ser Gly Asn Val Gln Met Lys Asp Gly Gly Arg Leu Glu Ile Leu Gly
    690                 695                 700

Asp Gly Tyr Phe Lys Gln Phe Ile Lys Leu Glu Asn Asp Ser Thr Tyr
705                 710                 715                 720

His Leu Arg Leu Ser Val Lys Gly Thr Gly Arg Val Ser Ile Ile Asp
                725                 730                 735

Glu Ser Lys Tyr Leu Leu Phe Val Asn Val Lys Asp Glu Asp Leu Thr
                740                 745                 750

Arg Val Ile Lys Asn Thr Ser Ser Lys Gly Glu Cys Phe Ile Ala Leu
        755                 760                 765
```

Glu Gly Thr Tyr Val Glu Asn Ser Ser Thr Ile Phe Ser Asn Val Ser
    770                 775                 780

Ile Val Lys Glu
785

<210> SEQ ID NO 11
<211> LENGTH: 2367
<212> TYPE: DNA
<213> ORGANISM: Artificial
<220> FEATURE:
<223> OTHER INFORMATION: A synthetic nucleotide sequence designed for
      expression in a plant cell encoding the TIC2160 variant,
      TIC2160_Del8.

<400> SEQUENCE: 11

| | | | |
|---|---|---|---|
| atgcagcgca tgatcatcgt ggacaacaac aagctgaacg tcagggccct cccgagcttc | 60 |
| atcgactact tcaacggcat ctacggcttc gccaccggca tcaaggacat catgggcatg | 120 |
| atcttcaaga ctgacaccgg cggtagcaac ctcacccctcg acgagatcct caagaaccag | 180 |
| aacctcctca cgacatctc cggcaagctc gacggcatca acggcgaccct cggcgaccct | 240 |
| atcgcccagg gcaacctcaa ctccgagctg ccaaggagc tgctcaagat ctccaacgag | 300 |
| cagaaccaga tgctcaacca cgtgaacgcc agctcaacg ccatcaactc caccctcaac | 360 |
| atctacctcc cgaagatcac ctcgatgctc aacgaggtca tgaagcagaa ccacgtgctc | 420 |
| tccctccaga tcgagttcct ctccaagcag ctccaggaga tcagcgacaa gctcgacatc | 480 |
| attaacctca cgtgctcat caactccacc ctcaccgaga tcactccggc ctaccagcgc | 540 |
| atcaagtacg tgaacgagaa gttcgacgag ctgacctcca ccgtggagaa gaacccgaag | 600 |
| tcctaccagg acaacgtgac caaggaggtc atcgagaacc tcaacgagct gaccgagctg | 660 |
| gccaagtccg tgaccaagaa cgacatggac tccttcgagt tctacctcca gaccttccac | 720 |
| gacgtgatga ccggcaacaa tctgttcggc cgctccgccc tcaagaccgc ctccgaactc | 780 |
| atcaccaagg agaacgtgac cacccgtggc tccgagatcg gcaaggtgta caacttcctg | 840 |
| atcgtgctga cctccctgca agccaaggct ttcctgaccc tgaccgcttg ccgcaagctg | 900 |
| cttggcctga ccgacatcga ctacactcag atcatgaacc accacatcga cggccagaag | 960 |
| cgcgagttcc gcatcaacat cctgcccact ctgagcaaca acttcagcaa cccgagctac | 1020 |
| agcaagaacc gtggcagcga catcgacgac cccatcgtgg tcctggaggc tgcgcctggc | 1080 |
| tacgctctga tcggcttcga gatcctgaac gaccctctgc ctatcctcaa gggctaccag | 1140 |
| gctaggctca agccgaacta ccaagtggac cgggagagca tgagcgagac tatctacggt | 1200 |
| gacatccaca agctgttctg cccgaagcaa ctggagcaga agtactacat caaggacatc | 1260 |
| gagttcccgg agggttacgt catcaccaag atcgtcttcg agaagcggct gaaccagctt | 1320 |
| ggttacgagg tcactgctaa cttctacgac ccgagcactg gtagcatcga cctgaacaag | 1380 |
| gtcaaggtcg agagcagcga ggcggagtac agcatcatca aggcggagac tgatggcatc | 1440 |
| tacatgccgc ttggtgtcgt aagtgagact ttcctcactc cgatctacgg cttcggtctc | 1500 |
| actgtcgatg agaagaacca gaagattact ctcacgggca gtcttacct cgggagtct | 1560 |
| ctcctggaga cggatctcct caacaatgag acgtaccttta ttgcgtctcc ggacgggtac | 1620 |
| atcagttcca ttgtcgagaa ctggaacatc acgtctgaca cacgggctc ttggcgtgcg | 1680 |
| aacaataaca atgcgttcgt cgataaggca gatacgatca agggctcttc gtctctttac | 1740 |
| acgcataagg atgcgagtt ctctcagttc attgggaaca agctcaagcc gaagacgaac | 1800 |
| tatgtcattc agtacgtcat caagggtcgt ccagccatct atcttaagaa taacaaggac | 1860 |

```
acgctcttcg aggatacgaa gaataacttc tcggacttcc agactgtcac caagaagttc    1920
aattcgggtg tcaatccatc ggaaatctac tttctcttca agaatcagtc ggagtatgag    1980
gcgtggggga acaacttcat catccttgag atcaagtcgc tggagttctt gccacagatg    2040
ctcaagccag aggactggat tccctcgggc aatgtccaaa tgaaggatgg aggacgtctg    2100
gaaatcttgg gagatggata cttcaaacag ttcatcaaac tggagaatga ttcaacctac    2160
catctaagac tatcagtcaa agggacaggg cgggtttcaa tcatcgacga gtcaaagtac    2220
ctactgttcg tgaatgtcaa agacgaagac ctcacacgag tcatcaagaa cactagctca    2280
aagggagagt gcttcatagc actcgaaggc acctacgtcg agaacagcag taccatcttc    2340
agtaatgtgt ccatcgtcaa ggagtga                                        2367
```

<210> SEQ ID NO 12
<211> LENGTH: 808
<212> TYPE: PRT
<213> ORGANISM: Artificial
<220> FEATURE:
<223> OTHER INFORMATION: An amino acid sequence of a TIC2160 protein
fused with an N-terminal HIS tag (MGSSHHHHHH)
(TIC2160_MGSSHHHHHH) and is encoded by SEQ ID NO: 42.

<400> SEQUENCE: 12

```
Met Gly Ser Ser His His His His His His Gln Arg Met Ile Ile
1               5                   10                  15

Val Asp Asn Asn Lys Leu Asn Val Arg Ala Leu Pro Ser Phe Ile Asp
            20                  25                  30

Tyr Phe Asn Gly Ile Tyr Gly Phe Ala Thr Gly Ile Lys Asp Ile Met
        35                  40                  45

Gly Met Ile Phe Lys Thr Asp Thr Gly Gly Ser Asn Leu Thr Leu Asp
    50                  55                  60

Glu Ile Leu Lys Asn Gln Asn Leu Leu Asn Asp Ile Ser Gly Lys Leu
65                  70                  75                  80

Asp Gly Ile Asn Gly Asp Leu Gly Asp Leu Ile Ala Gln Gly Asn Leu
                85                  90                  95

Asn Ser Glu Leu Ala Lys Glu Leu Leu Lys Ile Ser Asn Glu Gln Asn
            100                 105                 110

Gln Met Leu Asn His Val Asn Ala Gln Leu Asn Ala Ile Asn Ser Thr
        115                 120                 125

Leu Asn Ile Tyr Leu Pro Lys Ile Thr Ser Met Leu Asn Glu Val Met
    130                 135                 140

Lys Gln Asn His Val Leu Ser Leu Gln Ile Glu Phe Leu Ser Lys Gln
145                 150                 155                 160

Leu Gln Glu Ile Ser Asp Lys Leu Asp Ile Ile Asn Leu Asn Val Leu
                165                 170                 175

Ile Asn Ser Thr Leu Thr Glu Ile Thr Pro Ala Tyr Gln Arg Ile Lys
            180                 185                 190

Tyr Val Asn Glu Lys Phe Asp Glu Leu Thr Ser Thr Val Glu Lys Asn
        195                 200                 205

Pro Lys Ser Tyr Gln Asp Asn Val Thr Lys Glu Val Ile Glu Asn Leu
    210                 215                 220

Asn Glu Leu Thr Glu Leu Ala Lys Ser Val Thr Lys Asn Asp Met Asp
225                 230                 235                 240

Ser Phe Glu Phe Tyr Leu Gln Thr Phe His Asp Val Met Thr Gly Asn
                245                 250                 255
```

```
Asn Leu Phe Gly Arg Ser Ala Leu Lys Thr Ala Ser Glu Leu Ile Thr
            260                 265                 270

Lys Glu Asn Val Thr Thr Arg Gly Ser Glu Ile Gly Lys Val Tyr Asn
        275                 280                 285

Phe Leu Ile Val Leu Thr Ser Leu Gln Ala Lys Ala Phe Leu Thr Leu
        290                 295                 300

Thr Ala Cys Arg Lys Leu Leu Gly Leu Thr Asp Ile Asp Tyr Thr Gln
305                 310                 315                 320

Ile Met Asn His His Ile Asp Gly Gln Lys Arg Glu Phe Arg Ile Asn
                325                 330                 335

Ile Leu Pro Thr Leu Ser Asn Asn Phe Ser Asn Pro Ser Tyr Ser Lys
            340                 345                 350

Asn Arg Gly Ser Asp Ile Asp Asp Pro Ile Val Val Leu Glu Ala Ala
        355                 360                 365

Pro Gly Tyr Ala Leu Ile Gly Phe Glu Ile Leu Asn Asp Pro Leu Pro
        370                 375                 380

Ile Leu Lys Gly Tyr Gln Ala Arg Leu Lys Pro Asn Tyr Gln Val Asp
385                 390                 395                 400

Arg Glu Ser Met Ser Glu Thr Ile Tyr Gly Asp Ile His Lys Leu Phe
                405                 410                 415

Cys Pro Lys Gln Leu Glu Gln Lys Tyr Tyr Ile Lys Asp Ile Glu Phe
            420                 425                 430

Pro Glu Gly Tyr Val Ile Thr Lys Ile Val Phe Glu Lys Arg Leu Asn
        435                 440                 445

Gln Leu Gly Tyr Glu Val Thr Ala Asn Phe Tyr Asp Pro Ser Thr Gly
        450                 455                 460

Ser Ile Asp Leu Asn Lys Val Lys Val Glu Ser Trp Lys Glu Lys Ser
465                 470                 475                 480

Cys Glu Glu Asp Ser Cys Glu Asp Gly Tyr Ser Ile Ile Lys Ala Glu
                485                 490                 495

Thr Asp Gly Ile Tyr Met Pro Leu Gly Val Val Ser Glu Thr Phe Leu
            500                 505                 510

Thr Pro Ile Tyr Gly Phe Gly Leu Thr Val Asp Glu Lys Asn Gln Lys
        515                 520                 525

Ile Thr Leu Thr Gly Lys Ser Tyr Leu Arg Glu Ser Leu Leu Glu Thr
        530                 535                 540

Asp Leu Leu Asn Asn Glu Thr Tyr Leu Ile Ala Ser Pro Asp Gly Tyr
545                 550                 555                 560

Ile Ser Ser Ile Val Glu Asn Trp Asn Ile Thr Ser Asp Asn Thr Gly
                565                 570                 575

Ser Trp Arg Ala Asn Asn Asn Ala Phe Val Asp Lys Ala Asp Thr
            580                 585                 590

Ile Lys Gly Ser Ser Ser Leu Tyr Thr His Lys Asp Gly Glu Phe Ser
        595                 600                 605

Gln Phe Ile Gly Asn Lys Leu Lys Pro Lys Thr Asn Tyr Val Ile Gln
        610                 615                 620

Tyr Val Ile Lys Gly Arg Pro Ala Ile Tyr Leu Lys Asn Asn Lys Asp
625                 630                 635                 640

Thr Leu Phe Glu Asp Thr Lys Asn Asn Phe Ser Asp Phe Gln Thr Val
                645                 650                 655

Thr Lys Lys Phe Asn Ser Gly Val Asn Pro Ser Glu Ile Tyr Phe Leu
            660                 665                 670

Phe Lys Asn Gln Ser Glu Tyr Glu Ala Trp Gly Asn Asn Phe Ile Ile
```

```
                675                 680                 685
Leu Glu Ile Lys Ser Leu Glu Phe Leu Pro Gln Met Leu Lys Pro Glu
        690                 695                 700

Asp Trp Ile Pro Ser Gly Asn Val Gln Met Lys Asp Gly Gly Arg Leu
705                 710                 715                 720

Glu Ile Leu Gly Asp Gly Tyr Phe Lys Gln Phe Ile Lys Leu Glu Asn
                725                 730                 735

Asp Ser Thr Tyr His Leu Arg Leu Ser Val Lys Gly Thr Gly Arg Val
            740                 745                 750

Ser Ile Ile Asp Glu Ser Lys Tyr Leu Leu Phe Val Asn Val Lys Asp
        755                 760                 765

Glu Asp Leu Thr Arg Val Ile Lys Asn Thr Ser Ser Lys Gly Glu Cys
    770                 775                 780

Phe Ile Ala Leu Glu Gly Thr Tyr Val Glu Asn Ser Ser Thr Ile Phe
785                 790                 795                 800

Ser Asn Val Ser Ile Val Lys Glu
                805

<210> SEQ ID NO 13
<211> LENGTH: 27
<212> TYPE: DNA
<213> ORGANISM: Artificial
<220> FEATURE:
<223> OTHER INFORMATION: A primer sequence representing NT positions 1
      through 27 of SEQ ID NO: 1.

<400> SEQUENCE: 13
atgcaaagga tgataattgt ggataat                                        27

<210> SEQ ID NO 14
<211> LENGTH: 28
<212> TYPE: DNA
<213> ORGANISM: Artificial
<220> FEATURE:
<223> OTHER INFORMATION: A primer sequence representing complementary NT
      positions 2397 through 2370 of SEQ ID NO: 1 with one G2397A
      substitution.

<400> SEQUENCE: 14
ttactcttta acaatagata cattagag                                       28

<210> SEQ ID NO 15
<211> LENGTH: 23
<212> TYPE: DNA
<213> ORGANISM: Artificial
<220> FEATURE:
<223> OTHER INFORMATION: A primer sequence representing NT positions 517
      through 539 of SEQ ID NO: 1.

<400> SEQUENCE: 15
gagattactc ctgcttatca acg                                            23

<210> SEQ ID NO 16
<211> LENGTH: 22
<212> TYPE: DNA
<213> ORGANISM: Artificial
<220> FEATURE:
<223> OTHER INFORMATION: A primer sequence representing NT positions
      1350 through 1371 of SEQ ID NO: 1.

<400> SEQUENCE: 16
cccgtctaca ggaagtatcg at                                             22
```

<210> SEQ ID NO 17
<211> LENGTH: 22
<212> TYPE: DNA
<213> ORGANISM: Artificial
<220> FEATURE:
<223> OTHER INFORMATION: A primer sequence representing complementary NT
      positions 1371 through 1350 of SEQ ID NO: 1.

<400> SEQUENCE: 17
atcgatactt cctgtagacg gg                                              22

<210> SEQ ID NO 18
<211> LENGTH: 2433
<212> TYPE: DNA
<213> ORGANISM: Artificial
<220> FEATURE:
<223> OTHER INFORMATION: A synthetic nucleotide sequence representing a
      recombinant polynucleotide derived from a TIC2160 gene encoding a
      TIC2160 variant protein (Variant-a-058).

<400> SEQUENCE: 18
atgggcagca gccatcatca tcatcatcac cacatgattg tggataataa taaattaaat      60
gtaagagctt taccaagctt tattgattat tttaacggta tttatggatt tgccactggt     120
atcaaagata ttatgggaat gatttttaaa acagatacag gtggtagtaa tttaacatta     180
gatgagattt taaagaatca aaatttacta atgatatct cgggtaagct cgatggtatt      240
aatggaggtt taggtgatct tattgcacaa gggaacttaa attcagaatt agctaaggaa     300
ttgctaaaaa tttctaatga gcagaatcag atgttaaatc atgttaatgc tcaacttaat     360
gcaatcaatt caacacttaa tgtatatctt cccaaaatta catctatgtt aaatgaggtg     420
atgatgcaaa accatgtttt aagtctacaa atagaatttc taagtaaaca attgcaagaa     480
atttcagata aacttgatat tatcaactta aacgtactga ttaactctac attgacagag     540
attactcctg cttatcaacg tattaaatat gttaacgaaa aatttgatga attgacttct     600
actgtagatt ctcgtggtcg ttcttatcaa gataacgtta ctaaagaagt tattaatgaa     660
ttaactgatc taactgaatt ggccaaaagt gttacaaaaa atgatatgga tagttttgaa     720
ttttatcttc aaactttcca tgatgtaatg actggaaata atttatttgg taaatcagca     780
ttacgtactg ctgcacaatt aatcacaaaa aatgaaacag taacaagagg aagtgagata     840
ggaaaagttt ataattctt gattgtttta acttctttac aagcaaaagc ttttctcact      900
ttaactgcat gtcgaaagtt attgggttta acagatattg attatactaa aactatgaat     960
cagcatttag atggacaaaa aagagaattt cgtattaata ttcttccaac actttctaat    1020
agttttctta tcctagttta ttcaaagaat agaggaagtg atatcgatga tccaattgtt    1080
gtgttagaag cagcacctgg atatgcctta ataggatttc aaattctaaa cgatccactt    1140
ccgattttaa aaggatatca ggctaggtta aaaccaaatt atcaagttga cagagagtcg    1200
atgtcagaaa caatttatgg ggatattcat aaattatttt gtccaaaaca gctggagcaa    1260
aaatattata ttaaagatat tgaatttcct gaaggctatg taatcactaa aatcgtgttt    1320
gaaaaaaggc taaatcaatt gggttatgag gtaacggcaa attttatga cccctctaca     1380 ggaaacatcg atttaaacaa ggttaaagta gaatcttgga aggaaaagtc ttgcgaggag    1440
gaatcctgcg aagatgagtt ctgcgaacat gagtatagcc ttataaaggc tgaaacggat    1500
ggtatttata tgccattagg tgtagtaagt gagaccttt taaccccaat ttatggtttt     1560
ggattaacag ttgacgaaaa aaatcaaaaa ataactttaa caggtaaatc ctatttacgt    1620

-continued

```
gaatccttac tagaaacaga tttagttaac aatgaaacat atttaattgc ttcaccagac    1680
ggttatttta gtagtattgt agaaaattgg aatataacat cagataattt tggatcttgg    1740
agagcaaata ataataatgc atttgtcgat aaggaagata ctgtaaaagg atcaagttct    1800
ctgtatactc ataaagatgg ggaattctcg caatttattg gaaataagct aaaacctaaa    1860
actaattatg ttattcaata tgctataaaa ggaagacccg ctatttattt aaaaaataat    1920
aaggatacct tgtttgagga taccaataac aactttagcg attttcagac tgtaacaaaa    1980
aaattcaatt caggagcaaa tccttcggaa atttatttgc ttttttaaaaa tcaaggtgaa    2040
tacgaggctt gggggaataa ctttattatt ttagaaatta aatcgcttga attattgccg    2100
caaatgttga aacctgagga ttggatacca tcaggaaatg tgcaaatgaa agacgaagga    2160
cgcctagaga ttttaggaga tggctatttt aaacaattca ttaaattgca aaatgattca    2220
acctatcatc taagattatc agttaaggga accggtaggg tatcaataat tgatgaatct    2280
aactatttat tttttgtaaa tattaaggat gaagattttta ctagcgttat taaaaatagg    2340
tcttcagaag gtgattgttt tatagctctt gagggttctt atgtagaaaa ttctagtacc    2400
attttttcta gtgtatctat cgttaaagaa tag                                 2433
```

<210> SEQ ID NO 19
<211> LENGTH: 810
<212> TYPE: PRT
<213> ORGANISM: Artificial
<220> FEATURE:
<223> OTHER INFORMATION: An amino acid sequence of a TIC2160 variant protein (Variant-a-058) encoded by SEQ ID NO: 18.

<400> SEQUENCE: 19

Met Gly Ser Ser His His His His His His Met Ile Val Asp Asn
1               5                   10                  15

Asn Lys Leu Asn Val Arg Ala Leu Pro Ser Phe Ile Asp Tyr Phe Asn
            20                  25                  30

Gly Ile Tyr Gly Phe Ala Thr Gly Ile Lys Asp Ile Met Gly Met Ile
        35                  40                  45

Phe Lys Thr Asp Thr Gly Gly Ser Asn Leu Thr Leu Asp Glu Ile Leu
    50                  55                  60

Lys Asn Gln Asn Leu Leu Asn Asp Ile Ser Gly Lys Leu Asp Gly Ile
65                  70                  75                  80

Asn Gly Gly Leu Gly Asp Leu Ile Ala Gln Gly Asn Leu Asn Ser Glu
                85                  90                  95

Leu Ala Lys Glu Leu Leu Lys Ile Ser Asn Glu Gln Asn Gln Met Leu
            100                 105                 110

Asn His Val Asn Ala Gln Leu Asn Ala Ile Asn Ser Thr Leu Asn Val
        115                 120                 125

Tyr Leu Pro Lys Ile Thr Ser Met Leu Asn Glu Val Met Met Gln Asn
    130                 135                 140

His Val Leu Ser Leu Gln Ile Glu Phe Leu Ser Lys Gln Leu Gln Glu
145                 150                 155                 160

Ile Ser Asp Lys Leu Asp Ile Ile Asn Leu Asn Val Leu Ile Asn Ser
                165                 170                 175

Thr Leu Thr Glu Ile Thr Pro Ala Tyr Gln Arg Ile Lys Tyr Val Asn
            180                 185                 190

Glu Lys Phe Asp Glu Leu Thr Ser Thr Val Asp Ser Arg Gly Arg Ser
        195                 200                 205

Tyr Gln Asp Asn Val Thr Lys Glu Val Ile Asn Glu Leu Thr Asp Leu

```
                210                 215                 220
Thr Glu Leu Ala Lys Ser Val Thr Lys Asn Asp Met Asp Ser Phe Glu
225                 230                 235                 240

Phe Tyr Leu Gln Thr Phe His Asp Val Met Thr Gly Asn Asn Leu Phe
                245                 250                 255

Gly Lys Ser Ala Leu Arg Thr Ala Ala Gln Leu Ile Thr Lys Asn Glu
                260                 265                 270

Thr Val Thr Arg Gly Ser Glu Ile Gly Lys Val Tyr Asn Phe Leu Ile
                275                 280                 285

Val Leu Thr Ser Leu Gln Ala Lys Ala Phe Leu Thr Leu Thr Ala Cys
            290                 295                 300

Arg Lys Leu Leu Gly Leu Thr Asp Ile Asp Tyr Thr Lys Thr Met Asn
305                 310                 315                 320

Gln His Leu Asp Gly Gln Lys Arg Glu Phe Arg Ile Asn Ile Leu Pro
                325                 330                 335

Thr Leu Ser Asn Ser Phe Ser Asn Pro Ser Tyr Ser Lys Asn Arg Gly
                340                 345                 350

Ser Asp Ile Asp Asp Pro Ile Val Leu Glu Ala Ala Pro Gly Tyr
            355                 360                 365

Ala Leu Ile Gly Phe Gln Ile Leu Asn Asp Pro Leu Pro Ile Leu Lys
370                 375                 380

Gly Tyr Gln Ala Arg Leu Lys Pro Asn Tyr Gln Val Asp Arg Glu Ser
385                 390                 395                 400

Met Ser Glu Thr Ile Tyr Gly Asp Ile His Lys Leu Phe Cys Pro Lys
                405                 410                 415

Gln Leu Glu Gln Lys Tyr Tyr Ile Lys Asp Ile Glu Phe Pro Glu Gly
                420                 425                 430

Tyr Val Ile Thr Lys Ile Val Phe Glu Lys Arg Leu Asn Gln Leu Gly
                435                 440                 445

Tyr Glu Val Thr Ala Asn Phe Tyr Asp Pro Ser Thr Gly Asn Ile Asp
                450                 455                 460

Leu Asn Lys Val Lys Val Glu Ser Trp Lys Glu Lys Ser Cys Glu Glu
465                 470                 475                 480

Glu Ser Cys Glu Asp Glu Phe Cys Glu His Glu Tyr Ser Leu Ile Lys
                485                 490                 495

Ala Glu Thr Asp Gly Ile Tyr Met Pro Leu Gly Val Val Ser Glu Thr
                500                 505                 510

Phe Leu Thr Pro Ile Tyr Gly Phe Gly Leu Thr Val Asp Glu Lys Asn
                515                 520                 525

Gln Lys Ile Thr Leu Thr Gly Lys Ser Tyr Leu Arg Glu Ser Leu Leu
                530                 535                 540

Glu Thr Asp Leu Val Asn Asn Glu Thr Tyr Leu Ile Ala Ser Pro Asp
545                 550                 555                 560

Gly Tyr Phe Ser Ser Ile Val Glu Asn Trp Asn Ile Thr Ser Asp Asn
                565                 570                 575

Phe Gly Ser Trp Arg Ala Asn Asn Asn Ala Phe Val Asp Lys Glu
                580                 585                 590

Asp Thr Val Lys Gly Ser Ser Leu Tyr Thr His Lys Asp Gly Glu
                595                 600                 605

Phe Ser Gln Phe Ile Gly Asn Lys Leu Lys Pro Lys Thr Asn Tyr Val
                610                 615                 620

Ile Gln Tyr Ala Ile Lys Gly Arg Pro Ala Ile Tyr Leu Lys Asn Asn
625                 630                 635                 640
```

| Lys | Asp | Thr | Leu | Phe | Glu | Asp | Thr | Asn | Asn | Asn | Phe | Ser | Asp | Phe | Gln |
|-----|-----|-----|-----|-----|-----|-----|-----|-----|-----|-----|-----|-----|-----|-----|-----|
|     |     |     | 645 |     |     |     |     | 650 |     |     |     |     | 655 |     |     |

Thr Val Thr Lys Lys Phe Asn Ser Gly Ala Asn Pro Ser Glu Ile Tyr
            660               665               670

Leu Leu Phe Lys Asn Gln Gly Glu Tyr Glu Ala Trp Gly Asn Asn Phe
            675               680               685

Ile Ile Leu Glu Ile Lys Ser Leu Glu Leu Pro Gln Met Leu Lys
            690               695               700

Pro Glu Asp Trp Ile Pro Ser Gly Asn Val Gln Met Lys Asp Glu Gly
705                710               715               720

Arg Leu Glu Ile Leu Gly Asp Gly Tyr Phe Lys Gln Phe Ile Lys Leu
            725               730               735

Gln Asn Asp Ser Thr Tyr His Leu Arg Leu Ser Val Lys Gly Thr Gly
            740               745               750

Arg Val Ser Ile Ile Asp Glu Ser Asn Tyr Leu Phe Phe Val Asn Ile
            755               760               765

Lys Asp Glu Asp Phe Thr Ser Val Ile Lys Asn Arg Ser Ser Glu Gly
            770               775               780

Asp Cys Phe Ile Ala Leu Glu Gly Ser Tyr Val Glu Asn Ser Ser Thr
785                790               795               800

Ile Phe Ser Ser Val Ser Ile Val Lys Glu
            805               810

<210> SEQ ID NO 20
<211> LENGTH: 2433
<212> TYPE: DNA
<213> ORGANISM: Artificial
<220> FEATURE:
<223> OTHER INFORMATION: A synthetic nucleotide sequence representing a
     recombinant polynucleotide derived from a TIC2160 gene encoding a
     TIC2160 variant protein (Variant-a-145).

<400> SEQUENCE: 20

```
atgggcagca gccatcatca tcatcatcac cacatgattg tggataatac aaaattagat      60
acaagagctt taccaagctt tattgattat tttaacggta tttatggatt tgccactggt     120
atcaaagata ttatgggaat gattttttaaa acagatacag gttctagtaa tttaacatta     180
gatgagattt taaagaatca aaatttacta atgatatct cgtctaagct cgatggtatt     240
aatgaacat taggtgatct tattgcacaa gggaacttaa attcagaatt agctaaggaa     300
ttgctaaaaa tttctaatga gcagaatcag atgttaaatc atgttaatgc tcaacttaat     360
gcaatcaatt caacacttaa tgtatatctt cccaaaatta catctatgtt aaatgaggtg     420
atgatgcaaa accatgtttt aagtctacaa atagaatttc taagtaaaca attgcaagaa     480
atttcagata aacttgatat tatcaactta acgtactga ttaactctac attgacagag     540
attactcctg cttatcaacg tattaaatat gttaacgaaa aatttgatga attgacttct     600
actgtagatt ctcgtggtcg ttcttatcaa gataacgtta ctaaagaagt tattaatgaa     660
ttaactgatc taactgaatt ggccaaaagt gttacaaaaa atgatatgga tagttttgaa     720
ttttatcttc aaactttcca tgatgtaatg actggaaata atttatttgg taaatcagca     780
ttacgtactg ctgcacaatt aatcacaaaa aatgaaacag taacaagagg aagtgagata     840
ggaaaagttt ataatttctt gattgtttta acttctttac aagcaaaagc ttttctcact     900
ttaactgcat gtcgaaagtt attgggttta acagatattg attatactaa aactatgaat     960
cagcatttag atggacaaaa aagagaattt cgtattaata ttcttccaac actttctaat    1020
```

-continued

```
agtttttcta atcctagtta ttcaaagaat agaggaagtg atatcgatga tccaattgtt      1080
gtgttagaag cagcacctgg atatgcctta ataggatttc aaattctaaa cgatccactt      1140 ccgatttaa aaggatatca ggctaggtta aaaccaaatt atcaagttga cagagagtcg       1200
atgtcagaaa caatttatgg ggatattcat aaattatttt gtccaaaaca gctggagcaa      1260
aaatattata ttaaagatat tgaatttcct gaaggctatg taatcactaa aatcgtgttt      1320
gaaaaaaggc taaatcaatt gggttatgag gtaacggcaa attttatga cccctctaca      1380 ggaaacatcg atttaaacaa ggttaaagta gaatcttgga aggaaaagtc ttgcgaggag      1440
gaatcctgcg aagatgagtt ctgcgaacat gagtatagcc ttataaaggc tgaaacggat      1500
ggtatttata tgccattagg tgtagtaagt gagacctttt taaccccaat ttatggtttt      1560
ggattaacag ttgacgaaaa aaatcaaaaa ataactttaa caggtaaatc ctatttacgt      1620
gaatccttac tagaaacaga tttagttaac aatgaaacat atttaattgc ttcaccagac      1680
ggttatttta gtagtattgt agaaaattgg aatataacat cagataattt tggatcttgg      1740
agagcaaata ataataatgc atttgtcgat aaggaagata ctgtaaaagg atcaagttct      1800
ctgtatactc ataaagatgg ggaattctcg caatttattg gaaataagct aaaacctaaa      1860
actaattatg ttattcaata tgctataaaa ggaagacccg ctatttattt aaaaaataat      1920
aaggataact tgtttgagga taccaataac aactttagcg attttcagac tgtaacaaaa      1980
aaattcaatt caggagcaaa tccttcggaa atttatttgc ttttaaaaa tcaaggtgaa       2040 tacgaggctt gggggaataa ctttattatt ttagaaatta aatcgcttga attattgccg      2100
caaatgttga aacctgagga ttggatacca tcaggaaatg tgcaaatgaa agacgaagga      2160
cgcctagaga ttttaggaga tggctatttt aaacaattca ttaaattgca aaatgattca      2220
acctatcatc taagattatc agttaaggga accggtaggg tatcaataat tgatgaatct      2280
aactatttat tttttgtaaa tattaaggat gaagattta ctagcgttat taaaaatagg       2340
tcttcagaag gtgattgttt tatagctctt gagggttctt atgtagaaaa ttctagtacc      2400
attttttcta gtgtatctat cgttaaagaa tag                                   2433
```

<210> SEQ ID NO 21
<211> LENGTH: 810
<212> TYPE: PRT
<213> ORGANISM: Artificial
<220> FEATURE:
<223> OTHER INFORMATION: An amino acid sequence of a TIC2160 variant
    protein (Variant-a-145) encoded by SEQ ID NO: 20.

<400> SEQUENCE: 21

```
Met Gly Ser Ser His His His His His His Met Ile Val Asp Asn
1               5                  10                  15

Thr Lys Leu Asp Thr Arg Ala Leu Pro Ser Phe Ile Asp Tyr Phe Asn
            20                  25                  30

Gly Ile Tyr Gly Phe Ala Thr Gly Ile Lys Asp Ile Met Gly Met Ile
        35                  40                  45

Phe Lys Thr Asp Thr Gly Ser Ser Asn Leu Thr Leu Asp Glu Ile Leu
    50                  55                  60

Lys Asn Gln Asn Leu Leu Asn Asp Ile Ser Ser Lys Leu Asp Gly Ile
65                  70                  75                  80

Asn Gly Thr Leu Gly Asp Leu Ile Ala Gln Gly Asn Leu Asn Ser Glu
                85                  90                  95

Leu Ala Lys Glu Leu Leu Lys Ile Ser Asn Glu Gln Asn Gln Met Leu
```

```
                100                 105                 110
Asn His Val Asn Ala Gln Leu Asn Ala Ile Asn Ser Thr Leu Asn Val
            115                 120                 125

Tyr Leu Pro Lys Ile Thr Ser Met Leu Asn Glu Val Met Met Gln Asn
130                 135                 140

His Val Leu Ser Leu Gln Ile Glu Phe Leu Ser Lys Gln Leu Gln Glu
145                 150                 155                 160

Ile Ser Asp Lys Leu Asp Ile Ile Asn Leu Asn Val Leu Ile Asn Ser
                165                 170                 175

Thr Leu Thr Glu Ile Thr Pro Ala Tyr Gln Arg Ile Lys Tyr Val Asn
            180                 185                 190

Glu Lys Phe Asp Glu Leu Thr Ser Thr Val Asp Ser Arg Gly Arg Ser
        195                 200                 205

Tyr Gln Asp Asn Val Thr Lys Glu Val Ile Asn Glu Leu Thr Asp Leu
    210                 215                 220

Thr Glu Leu Ala Lys Ser Val Thr Lys Asn Asp Met Asp Ser Phe Glu
225                 230                 235                 240

Phe Tyr Leu Gln Thr Phe His Asp Val Met Thr Gly Asn Asn Leu Phe
                245                 250                 255

Gly Lys Ser Ala Leu Arg Thr Ala Ala Gln Leu Ile Thr Lys Asn Glu
            260                 265                 270

Thr Val Thr Arg Gly Ser Glu Ile Gly Lys Val Tyr Asn Phe Leu Ile
        275                 280                 285

Val Leu Thr Ser Leu Gln Ala Lys Ala Phe Leu Thr Leu Thr Ala Cys
    290                 295                 300

Arg Lys Leu Leu Gly Leu Thr Asp Ile Asp Tyr Thr Lys Thr Met Asn
305                 310                 315                 320

Gln His Leu Asp Gly Gln Lys Arg Glu Phe Arg Ile Asn Ile Leu Pro
                325                 330                 335

Thr Leu Ser Asn Ser Phe Ser Asn Pro Ser Tyr Ser Lys Asn Arg Gly
            340                 345                 350

Ser Asp Ile Asp Asp Pro Ile Val Val Leu Glu Ala Ala Pro Gly Tyr
        355                 360                 365

Ala Leu Ile Gly Phe Gln Ile Leu Asn Asp Pro Leu Pro Ile Leu Lys
    370                 375                 380

Gly Tyr Gln Ala Arg Leu Lys Pro Asn Tyr Gln Val Asp Arg Glu Ser
385                 390                 395                 400

Met Ser Glu Thr Ile Tyr Gly Asp Ile His Lys Leu Phe Cys Pro Lys
                405                 410                 415

Gln Leu Glu Gln Lys Tyr Tyr Ile Lys Asp Ile Glu Phe Pro Glu Gly
            420                 425                 430

Tyr Val Ile Thr Lys Ile Val Phe Glu Lys Arg Leu Asn Gln Leu Gly
        435                 440                 445

Tyr Glu Val Thr Ala Asn Phe Tyr Asp Pro Ser Thr Gly Asn Ile Asp
    450                 455                 460

Leu Asn Lys Val Lys Val Glu Ser Trp Lys Glu Lys Ser Cys Glu Glu
465                 470                 475                 480

Glu Ser Cys Glu Asp Glu Phe Cys Glu His Gly Tyr Ser Leu Ile Lys
                485                 490                 495

Ala Glu Thr Asp Gly Ile Tyr Met Pro Leu Gly Val Val Ser Glu Thr
            500                 505                 510

Phe Leu Thr Pro Ile Tyr Gly Phe Gly Leu Thr Val Asp Glu Lys Asn
        515                 520                 525
```

```
Gln Lys Ile Thr Leu Thr Gly Lys Ser Tyr Leu Arg Glu Ser Leu Leu
        530                 535                 540
Glu Thr Asp Leu Val Asn Asn Glu Thr Tyr Leu Ile Ala Ser Pro Asp
545                 550                 555                 560
Gly Tyr Phe Ser Ser Ile Val Glu Asn Trp Asn Ile Thr Ser Asp Asn
                565                 570                 575
Phe Gly Ser Trp Arg Ala Asn Asn Asn Ala Phe Val Asp Lys Glu
            580                 585                 590
Asp Thr Val Lys Gly Ser Ser Leu Tyr Thr His Lys Asp Gly Glu
        595                 600                 605
Phe Ser Gln Phe Ile Gly Asn Lys Leu Lys Pro Lys Thr Asn Tyr Val
610                 615                 620
Ile Gln Tyr Ala Ile Lys Gly Arg Pro Ala Ile Tyr Leu Lys Asn Asn
625                 630                 635                 640
Lys Asp Thr Leu Phe Glu Asp Thr Asn Asn Asn Phe Ser Asp Phe Gln
                645                 650                 655
Thr Val Thr Lys Lys Phe Asn Ser Gly Ala Asn Pro Ser Glu Ile Tyr
            660                 665                 670
Leu Leu Phe Lys Asn Gln Gly Glu Tyr Glu Ala Trp Gly Asn Asn Phe
        675                 680                 685
Ile Ile Leu Glu Ile Lys Ser Leu Glu Leu Leu Pro Gln Met Leu Lys
690                 695                 700
Pro Glu Asp Trp Ile Pro Ser Gly Asn Val Gln Met Lys Asp Glu Gly
705                 710                 715                 720
Arg Leu Glu Ile Leu Gly Asp Gly Tyr Phe Lys Gln Phe Ile Lys Leu
                725                 730                 735
Gln Asn Asp Ser Thr Tyr His Leu Arg Leu Ser Val Lys Gly Thr Gly
            740                 745                 750
Arg Val Ser Ile Ile Asp Glu Ser Asn Tyr Leu Phe Phe Val Asn Ile
        755                 760                 765
Lys Asp Glu Asp Phe Thr Ser Val Ile Lys Asn Arg Ser Ser Glu Gly
770                 775                 780
Asp Cys Phe Ile Ala Leu Glu Gly Ser Tyr Val Glu Asn Ser Ser Thr
785                 790                 795                 800
Ile Phe Ser Ser Val Ser Ile Val Lys Glu
                805                 810

<210> SEQ ID NO 22
<211> LENGTH: 2400
<212> TYPE: DNA
<213> ORGANISM: Artificial
<220> FEATURE:
<223> OTHER INFORMATION: A synthetic nucleotide sequence designed for
      expression in a plant cell and encodes the TIC2160 variant,
      TIC2160_13

<400> SEQUENCE: 22
atgcagcgca tgatcatcgt ggacaacaac aagctgaacg tcagggccct cccgagcttc      60
atcgactact tcaacggcat ctacggcttc gccaccggca tcaaggacat catgggcatg     120
atcttcaaga ctgacaccgg cggtagcaac ctcacccctc gacgagatcct caagaaccag    180 aacctcctca cgacatctc cggcaagctc gacggcatca acggcgacct cggcgacctc      240
atcgcccagg gcaacctcaa ctccgagctg gccaaggagc tgctcaagat ctccaacgag    300
cagaaccaga tgctcaacca cgtgaacgcc cagctcaacg ccatcaactc caccctcaac    360
```

| | | |
|---|---|---|
| atctacctcc cgaagatcac ctcgatgctc aacgaggtca tgaagcagaa ccacgtgctc | 420 | |
| tccctccaga tcgagttcct ctccaagcag ctccaggaga tcagcgacaa gctcgacatc | 480 | |
| attaacctca acgtgctcat caactccacc ctcaccgaga tcactccggc ctaccagcgc | 540 | |
| atcaagtacg tgaacgagaa gttcgacgag ctgacctcca ccgtggagaa gaacccgaag | 600 | |
| tcctaccagg acaacgtgac caaggaggtc atcgagaacc tcaacgagct gaccgagctg | 660 | |
| gccaagtccg tgaccaagaa cgacatggac tccttcgagt cctacctcca gaccttccac | 720 | |
| gacgtgatga ccggcaacaa tctgttcggc cgctccgccc tcaagaccgc ctccgaactc | 780 | |
| atcaccaagg agaacgtgac cacccgtggc tccgagatcg gcaaggtgta caacttcctg | 840 | |
| atcgtgctga cctccctgca agccaaggct ttcctgaccc tgaccgcttg ccgcaagctg | 900 | |
| cttggcctga ccgacatcga ctacactcag atcatgaacc accacatcga cggccagaag | 960 | |
| cgcgagttcc gcatcaacat cctgcccact ctgagcaaca acttcagcaa cccgagctac | 1020 | |
| agcaagaacc gtggcagcga catcgacgac cccatcgtgg tcctggaggc tgcgcctggc | 1080 | |
| tacgctctga tcggcttcga gatcctgaac gaccctctgc ctatcctcaa gggctaccag | 1140 | |
| gctaggctca agccgaacta ccaagtggac cgggagagca tgagcgagac tatctacggt | 1200 | |
| gacatccaca agctgttctg cccgagagaa ctggagcaga agtactacat cagaaacatc | 1260 | |
| gatttcccgg agggttacgt catcaccaag atcgtcttcg agaagcggct gaaccagctt | 1320 | |
| ggttacgagg tcactgctaa cttctacgac ccgagcactg gtagcatcga cctgaacaag | 1380 | |
| gtcaaggtcg agagctggga aaagagaact tctgatcaag acggttctga tgaccaagaa | 1440 | |
| tacagcatca tcaaggcgga gactgatggc atctacatgc cgcttggtgt cgtaagtgag | 1500 | |
| actttcctca ctccgatcta cggcttcggt ctcactgtcg atgagaagaa ccagaagatt | 1560 | |
| actctcacgg gcaagtctta ccttcgggag tctctcctgg agacggatct cctcaacaat | 1620 | |
| gagacgtacc ttattgcgtc tccggacggg tacatcagtt ccattgtcga gaactggaac | 1680 | |
| atcacgtctg acaacacggg ctcttggcgt gcgaacaata acaatgcgtt cgtcgataag | 1740 | |
| gcagatacga tcaagggctc ttcgtctctt tacacgcata aggatggcga gttctctcag | 1800 | |
| ttcattggga acaagctcaa gccgaagacg aactatgtca ttcagtacgt catcaagggt | 1860 | |
| cgtccagcca tctatcttaa gaataacaag gacacgctct cgaggatac gaagaataac | 1920 | |
| ttctcggact ccagactgt caccaagaag ttcaattcgg tgtcaatcc atcggaaatc | 1980 | |
| tactttctct tcaagaatca gtcggagtat gaggcgtggg ggaacaactt catcatcctt | 2040 | |
| gagatcaagt cgctggagtt cttgccacag atgctcaagc cagaggactg gattccctcg | 2100 | |
| ggcaatgtcc aaatgaagga tggaggacgt ctggaaatct tgggagatgg atacttcaaa | 2160 | |
| cagttcatca aactggagaa tgattcaacc taccatctaa gactatcagt caaagggaca | 2220 | |
| gggcgggttt caatcatcga cgagtcaaag tacctactgt tcgtgaatgt caaagacgaa | 2280 | |
| gacctcacac gagtcatcaa gaacactagc tcaaagggag agtgcttcat agcactcgaa | 2340 | |
| ggcacctacg tcgagaacag cagtaccatc ttcagtaatg tgtccatcgt caaggagtga | 2400 | |

<210> SEQ ID NO 23
<211> LENGTH: 799
<212> TYPE: PRT
<213> ORGANISM: Artificial
<220> FEATURE:
<223> OTHER INFORMATION: An amino acid sequence of the TIC2160 variant,
       TIC2160_13 encoded by SEQ ID NO: 22.

<400> SEQUENCE: 23

```
Met Gln Arg Met Ile Ile Val Asp Asn Asn Lys Leu Asn Val Arg Ala
  1               5                  10                  15

Leu Pro Ser Phe Ile Asp Tyr Phe Asn Gly Ile Tyr Gly Phe Ala Thr
             20                  25                  30

Gly Ile Lys Asp Ile Met Gly Met Ile Phe Lys Thr Asp Thr Gly Gly
             35                  40                  45

Ser Asn Leu Thr Leu Asp Glu Ile Leu Lys Asn Gln Asn Leu Leu Asn
 50                  55                  60

Asp Ile Ser Gly Lys Leu Asp Gly Ile Asn Asp Leu Gly Asp Leu
 65                  70                  75                  80

Ile Ala Gln Gly Asn Leu Asn Ser Glu Leu Ala Lys Glu Leu Leu Lys
                 85                  90                  95

Ile Ser Asn Glu Gln Asn Gln Met Leu Asn His Val Asn Ala Gln Leu
                100                 105                 110

Asn Ala Ile Asn Ser Thr Leu Asn Ile Tyr Leu Pro Lys Ile Thr Ser
             115                 120                 125

Met Leu Asn Glu Val Met Lys Gln Asn His Val Leu Ser Leu Gln Ile
         130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
                 165                 170                 175

Ala Tyr Gln Arg Ile Lys Tyr Val Asn Glu Lys Phe Asp Glu Leu Thr
             180                 185                 190

Ser Thr Val Glu Lys Asn Pro Lys Ser Tyr Gln Asp Asn Val Thr Lys
             195                 200                 205

Glu Val Ile Glu Asn Leu Asn Glu Leu Thr Glu Leu Ala Lys Ser Val
         210                 215                 220

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
                 245                 250                 255

Ala Ser Glu Leu Ile Thr Lys Glu Asn Val Thr Thr Arg Gly Ser Glu
             260                 265                 270

Ile Gly Lys Val Tyr Asn Phe Leu Ile Val Leu Thr Ser Leu Gln Ala
         275                 280                 285

Lys Ala Phe Leu Thr Leu Thr Ala Cys Arg Lys Leu Leu Gly Leu Thr
         290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
             325                 330                 335

Asn Pro Ser Tyr Ser Lys Asn Arg Gly Ser Asp Ile Asp Asp Pro Ile
             340                 345                 350

Val Val Leu Glu Ala Ala Pro Gly Tyr Ala Leu Ile Gly Phe Glu Ile
         355                 360                 365

Leu Asn Asp Pro Leu Pro Ile Leu Lys Gly Tyr Gln Ala Arg Leu Lys
         370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Arg Glu Leu Glu Gln Lys Tyr Tyr
             405                 410                 415

Ile Arg Asn Ile Asp Phe Pro Glu Gly Tyr Val Ile Thr Lys Ile Val
```

```
                420            425            430
Phe Glu Lys Arg Leu Asn Gln Leu Gly Tyr Glu Val Thr Ala Asn Phe
            435                440                445

Tyr Asp Pro Ser Thr Gly Ser Ile Asp Leu Asn Lys Val Lys Val Glu
450                455                460

Ser Trp Glu Lys Arg Thr Ser Asp Gln Asp Gly Ser Asp Asp Gln Glu
465                470                475                480

Tyr Ser Ile Ile Lys Ala Glu Thr Asp Gly Ile Tyr Met Pro Leu Gly
            485                490                495

Val Val Ser Glu Thr Phe Leu Thr Pro Ile Tyr Gly Phe Gly Leu Thr
            500                505                510

Val Asp Glu Lys Asn Gln Lys Ile Thr Leu Thr Gly Lys Ser Tyr Leu
            515                520                525

Arg Glu Ser Leu Leu Glu Thr Asp Leu Leu Asn Glu Thr Tyr Leu
            530                535                540

Ile Ala Ser Pro Asp Gly Tyr Ile Ser Ser Ile Val Glu Asn Trp Asn
545                550                555                560

Ile Thr Ser Asp Asn Thr Gly Ser Trp Arg Ala Asn Asn Asn Ala
                565                570                575

Phe Val Asp Lys Ala Asp Thr Ile Lys Gly Ser Ser Leu Tyr Thr
                580                585                590

His Lys Asp Gly Glu Phe Ser Gln Phe Ile Gly Asn Lys Leu Lys Pro
            595                600                605

Lys Thr Asn Tyr Val Ile Gln Tyr Val Ile Lys Gly Arg Pro Ala Ile
            610                615                620

Tyr Leu Lys Asn Asn Lys Asp Thr Leu Phe Glu Asp Thr Lys Asn Asn
625                630                635                640

Phe Ser Asp Phe Gln Thr Val Thr Lys Lys Phe Asn Ser Gly Val Asn
                645                650                655

Pro Ser Glu Ile Tyr Phe Leu Phe Lys Asn Gln Ser Glu Tyr Glu Ala
                660                665                670

Trp Gly Asn Asn Phe Ile Ile Leu Glu Ile Lys Ser Leu Glu Phe Leu
            675                680                685

Pro Gln Met Leu Lys Pro Glu Asp Trp Ile Pro Ser Gly Asn Val Gln
            690                695                700

Met Lys Asp Gly Gly Arg Leu Glu Ile Leu Gly Asp Gly Tyr Phe Lys
705                710                715                720

Gln Phe Ile Lys Leu Glu Asn Asp Ser Thr Tyr His Leu Arg Leu Ser
                725                730                735

Val Lys Gly Thr Gly Arg Val Ser Ile Ile Asp Glu Ser Lys Tyr Leu
                740                745                750

Leu Phe Val Asn Val Lys Asp Glu Asp Leu Thr Arg Val Ile Lys Asn
            755                760                765

Thr Ser Ser Lys Gly Glu Cys Phe Ile Ala Leu Glu Gly Thr Tyr Val
770                775                780

Glu Asn Ser Ser Thr Ile Phe Ser Asn Val Ser Ile Val Lys Glu
785                790                795
```

<210> SEQ ID NO 24
<211> LENGTH: 2397
<212> TYPE: DNA
<213> ORGANISM: Artificial
<220> FEATURE:
<223> OTHER INFORMATION: A synthetic nucleotide sequence designed for expression in a plant cell and encodes the TIC2160 variant,

TIC2160_14.

<400> SEQUENCE: 24

```
atgcagcgca tgatcatcgt ggacaacaac aagctgaacg tcagggccct cccgagcttc      60
atcgactact tcaacggcat ctacggcttc gccaccggca tcaaggacat catgggcatg     120
atcttcaaga ctgacaccgg cggtagcaac ctcaccctcg acgagatcct caagaaccag     180
aacctcctca cgacatctc cggcaagctc gacggcatca acggcgacct cggcgacctc     240
atcgcccagg gcaacctcaa ctccgagctg gccaaggagc tgctcaagat ctccaacgag     300
cagaaccaga tgctcaacca cgtgaacgcc cagctcaacg ccatcaactc caccctcaac     360
atctacctcc cgaagatcac ctcgatgctc aacgaggtca tgaagcagaa ccacgtgctc     420
tccctccaga tcgagttcct ctccaagcag ctccaggaga tcagcgacaa gctcgacatc     480
attaacctca acgtgctcat caactccacc ctcaccgaga tcactccggc ctaccagcgc     540
atcaagtacg tgaacgagaa gttcgacgag ctgacctcca ccgtggagag accaggtgct     600
aagagaagag acccaggttc tagacaactt cttgagaacc tcaacgagct gaccgagctg     660
gccaagtccg tgaccaagaa cgacatggac tccttcgagt tctacctcca gaccttccac     720
gacgtgatga ccgcaacaa tctgttcggc cgctccgccc tcaagaccgc ctccgaactc     780
atcaccaagg agaacgtgac cacccgtggc tccgagatcg gcaaggtgta caacttcctg     840
atcgtgctga cctccctgca agccaaggct ttcctgaccc tgaccgcttg ccgcaagctg     900
cttggcctga ccgacatcga ctacactcag atcatgaacc accacatcga cggccagaag     960
cgcgagttcc gcatcaacat cctgcccact ctgagcaaca acttcagcaa cccgagctac    1020
agcaagaacc gtggcagcga catcgacgac cccatcgtgg tcctggaggc tgcgcctggc    1080
tacgctctga tcggcttcga gatcctgaac gaccctctgc ctatcctcaa gggctaccag    1140
gctaggctca agccgaacta ccaagtggac cgggagagca tgagcgagac tatctacggt    1200
gacatccaca gctgttctg cccgaagcaa ctggagcaga agtactacat caaggacatc    1260
gagttcccgg agggttacgt catcaccaag atcgtcttcg agaagcggct gaaccagctt    1320
ggttacgagg tcactgctaa cttctacgac ccgagcactg gtagcatcga cctgaacaag    1380
gtcaaggtcg agagctggaa ggagaagtcc tgcgaggaag actcttgcga ggacgagtac    1440
agcatcatca aggcggagac tgatggcatc tacatgccgc ttggtgtcgt aagtgagact    1500
ttcctcactc cgatctacgg cttcggtctc actgtcgatg agaagaacca gaagattact    1560
ctcacgggca gtcttacct tcgggagtct ctcctggaga cggatctcct caacaatgag    1620
acgtaccta ttgcgtctcc ggacgggtac atcagttcca ttgtcgagaa ctggaacatc    1680
acgtctgaca cacgggctc ttggcgtgcg aacaataaca atgcgttcgt cgataaggca    1740
gatacgatca agggctcttc gtctctttac acgcataagg atggcgagtt ctctcagttc    1800
attgggaaca agctcaagcc gaagacgaac tatgtcattc agtacgtcat caagggtcgt    1860
ccagccatct atcttaagaa taacaaggac acgctcttcg aggatacgaa gaataacttc    1920
tcggacttcc agactgtcac caagaagttc aattcgggtg tcaatccatc ggaaatctac    1980
tttctcttca agaatcagtc ggagtatgag gcgtgggga acaacttcat catccttgag    2040
atcaagtcgc tggagttctt gccacagatg ctcaagccag aggactggat ccctcgggc    2100
aatgtccaaa tgaaggatgg aggacgtctg gaaatcttgg gagatggata cttcaaacag    2160
ttcatcaaac tgaccaatc tgattcttac catctaagac tatcagtcaa agggacaggg    2220
cgggtttcaa tcatcgacga gtcaaagtac ctactgttcg tgaatgtcaa agacgaagac    2280
```

```
ctcacacgag tcatcaagaa cactagctca aagggagagt gcttcatagc actcgaaggc    2340
acctacgtcg agaacagcag taccatcttc agtaatgtgt ccatcgtcaa ggagtga       2397
```

<210> SEQ ID NO 25
<211> LENGTH: 798
<212> TYPE: PRT
<213> ORGANISM: Artificial
<220> FEATURE:
<223> OTHER INFORMATION: An amino acid sequence of the TIC2160 variant,
      TIC2160_14 encoded by SEQ ID NO: 24.

<400> SEQUENCE: 25

```
Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
            20                  25                  30

Gly Ile Lys Asp Ile Met Gly Met Ile Phe Lys Thr Asp Thr Gly Gly
        35                  40                  45

Ser Asn Leu Thr Leu Asp Glu Ile Leu Lys Asn Gln Asn Leu Leu Asn
    50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
    130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
                165                 170                 175

Ala Tyr Gln Arg Ile Lys Tyr Val Asn Glu Lys Phe Asp Glu Leu Thr
            180                 185                 190

Ser Thr Val Glu Arg Pro Gly Ala Lys Arg Arg Asp Pro Gly Ser Arg
        195                 200                 205

Gln Leu Leu Glu Asn Leu Asn Glu Leu Thr Glu Leu Ala Lys Ser Val
    210                 215                 220

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
                245                 250                 255

Ala Ser Glu Leu Ile Thr Lys Glu Asn Val Thr Thr Arg Gly Ser Glu
            260                 265                 270

Ile Gly Lys Val Tyr Asn Phe Leu Ile Val Leu Thr Ser Leu Gln Ala
        275                 280                 285

Lys Ala Phe Leu Thr Leu Thr Ala Cys Arg Lys Leu Leu Gly Leu Thr
    290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
                325                 330                 335
```

```
Asn Pro Ser Tyr Ser Lys Asn Arg Gly Ser Asp Ile Asp Pro Ile
            340                 345                 350

Val Val Leu Glu Ala Ala Pro Gly Tyr Ala Leu Ile Gly Phe Glu Ile
        355                 360                 365

Leu Asn Asp Pro Leu Pro Ile Leu Lys Gly Tyr Gln Ala Arg Leu Lys
    370                 375                 380

Pro Asn Tyr Gln Val Asp Arg Glu Ser Met Ser Thr Ile Tyr Gly
385                 390                 395                 400

Asp Ile His Lys Leu Phe Cys Pro Lys Gln Leu Glu Gln Lys Tyr Tyr
                405                 410                 415

Ile Lys Asp Ile Glu Phe Pro Glu Gly Tyr Val Ile Thr Lys Ile Val
            420                 425                 430

Phe Glu Lys Arg Leu Asn Gln Leu Gly Tyr Glu Val Thr Ala Asn Phe
            435                 440                 445

Tyr Asp Pro Ser Thr Gly Ser Ile Asp Leu Asn Lys Val Lys Val Glu
    450                 455                 460

Ser Trp Lys Glu Lys Ser Cys Glu Glu Asp Ser Cys Glu Asp Glu Tyr
465                 470                 475                 480

Ser Ile Ile Lys Ala Glu Thr Asp Gly Ile Tyr Met Pro Leu Gly Val
                485                 490                 495

Val Ser Glu Thr Phe Leu Thr Pro Ile Tyr Gly Phe Gly Leu Thr Val
            500                 505                 510

Asp Glu Lys Asn Gln Lys Ile Thr Leu Thr Gly Lys Ser Tyr Leu Arg
            515                 520                 525

Glu Ser Leu Leu Glu Thr Asp Leu Leu Asn Asn Glu Thr Tyr Leu Ile
530                 535                 540

Ala Ser Pro Asp Gly Tyr Ile Ser Ser Ile Val Glu Asn Trp Asn Ile
545                 550                 555                 560

Thr Ser Asp Asn Thr Gly Ser Trp Arg Ala Asn Asn Asn Ala Phe
                565                 570                 575

Val Asp Lys Ala Asp Thr Ile Lys Gly Ser Ser Leu Tyr Thr His
            580                 585                 590

Lys Asp Gly Glu Phe Ser Gln Phe Ile Gly Asn Lys Leu Lys Pro Lys
            595                 600                 605

Thr Asn Tyr Val Ile Gln Tyr Val Ile Lys Gly Arg Pro Ala Ile Tyr
    610                 615                 620

Leu Lys Asn Asn Lys Asp Thr Leu Phe Glu Asp Thr Lys Asn Asn Phe
625                 630                 635                 640

Ser Asp Phe Gln Thr Val Thr Lys Lys Phe Asn Ser Gly Val Asn Pro
                645                 650                 655

Ser Glu Ile Tyr Phe Leu Phe Lys Asn Gln Ser Glu Tyr Glu Ala Trp
                660                 665                 670

Gly Asn Asn Phe Ile Ile Leu Glu Ile Lys Ser Leu Glu Phe Leu Pro
            675                 680                 685

Gln Met Leu Lys Pro Glu Asp Trp Ile Pro Ser Gly Asn Val Gln Met
    690                 695                 700

Lys Asp Gly Gly Arg Leu Glu Ile Leu Gly Asp Gly Tyr Phe Lys Gln
705                 710                 715                 720

Phe Ile Lys Leu Asn Gln Ser Asp Ser Tyr His Leu Arg Leu Ser Val
                725                 730                 735

Lys Gly Thr Gly Arg Val Ser Ile Ile Asp Glu Ser Lys Tyr Leu Leu
            740                 745                 750

Phe Val Asn Val Lys Asp Glu Asp Leu Thr Arg Val Ile Lys Asn Thr
```

```
              755                 760                 765
Ser Ser Lys Gly Glu Cys Phe Ile Ala Leu Glu Gly Thr Tyr Val Glu
          770                 775                 780

Asn Ser Ser Thr Ile Phe Ser Asn Val Ser Ile Val Lys Glu
785                 790                 795
```

<210> SEQ ID NO 26
<211> LENGTH: 2397
<212> TYPE: DNA
<213> ORGANISM: Artificial
<220> FEATURE:
<223> OTHER INFORMATION: A synthetic nucleotide sequence designed for
      expression in a plant cell and encodes the TIC2160 variant,
      TIC2160_15.

<400> SEQUENCE: 26

```
atgcagcgca tgatcatcgt ggacaacaac aagctgaacg tcagggccct cccgagcttc      60
atcgactact tcaacggcat ctacggcttc gccaccggca tcaaggacat catgggcatg     120
atcttcaaga ctgacaccgg cggtagcaac ctcaccctcg acgagatcct caagaaccag     180
aacctcctca cgacatctc cggcaagctc gacggcatca cggcgaccct cggcgacctc     240
atcgcccagg caacctcaa ctccgagctg ccaaggagc tgctcaagat ctccaacgag     300
cagaaccaga tgctcaacca cgtgaacgcc cagctcaacg ccatcaactc caccctcaac     360
atctacctcc cgaagatcac ctcgatgctc aacgaggtca tgaagcagaa ccacgtgctc     420
tccctccaga tcgagttcct ctccaagcag ctccaggaga tcagcgacaa gctcgacatc     480
attaacctca cgtgctcat caactccacc ctcaccgaga tcactccggc ctaccagcgc     540
atcaagtacg tgaacgagaa gttcgacgag ctgacctcca ccgtggagag accaggtgct     600
aagagaagag acccaggttc tagacaactt cttgagaacc tcaacgagct gaccgagctg     660
gccaagtccg tgaccaagaa cgacatggac tccttcgagt tctacctcca gaccttccac     720
gacgtgatga ccggcaacaa tctgttcggc cgctccgccc tcaagaccgc ctccgaactc     780
atcaccagaa cgaaactgt acccgtggc tcccaaatcg gcaaggtgta caacttcctg     840
atcgtgctga cctccctgca agccaaggct ttcctgaccc tgaccgcttg ccgcaagctg     900
cttggcctga ccgacatcga ctacactcag atcatgaacc accacatcga cggccagaag     960
cgcgagttcc gcatcaacat cctgcccact ctgagcaaca acttcagcaa cccgagctac    1020
agcaagaacc gtggcagcga catcgacgac cccatcgtgg tcctggaggc tgcgcctggc    1080
tacgctctga tcggcttcga gatcctgaac gaccctctgc ctatcctcaa gggctaccag    1140
gctaggctca agccgaacta ccaagtggac cgggagagca tgagcgagac tatctacggt    1200
gacatccaca gctgttctg cccgaagcaa ctggagcaga agtactacat caaggacatc    1260
gagttcccgg agggttacgt catcaccaag atcgtcttcg agaagcggct gaaccagctt    1320
ggttacgagg tcactgctaa cttctacgac ccgagcactg gtagcatcga cctgaacaag    1380
gtcaaggtcg agagctggaa ggagaagtcc tgcgaggaag actcttgcga ggacgagtac    1440
agcatcatca aggcggagac tgatggcatc tacatgccgc ttggtgtcgt aagtgagact    1500
ttcctcactc cgatctacgg cttcggtctc actgtcgatg agaagaacca gaagattact    1560
ctcacgggca gtcttacct tcgggagtct ctcctggaga cggatctcct caacaatgag    1620
acgtaccta ttgcgtctcc ggacgggtac atcagttcca ttgtcgagaa ctggaacatc    1680
acgtctgaca cacgggctc ttggcgtgcg aacaataaca atgcgttcgt cgataaggca    1740
gatacgatca agggctcttc gtctctttac acgcataagg atggcgagtt ctctcagttc    1800
```

```
attgggaaca agctcaagcc gaagacgaac tatgtcattc agtacgtcat caagggtcgt   1860
ccagccatct atcttaagaa taacaaggac acgctcttcg aggatacgaa gaataacttc   1920
tcggacttcc agactgtcac caagaagttc aattcgggtg tcaatccatc ggaaatctac   1980
tttctcttca agaatcagtc ggagtatgag gcgtggggga acaacttcat catccttgag   2040
atcaagtcgc tggagttctt gccacagatg ctcaagccag aggactggat tccctcgggc   2100
aatgtccaaa tgaaggatgg aggacgtctg gaaatcttgg gagatggata cttcaaacag   2160
ttcatcaaac tggagaatga ttcaacctac catctaagac tatcagtcaa agggacaggg   2220
cgggtttcaa tcatcgacga gtcaaagtac ctactgttcg tgaatgtcaa agacgaagac   2280
ctcacacgag tcatcaagaa cactagctca aagggagagt gcttcatagc actcgaaggc   2340
acctacgtcg agaacagcag taccatcttc agtaatgtgt ccatcgtcaa ggagtga      2397
```

<210> SEQ ID NO 27
<211> LENGTH: 798
<212> TYPE: PRT
<213> ORGANISM: Artificial
<220> FEATURE:
<223> OTHER INFORMATION: An amino acid sequence of the TIC2160 variant, TIC2160_15 encoded by SEQ ID NO: 26.

<400> SEQUENCE: 27

```
Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
            20                  25                  30

Gly Ile Lys Asp Ile Met Gly Met Ile Phe Lys Thr Asp Thr Gly Gly
        35                  40                  45

Ser Asn Leu Thr Leu Asp Glu Ile Leu Lys Asn Gln Asn Leu Leu Asn
    50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
    130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
                165                 170                 175

Ala Tyr Gln Arg Ile Lys Tyr Val Asn Glu Lys Phe Asp Glu Leu Thr
            180                 185                 190

Ser Thr Val Glu Arg Pro Gly Ala Lys Arg Arg Asp Pro Gly Ser Arg
        195                 200                 205

Gln Leu Leu Glu Asn Leu Asn Glu Leu Thr Glu Leu Ala Lys Ser Val
    210                 215                 220

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
                245                 250                 255
```

```
Ala Ser Glu Leu Ile Thr Arg Asn Glu Thr Val Thr Arg Gly Ser Gln
            260                 265                 270

Ile Gly Lys Val Tyr Asn Phe Leu Ile Val Leu Thr Ser Leu Gln Ala
            275                 280                 285

Lys Ala Phe Leu Thr Leu Thr Ala Cys Arg Lys Leu Leu Gly Leu Thr
            290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
            325                 330                 335

Asn Pro Ser Tyr Ser Lys Asn Arg Gly Ser Asp Ile Asp Pro Ile
            340                 345                 350

Val Val Leu Glu Ala Ala Pro Gly Tyr Ala Leu Ile Gly Phe Glu Ile
            355                 360                 365

Leu Asn Asp Pro Leu Pro Ile Leu Lys Gly Tyr Gln Ala Arg Leu Lys
            370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Lys Gln Leu Glu Gln Lys Tyr Tyr
            405                 410                 415

Ile Lys Asp Ile Glu Phe Pro Glu Gly Tyr Val Ile Thr Lys Ile Val
            420                 425                 430

Phe Glu Lys Arg Leu Asn Gln Leu Gly Tyr Glu Val Thr Ala Asn Phe
            435                 440                 445

Tyr Asp Pro Ser Thr Gly Ser Ile Asp Leu Asn Lys Val Lys Val Glu
            450                 455                 460

Ser Trp Lys Glu Lys Ser Cys Glu Glu Asp Ser Cys Glu Asp Glu Tyr
465                 470                 475                 480

Ser Ile Ile Lys Ala Glu Thr Asp Gly Ile Tyr Met Pro Leu Gly Val
            485                 490                 495

Val Ser Glu Thr Phe Leu Thr Pro Ile Tyr Gly Phe Gly Leu Thr Val
            500                 505                 510

Asp Glu Lys Asn Gln Lys Ile Thr Leu Thr Gly Lys Ser Tyr Leu Arg
            515                 520                 525

Glu Ser Leu Leu Glu Thr Asp Leu Leu Asn Asn Glu Thr Tyr Leu Ile
            530                 535                 540

Ala Ser Pro Asp Gly Tyr Ile Ser Ser Ile Val Glu Asn Trp Asn Ile
545                 550                 555                 560

Thr Ser Asp Asn Thr Gly Ser Trp Arg Ala Asn Asn Asn Asn Ala Phe
            565                 570                 575

Val Asp Lys Ala Asp Thr Ile Lys Gly Ser Ser Ser Leu Tyr Thr His
            580                 585                 590

Lys Asp Gly Glu Phe Ser Gln Phe Ile Gly Asn Lys Leu Lys Pro Lys
            595                 600                 605

Thr Asn Tyr Val Ile Gln Tyr Val Ile Lys Gly Arg Pro Ala Ile Tyr
            610                 615                 620

Leu Lys Asn Asn Lys Asp Thr Leu Phe Glu Asp Thr Lys Asn Asn Phe
625                 630                 635                 640

Ser Asp Phe Gln Thr Val Thr Lys Lys Phe Asn Ser Gly Val Asn Pro
            645                 650                 655

Ser Glu Ile Tyr Phe Leu Phe Lys Asn Gln Ser Glu Tyr Glu Ala Trp
            660                 665                 670
```

```
Gly Asn Asn Phe Ile Ile Leu Glu Ile Lys Ser Leu Glu Phe Leu Pro
            675                 680                 685

Gln Met Leu Lys Pro Glu Asp Trp Ile Pro Ser Gly Asn Val Gln Met
690                 695                 700

Lys Asp Gly Gly Arg Leu Glu Ile Leu Gly Asp Gly Tyr Phe Lys Gln
705                 710                 715                 720

Phe Ile Lys Leu Glu Asn Asp Ser Thr Tyr His Leu Arg Leu Ser Val
                725                 730                 735

Lys Gly Thr Gly Arg Val Ser Ile Ile Asp Glu Ser Lys Tyr Leu Leu
            740                 745                 750

Phe Val Asn Val Lys Asp Glu Asp Leu Thr Arg Val Ile Lys Asn Thr
        755                 760                 765

Ser Ser Lys Gly Glu Cys Phe Ile Ala Leu Glu Gly Thr Tyr Val Glu
    770                 775                 780

Asn Ser Ser Thr Ile Phe Ser Asn Val Ser Ile Val Lys Glu
785                 790                 795
```

<210> SEQ ID NO 28
<211> LENGTH: 2397
<212> TYPE: DNA
<213> ORGANISM: Artificial
<220> FEATURE:
<223> OTHER INFORMATION: A synthetic nucleotide sequence designed for expression in a plant cell and encodes the TIC2160 variant, TIC2160_16.

<400> SEQUENCE: 28

```
atgcagcgca tgatcatcgt ggacaacaac aagctgaacg tcagggccct cccgagcttc    60
atcgactact tcaacggcat ctacggcttc gccaccggca tcaaggacat catgggcatg   120
atcttcaaga ctgacaccgg cggtagcaac ctcacccctcg acgagatcct caagaaccag   180
aacctcctca cgacatctc cggcaagctc gacggcatca cggcgacct cggcgaccct    240
atcgcccagg caacctcaa ctccgagctg gccaaggagc tgctcaagat ctccaacgag   300
cagaaccaga tgctcaacca cgtgaacgcc cagctcaacg ccatcaactc caccctcaac   360
atctacctcc cgaagatcac ctcgatgctc aacgaggtca tgaagcagaa ccacgtgctc   420
tccctccaga tcgagttcct ctccaagcag ctccaggaga tcagcgacaa gctcgacatc   480
attaaccctca cgtgctcat caactccacc ctcaccgaga tcactccggc ctaccagcgc   540
atcaagtacg tgaacgagaa gttcgacgag ctgacctcca ccgtggagaa gaacccgaag   600
tcctaccagg acaacgtgac caaggaggtc atcgagaacc tcaacgagct gaccgagctg   660
gccaagtccg tgaccaagaa cgacatggac tccttcgagt tctacctcca gaccttccac   720
gacgtgatga ccggcaacaa tctgttcggc cgctccgccc tcaagaccgc ctccgaactc   780
atcaccagaa acgaaactgt taccgtggc tcccaaatcg gcaaggtgta caacttcctg   840
atcgtgctga cctccctgca agccaaggct ttcctgaccc tgaccgcttg ccgcaagctg   900
cttggcctga ccgacatcga ctacactcag atcatgaacc accacatcga cggccagaag   960
cgcgagttcc gcatcaacat cctgcccact ctgagcaaca acttcagcaa cccgagctac  1020
agcaagaacc gtggcagcga catcgacgac cccatcgtgg tcctggaggc tgcgcctggc  1080
tacgctctga tcggcttcga gatcctgaac gaccctctgc ctatcctcaa gggctaccag  1140
gctaggctca agccgaacta ccaagtggac cgggagagca tgagcgagac tatctacggt  1200
gacatccaca agctgttctg cccgaagcaa ctggagcaga gtactacat caaggacatc  1260
gagttccccgg agggttacgt catcaccaag atcgtcttcg agaagcggct gaaccagctt  1320
```

-continued

```
ggttacgagg tcactgctaa cttctacgac ccgagcactg gtagcatcga cctgaacaag   1380
gtcaaggtcg agagctggaa ggagaagtcc tgcgaggaag actcttgcga ggacgagtac   1440
agcatcatca aggcggagac tgatggcatc tacatgccgc ttggtgtcgt aagtgagact   1500
ttcctcactc cgatctacgg cttcggtctc actgtcgatg agaagaacca gaagattact   1560
ctcacgggca gtcttacct tcgggagtct ctcctggaga cggatctcct caacaatgag   1620 acgtaccta ttgcgtctcc ggacgggtac atcagttcca ttgtcgagaa ctggaacatc   1680
acgtctgaca cacgggctc ttggcgtgcg aacaataaca atgcgttcgt cgataaggca   1740
gatacgatca agggctcttc gtctctttac acgcataagg atggcgagtt ctctcagttc   1800
attgggaaca agctcaagcc gaagacgaac tatgtcattc agtacgtcat caagggtcgt   1860
ccagccatct atcttaagaa taacaaggac acgtcttcg aggatacgaa gataacttc    1920 tcggacttcc agactgtcac caagaagttc aattcgggtg tcaatccatc ggaaatctac   1980
tttctcttca gaatcagtc ggagtatgag gcgtggggga acaacttcat catccttgag   2040
atcaagtcgc tggagttctt gccacagatg ctcaagccag aggactggat tccctcgggc   2100
aatgtccaaa tgaaggatgg aggacgtctg gaaatcttgg gagatggata cttcaaacag   2160
ttcatcaaac tggagaatga ttcaacctac catctaagac tatcagtcaa agggacaggg   2220
cgggtttcaa tcatcgacga gtcaaagtac ctactgttcg tgaatgtcaa agacgaagac   2280
ctcacacgag tcatcaagaa cactagctca aagggagagt gcttcatagc actcgaaggc   2340
acctacgtcg agaacagcag taccatcttc agtaatgtgt ccatcgtcaa ggagtga      2397
```

```
<210> SEQ ID NO 29
<211> LENGTH: 798
<212> TYPE: PRT
<213> ORGANISM: Artificial
<220> FEATURE:
<223> OTHER INFORMATION: An amino acid sequence of the TIC2160 variant,
      TIC2160_16 encoded by SEQ ID NO: 28.

<400> SEQUENCE: 29

Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
            20                  25                  30

Gly Ile Lys Asp Ile Met Gly Met Ile Phe Lys Thr Asp Thr Gly Gly
        35                  40                  45

Ser Asn Leu Thr Leu Asp Glu Ile Leu Lys Asn Gln Asn Leu Leu Asn
    50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
    130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
```

```
            165                 170                 175
Ala Tyr Gln Arg Ile Lys Tyr Val Asn Glu Lys Phe Asp Glu Leu Thr
            180                 185                 190

Ser Thr Val Glu Lys Asn Pro Lys Ser Tyr Gln Asp Asn Val Thr Lys
            195                 200                 205

Glu Val Ile Glu Asn Leu Asn Glu Leu Thr Glu Leu Ala Lys Ser Val
210                 215                 220

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
            245                 250                 255

Ala Ser Glu Leu Ile Thr Arg Asn Glu Thr Val Thr Arg Gly Ser Gln
            260                 265                 270

Ile Gly Lys Val Tyr Asn Phe Leu Ile Val Leu Thr Ser Leu Gln Ala
            275                 280                 285

Lys Ala Phe Leu Thr Leu Thr Ala Cys Arg Lys Leu Leu Gly Leu Thr
            290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
            325                 330                 335

Asn Pro Ser Tyr Ser Lys Asn Arg Gly Ser Asp Ile Asp Pro Ile
            340                 345                 350

Val Val Leu Glu Ala Ala Pro Gly Tyr Ala Leu Ile Gly Phe Glu Ile
            355                 360                 365

Leu Asn Asp Pro Leu Pro Ile Leu Lys Gly Tyr Gln Ala Arg Leu Lys
370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Lys Gln Leu Glu Gln Lys Tyr Tyr
            405                 410                 415

Ile Lys Asp Ile Glu Phe Pro Glu Gly Tyr Val Ile Thr Lys Ile Val
            420                 425                 430

Phe Glu Lys Arg Leu Asn Gln Leu Gly Tyr Glu Val Thr Ala Asn Phe
            435                 440                 445

Tyr Asp Pro Ser Thr Gly Ser Ile Asp Leu Asn Lys Val Lys Val Glu
450                 455                 460

Ser Trp Lys Glu Lys Ser Cys Glu Glu Asp Ser Cys Glu Asp Glu Tyr
465                 470                 475                 480

Ser Ile Ile Lys Ala Glu Thr Asp Gly Ile Tyr Met Pro Leu Gly Val
            485                 490                 495

Val Ser Glu Thr Phe Leu Thr Pro Ile Tyr Gly Phe Gly Leu Thr Val
            500                 505                 510

Asp Glu Lys Asn Gln Lys Ile Thr Leu Thr Gly Lys Ser Tyr Leu Arg
            515                 520                 525

Glu Ser Leu Leu Glu Thr Asp Leu Leu Asn Asn Glu Thr Tyr Leu Ile
            530                 535                 540

Ala Ser Pro Asp Gly Tyr Ile Ser Ser Ile Val Glu Asn Trp Asn Ile
545                 550                 555                 560

Thr Ser Asp Asn Thr Gly Ser Trp Arg Ala Asn Asn Asn Ala Phe
            565                 570                 575

Val Asp Lys Ala Asp Thr Ile Lys Gly Ser Ser Ser Leu Tyr Thr His
            580                 585                 590
```

Lys Asp Gly Glu Phe Ser Gln Phe Ile Gly Asn Lys Leu Lys Pro Lys
                595                 600                 605

Thr Asn Tyr Val Ile Gln Tyr Val Ile Lys Gly Arg Pro Ala Ile Tyr
        610                 615                 620

Leu Lys Asn Asn Lys Asp Thr Leu Phe Glu Asp Thr Lys Asn Asn Phe
625                 630                 635                 640

Ser Asp Phe Gln Thr Val Thr Lys Lys Phe Asn Ser Gly Val Asn Pro
            645                 650                 655

Ser Glu Ile Tyr Phe Leu Phe Lys Asn Gln Ser Glu Tyr Glu Ala Trp
        660                 665                 670

Gly Asn Asn Phe Ile Ile Leu Glu Ile Lys Ser Leu Glu Phe Leu Pro
            675                 680                 685

Gln Met Leu Lys Pro Glu Asp Trp Ile Pro Ser Gly Asn Val Gln Met
    690                 695                 700

Lys Asp Gly Gly Arg Leu Glu Ile Leu Gly Asp Gly Tyr Phe Lys Gln
705                 710                 715                 720

Phe Ile Lys Leu Glu Asn Asp Ser Thr Tyr His Leu Arg Leu Ser Val
            725                 730                 735

Lys Gly Thr Gly Arg Val Ser Ile Ile Asp Glu Ser Lys Tyr Leu Leu
        740                 745                 750

Phe Val Asn Val Lys Asp Glu Asp Leu Thr Arg Val Ile Lys Asn Thr
            755                 760                 765

Ser Ser Lys Gly Glu Cys Phe Ile Ala Leu Glu Gly Thr Tyr Val Glu
    770                 775                 780

Asn Ser Ser Thr Ile Phe Ser Asn Val Ser Ile Val Lys Glu
785                 790                 795

<210> SEQ ID NO 30
<211> LENGTH: 2397
<212> TYPE: DNA
<213> ORGANISM: Artificial
<220> FEATURE:
<223> OTHER INFORMATION: A synthetic nucleotide sequence designed for
      expression in a plant cell and encodes the TIC2160 variant,
      TIC2160_17.

<400> SEQUENCE: 30
atgcagcgca tgatcatcgt ggacaacaac aagctgaacg tcagggccct cccgagcttc      60
atcgactact tcaacggcat ctacggcttc gccaccggca tcaaggacat catgggcatg     120
atcttcaaga ctgacaccgg cggtagcaac ctcaccctcg acgagatcct caagaaccag     180
aacctcctca cgacatctc cggcaagctc gacggcatca acggcgacct cggcgacctc     240
atcgcccagg gcaacctcaa ctccgagctg gccaaggagc tgctcaagat ctccaacgag     300
cagaaccaga tgctcaacca cgtgaacgcc cagctcaacg ccatcaactc caccctcaac     360
atctacctcc cgaagatcac ctcgatgctc aacgaggtca tgaagcagaa ccacgtgctc     420
tccctccaga tcgagttcct ctccaagcag ctccaggaga tcagcgacaa gctcgacatc     480
attaacctca cgtgctcat caactccacc ctcaccgaga tcactccggc ctaccagcgc     540
atcaagtacg tgaacgagaa gttcgacgag ctgacctcca ccgtggagaa caagaagtct     600
ggttacgaaa cgatgtgtc tagacaagtc atcgagaacc tcaacgagct gaccgagctg     660
gccaagtccg tgaccaagaa cgacatggac tccttcgagt tctacctcca gaccttccac     720
gacgtgatga ccggcaacaa tctgttcggc cgctccgccc tcaagaccgc ctccgaactc     780
atcaccaagg agaacgtgac cacccgtggc tccgagatcg gcaaggtgta caacttcctg     840

```
atcgtgctga cctccctgca agccaaggct ttcctgaccc tgaccgcttg ccgcaagctg    900
cttggcctga ccgacatcga ctacactcag atcatgaacc accacatcga cggccagaag    960
cgcgagttcc gcatcaacat cctgcccact ctgagcaaca acttcagcaa cccgagctac   1020
agcaagaacc gtggcagcga catcgacgac cccatcgtgg tcctggaggc tgcgcctggc   1080
tacgctctga tcggcttcga gatcctgaac gaccctctgc ctatcctcaa gggctaccag   1140
gctaggctca agccgaacta ccaagtggac cgggagagca tgagcgagac tatctacggt   1200
gacatccaca agctgttctg cccgaagcaa ctggagcaga agtactacat caaggacatc   1260
gagttcccgg agggttacgt catcaccaag atcgtcttcg agaagcggct gaaccagctt   1320
ggttacgagg tcactgctaa cttctacgac ccgagcactg gtagcatcga cctgaacaag   1380
gtcaaggtcg agagctggaa ggagaagtcc tgcgaggaag actcttgcga ggacgagtac   1440
agcatcatca aggcggagac tgatggcatc tacatgccgc ttggtgtcgt aagtgagact   1500
ttcctcactc cgatctacgg cttcggtctc actgtcgatg agaagaacca gaagattact   1560
ctcacgggca gtcttacct tcgggagtct ctcctggaga cggatctcct caacaatgag   1620
acgtaccta ttgcgtctcc ggacgggtac atcagttcca ttgtcgagaa ctggaacatc   1680
acgtctgaca acacgggctc ttggcgtgcg aacaataaca atgcgttcgt cgataaggca   1740
gatacgatca agggctcttc gtctctttac acgcataagg atggcgagtt ctctcagttc   1800
attgggaaca agctcaagcc gaagacgaac tatgtcattc agtacgtcat caagggtcgt   1860
ccagccatct atcttaagaa taacaaggac acgctcttcg aggatacgaa gaataacttc   1920
tcggacttcc agactgtcac caagaagttc aattcgggtg tcaatccatc ggaaatctac   1980
tttctcttca gaatcagtc ggagtatgag gcgtggggga caacttcat catccttgag   2040
atcaagtcgc tggagttctt gccacagatg ctcaagccag aggactggat tccctcgggc   2100
aatgtccaaa tgaaggatgg aggacgtctg gaaatcttgg gagatggata cttcaaacag   2160
ttcatcaaac tggagaatga ttcaacctac catctaagac tatcagtcaa agggacaggg   2220
cgggtttcaa tcatcgacga gtcaaagtac ctactgttcg tgaatgtcaa agacgaagac   2280
ctcacacgag tcatcaagaa cactagctca agggagagt gcttcatagc actcgaaggc   2340
acctacgtcg agaacagcag taccatcttc agtaatgtgt ccatcgtcaa ggagtga      2397
```

<210> SEQ ID NO 31
<211> LENGTH: 798
<212> TYPE: PRT
<213> ORGANISM: Artificial
<220> FEATURE:
<223> OTHER INFORMATION: An amino acid sequence of the TIC2160 variant,
      TIC2160_17 encoded by SEQ ID NO: 30.

<400> SEQUENCE: 31

Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
            20                  25                  30

Gly Ile Lys Asp Ile Met Gly Met Ile Phe Lys Thr Asp Thr Gly Gly
        35                  40                  45

Ser Asn Leu Thr Leu Asp Glu Ile Leu Lys Asn Gln Asn Leu Leu Asn
    50                  55                  60

Asp Ile Ser Gly Lys Leu Asp Gly Ile Asn Gly Asp Leu Gly Asp Leu
65                  70                  75                  80

```
Ile Ala Gln Gly Asn Leu Asn Ser Glu Leu Ala Lys Glu Leu Leu Lys
                 85                  90                  95
Ile Ser Asn Glu Gln Asn Gln Met Leu Asn His Val Asn Ala Gln Leu
            100                 105                 110
Asn Ala Ile Asn Ser Thr Leu Asn Ile Tyr Leu Pro Lys Ile Thr Ser
            115                 120                 125
Met Leu Asn Glu Val Met Lys Gln Asn His Val Leu Ser Leu Gln Ile
    130                 135                 140
Glu Phe Leu Ser Lys Gln Leu Gln Glu Ile Ser Asp Lys Leu Asp Ile
145                 150                 155                 160
Ile Asn Leu Asn Val Leu Ile Asn Ser Thr Leu Thr Glu Ile Thr Pro
                165                 170                 175
Ala Tyr Gln Arg Ile Lys Tyr Val Asn Glu Lys Phe Asp Glu Leu Thr
            180                 185                 190
Ser Thr Val Glu Asn Lys Lys Ser Gly Tyr Glu Asn Asp Val Ser Arg
        195                 200                 205
Gln Val Ile Glu Asn Leu Asn Glu Leu Thr Glu Leu Ala Lys Ser Val
    210                 215                 220
Thr Lys Asn Asp Met Asp Ser Phe Glu Phe Tyr Leu Gln Thr Phe His
225                 230                 235                 240
Asp Val Met Thr Gly Asn Asn Leu Phe Gly Arg Ser Ala Leu Lys Thr
                245                 250                 255
Ala Ser Glu Leu Ile Thr Lys Glu Asn Val Thr Thr Arg Gly Ser Glu
            260                 265                 270
Ile Gly Lys Val Tyr Asn Phe Leu Ile Val Leu Thr Ser Leu Gln Ala
        275                 280                 285
Lys Ala Phe Leu Thr Leu Thr Ala Cys Arg Lys Leu Leu Gly Leu Thr
    290                 295                 300
Asp Ile Asp Tyr Thr Gln Ile Met Asn His His Ile Asp Gly Gln Lys
305                 310                 315                 320
Arg Glu Phe Arg Ile Asn Ile Leu Pro Thr Leu Ser Asn Asn Phe Ser
                325                 330                 335
Asn Pro Ser Tyr Ser Lys Asn Arg Gly Ser Asp Ile Asp Asp Pro Ile
            340                 345                 350
Val Val Leu Glu Ala Ala Pro Gly Tyr Ala Leu Ile Gly Phe Glu Ile
        355                 360                 365
Leu Asn Asp Pro Leu Pro Ile Leu Lys Gly Tyr Gln Ala Arg Leu Lys
    370                 375                 380
Pro Asn Tyr Gln Val Asp Arg Glu Ser Met Ser Glu Thr Ile Tyr Gly
385                 390                 395                 400
Asp Ile His Lys Leu Phe Cys Pro Lys Gln Leu Glu Gln Lys Tyr Tyr
                405                 410                 415
Ile Lys Asp Ile Glu Phe Pro Glu Gly Tyr Val Ile Thr Lys Ile Val
            420                 425                 430
Phe Glu Lys Arg Leu Asn Gln Leu Gly Tyr Glu Val Thr Ala Asn Phe
        435                 440                 445
Tyr Asp Pro Ser Thr Gly Ser Ile Asp Leu Asn Lys Val Lys Val Glu
    450                 455                 460
Ser Trp Lys Glu Lys Ser Cys Glu Glu Asp Ser Cys Glu Asp Glu Tyr
465                 470                 475                 480
Ser Ile Ile Lys Ala Glu Thr Asp Gly Ile Tyr Met Pro Leu Gly Val
                485                 490                 495
Val Ser Glu Thr Phe Leu Thr Pro Ile Tyr Gly Phe Gly Leu Thr Val
```

```
                500            505              510
Asp Glu Lys Asn Gln Lys Ile Thr Leu Thr Gly Lys Ser Tyr Leu Arg
            515                520                525

Glu Ser Leu Leu Glu Thr Asp Leu Leu Asn Asn Glu Thr Tyr Leu Ile
        530                535                540

Ala Ser Pro Asp Gly Tyr Ile Ser Ser Ile Val Glu Asn Trp Asn Ile
545                550                555                560

Thr Ser Asp Asn Thr Gly Ser Trp Arg Ala Asn Asn Asn Asn Ala Phe
                565                570                575

Val Asp Lys Ala Asp Thr Ile Lys Gly Ser Ser Ser Leu Tyr Thr His
            580                585                590

Lys Asp Gly Glu Phe Ser Gln Phe Ile Gly Asn Lys Leu Lys Pro Lys
        595                600                605

Thr Asn Tyr Val Ile Gln Tyr Val Ile Lys Gly Arg Pro Ala Ile Tyr
    610                615                620

Leu Lys Asn Asn Lys Asp Thr Leu Phe Glu Asp Thr Lys Asn Asn Phe
625                630                635                640

Ser Asp Phe Gln Thr Val Thr Lys Lys Phe Asn Ser Gly Val Asn Pro
                645                650                655

Ser Glu Ile Tyr Phe Leu Phe Lys Asn Gln Ser Glu Tyr Glu Ala Trp
            660                665                670

Gly Asn Asn Phe Ile Ile Leu Glu Ile Lys Ser Leu Glu Phe Leu Pro
        675                680                685

Gln Met Leu Lys Pro Glu Asp Trp Ile Pro Ser Gly Asn Val Gln Met
    690                695                700

Lys Asp Gly Gly Arg Leu Glu Ile Leu Gly Asp Gly Tyr Phe Lys Gln
705                710                715                720

Phe Ile Lys Leu Glu Asn Asp Ser Thr Tyr His Leu Arg Leu Ser Val
                725                730                735

Lys Gly Thr Gly Arg Val Ser Ile Ile Asp Glu Ser Lys Tyr Leu Leu
            740                745                750

Phe Val Asn Val Lys Asp Glu Asp Leu Thr Arg Val Ile Lys Asn Thr
        755                760                765

Ser Ser Lys Gly Glu Cys Phe Ile Ala Leu Glu Gly Thr Tyr Val Glu
    770                775                780

Asn Ser Ser Thr Ile Phe Ser Asn Val Ser Ile Val Lys Glu
785                790                795
```

<210> SEQ ID NO 32
<211> LENGTH: 2397
<212> TYPE: DNA
<213> ORGANISM: Artificial
<220> FEATURE:
<223> OTHER INFORMATION: A synthetic nucleotide sequence designed for
      expression in a plant cell and encodes the TIC2160 variant,
      TIC2160_18.

<400> SEQUENCE: 32

```
atgcagcgca tgatcatcgt ggacaacaac aagctgaacg tcagggccct cccgagcttc    60
atcgactact tcaacggcat ctacggcttc gccaccggca tcaaggacat catgggcatg   120
atcttcaaga ctgacaccgg cggtagcaac ctcaccctcg acgagatcct caagaaccag   180
aacctcctca cgacatctc cggcaagctc gacggcatca acggcgacct cggcgacctc   240
atcgcccagg gcaacctcaa ctccgagctg gccaaggagc tgctcaagat ctccaacgag   300
cagaaccaga tgctcaacca cgtgaacgcc cagctcaacg ccatcaactc caccctcaac   360
```

```
atctacctcc cgaagatcac ctcgatgctc aacgaggtca tgaagcagaa ccacgtgctc    420
tccctccaga tcgagttcct ctccaagcag ctccaggaga tcagcgacaa gctcgacatc    480
attaacctca acgtgctcat caactccacc ctcaccgaga tcactccggc ctaccagcgc    540
atcaagtacg tgaacgagaa gttcgacgag ctgacctcca ccgtggagaa caagaagtct    600
ggttacgaaa acgatgtgtc tagacaagtc atcgagaacc tcaacgagct gaccgagctg    660
gccaagtccg tgaccaagaa cgacatggac tccttcgagt tctacctcca gaccttccac    720
gacgtgatga ccggcaacaa tctgttcggc cgctccgccc tcaagaccgc ctccgaactc    780
atcaccagaa cgaaactgt acccgtggc tcccaaatcg gcaaggtgta caacttcctg    840
atcgtgctga cctccctgca agccaaggct ttcctgaccc tgaccgcttg ccgcaagctg    900
cttggcctga ccgacatcga ctacactcag atcatgaacc accacatcga cggccagaag    960
cgcgagttcc gcatcaacat cctgcccact ctgagcaaca acttcagcaa cccgagctac   1020
agcaagaacc gtggcagcga catcgacgac cccatcgtgg tcctggaggc tgcgcctggc   1080
tacgctctga tcggcttcga gatcctgaac gaccctctgc ctatcctcaa gggctaccag   1140
gctaggctca agccgaacta ccaagtggac cgggagagca tgagcgagac tatctacggt   1200
gacatccaca gctgttctg cccgaagcaa ctggagcaga agtactacat caaggacatc   1260
gagttcccgg agggttacgt catcaccaag atcgtcttcg agaagcggct gaaccagctt   1320
ggttacgagg tcactgctaa cttctacgac ccgagcactg gtagcatcga cctgaacaag   1380
gtcaaggtcg agagctggaa ggagaagtcc tgcgaggaag actcttgcga ggacgagtac   1440
agcatcatca aggcggagac tgatggcatc tacatgccgc ttggtgtcgt aagtgagact   1500
ttcctcactc cgatctacgg cttcggtctc actgtcgatg agaagaacca gaagattact   1560
ctcacgggca agtcttacct tcgggagtct ctcctggaga cggatctcct caacaatgag   1620 acgtaccta ttgcgtctcc ggacgggtac atcagttcca ttgtcgagaa ctggaacatc   1680
acgtctgaca acacgggctc ttggcgtgcg aacaataaca atgcgttcgt cgataaggca   1740
gatacgatca agggctcttc gtctctttac acgcataagg atggcgagtt ctctcagttc   1800
attgggaaca agctcaagcc gaagacgaac tatgtcattc agtacgtcat caagggtcgt   1860
ccagccatct atcttaagaa taacaaggac acgctcttcg aggatacgaa gaataacttc   1920
tcggacttcc agactgtcac caagaagttc aattcgggtg tcaatccatc ggaaatctac   1980
tttctcttca gaatcagtc ggagtatgag gcgtggggga caacttcat catccttgag   2040 atcaagtcgc tggagttctt gccacagatg ctcaagccag aggactggat tccctcgggc   2100
aatgtccaaa tgaaggatgg aggacgtctg gaaatcttgg gagatggata cttcaaacag   2160
ttcatcaaac tggagaatga ttcaacctac catctaagac tatcagtcaa agggacaggg   2220
cgggtttcaa tcatcgacga gtcaaagtac ctactgttcg tgaatgtcaa agacgaagac   2280
ctcacacgag tcatcaagaa cactagctca aaggagagt gcttcatagc actcgaaggc   2340
acctacgtcg agaacagcag taccatcttc agtaatgtgt ccatcgtcaa ggagtga     2397
```

<210> SEQ ID NO 33
<211> LENGTH: 798
<212> TYPE: PRT
<213> ORGANISM: Artificial
<220> FEATURE:
<223> OTHER INFORMATION: An amino acid sequence of the TIC2160 variant, TIC2160_18 encoded by SEQ ID NO: 32.

<400> SEQUENCE: 33

```
Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
                20                  25                  30

Gly Ile Lys Asp Ile Met Gly Met Ile Phe Lys Thr Asp Thr Gly Gly
            35                  40                  45

Ser Asn Leu Thr Leu Asp Glu Ile Leu Lys Asn Gln Asn Leu Leu Asn
        50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
    130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
                165                 170                 175

Ala Tyr Gln Arg Ile Lys Tyr Val Asn Glu Lys Phe Asp Glu Leu Thr
            180                 185                 190

Ser Thr Val Glu Asn Lys Lys Ser Gly Tyr Glu Asn Asp Val Ser Arg
        195                 200                 205

Gln Val Ile Glu Asn Leu Asn Glu Leu Thr Glu Leu Ala Lys Ser Val
    210                 215                 220

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
                245                 250                 255

Ala Ser Glu Leu Ile Thr Arg Asn Glu Thr Val Thr Arg Gly Ser Gln
            260                 265                 270

Ile Gly Lys Val Tyr Asn Phe Leu Ile Val Leu Thr Ser Leu Gln Ala
        275                 280                 285

Lys Ala Phe Leu Thr Leu Thr Ala Cys Arg Lys Leu Leu Gly Leu Thr
    290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
                325                 330                 335

Asn Pro Ser Tyr Ser Lys Asn Arg Gly Ser Asp Ile Asp Asp Pro Ile
            340                 345                 350

Val Val Leu Glu Ala Ala Pro Gly Tyr Ala Leu Ile Gly Phe Glu Ile
        355                 360                 365

Leu Asn Asp Pro Leu Pro Ile Leu Lys Gly Tyr Gln Ala Arg Leu Lys
    370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Lys Gln Leu Glu Gln Lys Tyr Tyr
                405                 410                 415
```

Ile Lys Asp Ile Glu Phe Pro Glu Gly Tyr Val Ile Thr Lys Ile Val
                420                 425                 430

Phe Glu Lys Arg Leu Asn Gln Leu Gly Tyr Glu Val Thr Ala Asn Phe
435                 440                 445

Tyr Asp Pro Ser Thr Gly Ser Ile Asp Leu Asn Lys Val Lys Val Glu
                450                 455                 460

Ser Trp Lys Glu Lys Ser Cys Glu Glu Asp Ser Cys Glu Asp Glu Tyr
465                 470                 475                 480

Ser Ile Ile Lys Ala Glu Thr Asp Gly Ile Tyr Met Pro Leu Gly Val
                485                 490                 495

Val Ser Glu Thr Phe Leu Thr Pro Ile Tyr Gly Phe Gly Leu Thr Val
                500                 505                 510

Asp Glu Lys Asn Gln Lys Ile Thr Leu Thr Gly Lys Ser Tyr Leu Arg
                515                 520                 525

Glu Ser Leu Leu Glu Thr Asp Leu Leu Asn Asn Glu Thr Tyr Leu Ile
                530                 535                 540

Ala Ser Pro Asp Gly Tyr Ile Ser Ser Ile Val Glu Asn Trp Asn Ile
545                 550                 555                 560

Thr Ser Asp Asn Thr Gly Ser Trp Arg Ala Asn Asn Asn Asn Ala Phe
                565                 570                 575

Val Asp Lys Ala Asp Thr Ile Lys Gly Ser Ser Ser Leu Tyr Thr His
                580                 585                 590

Lys Asp Gly Glu Phe Ser Gln Phe Ile Gly Asn Lys Leu Lys Pro Lys
                595                 600                 605

Thr Asn Tyr Val Ile Gln Tyr Val Ile Lys Gly Arg Pro Ala Ile Tyr
                610                 615                 620

Leu Lys Asn Asn Lys Asp Thr Leu Phe Glu Asp Thr Lys Asn Asn Phe
625                 630                 635                 640

Ser Asp Phe Gln Thr Val Thr Lys Lys Phe Asn Ser Gly Val Asn Pro
                645                 650                 655

Ser Glu Ile Tyr Phe Leu Phe Lys Asn Gln Ser Glu Tyr Glu Ala Trp
                660                 665                 670

Gly Asn Asn Phe Ile Ile Leu Glu Ile Lys Ser Leu Glu Phe Leu Pro
                675                 680                 685

Gln Met Leu Lys Pro Glu Asp Trp Ile Pro Ser Gly Asn Val Gln Met
690                 695                 700

Lys Asp Gly Gly Arg Leu Glu Ile Leu Gly Asp Gly Tyr Phe Lys Gln
705                 710                 715                 720

Phe Ile Lys Leu Glu Asn Asp Ser Thr Tyr His Leu Arg Leu Ser Val
                725                 730                 735

Lys Gly Thr Gly Arg Val Ser Ile Ile Asp Glu Ser Lys Tyr Leu Leu
                740                 745                 750

Phe Val Asn Val Lys Asp Glu Asp Leu Thr Arg Val Ile Lys Asn Thr
                755                 760                 765

Ser Ser Lys Gly Glu Cys Phe Ile Ala Leu Glu Gly Thr Tyr Val Glu
                770                 775                 780

Asn Ser Ser Thr Ile Phe Ser Asn Val Ser Ile Val Lys Glu
785                 790                 795

<210> SEQ ID NO 34
<211> LENGTH: 2397
<212> TYPE: DNA
<213> ORGANISM: Artificial
<220> FEATURE:
<223> OTHER INFORMATION: A synthetic nucleotide sequence designed for expression in a plant cell and encodes the TIC2160 variant, TIC2160_20.

<400> SEQUENCE: 34

```
atgcagcgca tgatcatcgt ggacaacaac aagctgaacg tcagggccct cccgagcttc      60
atcgactact tcaacggcat ctacggcttc gccaccggca tcaaggacat catgggcatg     120
atcttcaaga ctgacaccgg cggtagcaac ctcaccctcg acgagatcct caagaaccag     180
aacctcctca acgacatctc cggcaagctc gacggcatca acggcgacct cggcgacctc     240
atcgcccagg gcaacctcaa ctccgagctg gccaaggagc tgctcaagat ctccaacgag     300
cagaaccaga tgctcaacca cgtgaacgcc cagctcaacg ccatcaactc caccctcaac     360
atctacctcc cgaagatcac ctcgatgctc aacgaggtca tgaagcagaa ccacgtgctc     420
tccctccaga tcgagttcct ctccaagcag ctccaggaga tcagcgacaa gctcgacatc     480
attaacctca acgtgctcat caactccacc ctcaccgaga tcactccggc ctaccagcgc     540
atcaagtacg tgaacgagaa gttcgacgag ctgacctcca ccgtggagaa gaacccgaag     600
tcctaccagg acaacgtgac caaggaggtc atcgagaacc tcaacgagct gaccgagctg     660
gccaagtccg tgaccaagaa cgacatggac tccttcgagt tctacctcca gaccttccac     720
gacgtgatga ccggcaacaa tctgttcggc cgctccgccc tcaagaccgc ctccgaactc     780
atcaccaagg agaacaccac cacccgtggc tccgagatcg gcaaggtgta caacttcctg     840
atcgtgctga cctccctgca agccaaggct ttcctgaccc tgaccgcttg ccgcaagctg     900
cttggcctga ccgacatcga ctacactcag atcatgaacc accacatcga cggccagaag     960
cgcgagttcc gcatcaacat cctgcccact ctgagcaaca acttcagcaa cccgagctac    1020
agcaagaacc gtggcagcga catcgacgac cccatcgtgg tcctggaggc tgcgcctggc    1080
tacgctctga tcggcttcga gatcctgaac gaccctctgc ctatcctcaa gggctaccag    1140
gctaggctca agccgaacta ccaagtggac cgggagagca tgagcgagac tatctacggt    1200
gacatccaca agctgttctg cccgaagcaa ctggagcaga agtactacat caaggacatc    1260
gagttcccgg agggttacgt catcaccaag atcgtcttcg agaagcggct gaaccagctt    1320
ggttacgagg tcactgctaa cttctacgac ccgagcactg gtagcatcga cctgaacaag    1380
gtcaaggtcg agagctggaa ggagaagtcc tgcgaggaag actcttgcga ggacgagtac    1440
agcatcatca aggcggagac tgatggcatc tacatgccgc ttggtgtcgt aagtgagact    1500
ttcctcactc cgatctacgg cttcggtctc actgtcgatg agaagaacca gaagattact    1560
ctcacgggca agtcttacct tcgggagtct ctcctggaga cggatctcct caacaatgag    1620
acgtacctta ttgcgtctcc ggacgggtac atcagttcca ttgtcgagaa ctggaacatc    1680
acgtctgaca cacgggctc ttggcgtgcg aacaataaca atgcgttcgt cgataaggca    1740
gatacgatca agggctcttc gtctctttac acgcataagg atggcgagtt ctctcagttc    1800
attgggaaca agctcaagcc gaagacgaac tatgtcattc agtacgtcat caagggtcgt    1860
ccagccatct atcttaagaa taacaaggac acgctcttcg aggatacgaa gaataacttc    1920
tcggacttcc agactgtcac caagaagttc aattcgggtg tcaatccatc ggaaatctac    1980
tttctcttca agaatcagtc ggagtatgag gcgtggggga caacttcat catccttgag    2040
atcaagtcgc tggagttctt gccacagatg ctcaagccag aggactggat ccctcgggc    2100
aatgtccaaa tgaaggatgg aggacgtctg gaaatcttgg gagatggata cttcaaacag    2160
ttcatcaaac tggagaatga ttcaacctac catctaagac tatcagtcaa agggacaggg    2220
```

```
cgggtttcaa tcatcgacga gtcaaagtac ctactgttcg tgaatgtcaa agacgaagac    2280
ctcacacgag tcatcaagaa cactagctca aagggagagt gcttcatagc actcgaaggc    2340
acctacgtcg agaacagcag taccatcttc agtaatgtgt ccatcgtcaa ggagtga      2397
```

<210> SEQ ID NO 35
<211> LENGTH: 798
<212> TYPE: PRT
<213> ORGANISM: Artificial
<220> FEATURE:
<223> OTHER INFORMATION: An amino acid sequence of the TIC2160 variant,
      TIC2160_20 encoded by SEQ ID NO: 34.

<400> SEQUENCE: 35

```
Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
            20                  25                  30

Gly Ile Lys Asp Ile Met Gly Met Ile Phe Lys Thr Asp Thr Gly Gly
        35                  40                  45

Ser Asn Leu Thr Leu Asp Glu Ile Leu Lys Asn Gln Asn Leu Leu Asn
    50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
    130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
                165                 170                 175

Ala Tyr Gln Arg Ile Lys Tyr Val Asn Glu Lys Phe Asp Glu Leu Thr
            180                 185                 190

Ser Thr Val Glu Lys Asn Pro Lys Ser Tyr Gln Asp Asn Val Thr Lys
        195                 200                 205

Glu Val Ile Glu Asn Leu Asn Glu Leu Thr Glu Leu Ala Lys Ser Val
    210                 215                 220

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
                245                 250                 255

Ala Ser Glu Leu Ile Thr Lys Glu Asn Thr Thr Thr Arg Gly Ser Glu
            260                 265                 270

Ile Gly Lys Val Tyr Asn Phe Leu Ile Val Leu Thr Ser Leu Gln Ala
        275                 280                 285

Lys Ala Phe Leu Thr Leu Thr Ala Cys Arg Lys Leu Leu Gly Leu Thr
    290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
                325                 330                 335
```

```
Asn Pro Ser Tyr Ser Lys Asn Arg Gly Ser Asp Ile Asp Asp Pro Ile
            340                 345                 350

Val Val Leu Glu Ala Ala Pro Gly Tyr Ala Leu Ile Gly Phe Glu Ile
            355                 360                 365

Leu Asn Asp Pro Leu Pro Ile Leu Lys Gly Tyr Gln Ala Arg Leu Lys
        370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Lys Gln Leu Glu Gln Lys Tyr Tyr
                405                 410                 415

Ile Lys Asp Ile Glu Phe Pro Gly Tyr Val Ile Thr Lys Ile Val
            420                 425                 430

Phe Glu Lys Arg Leu Asn Gln Leu Gly Tyr Glu Val Thr Ala Asn Phe
            435                 440                 445

Tyr Asp Pro Ser Thr Gly Ser Ile Asp Leu Asn Lys Val Lys Val Glu
    450                 455                 460

Ser Trp Lys Glu Lys Ser Cys Glu Glu Asp Ser Cys Glu Asp Glu Tyr
465                 470                 475                 480

Ser Ile Ile Lys Ala Glu Thr Asp Gly Ile Tyr Met Pro Leu Gly Val
                485                 490                 495

Val Ser Glu Thr Phe Leu Thr Pro Ile Tyr Gly Phe Gly Leu Thr Val
            500                 505                 510

Asp Glu Lys Asn Gln Lys Ile Thr Leu Thr Gly Lys Ser Tyr Leu Arg
        515                 520                 525

Glu Ser Leu Leu Glu Thr Asp Leu Leu Asn Asn Glu Thr Tyr Leu Ile
        530                 535                 540

Ala Ser Pro Asp Gly Tyr Ile Ser Ser Ile Val Glu Asn Trp Asn Ile
545                 550                 555                 560

Thr Ser Asp Asn Thr Gly Ser Trp Arg Ala Asn Asn Asn Ala Phe
                565                 570                 575

Val Asp Lys Ala Asp Thr Ile Lys Gly Ser Ser Leu Tyr Thr His
            580                 585                 590

Lys Asp Gly Glu Phe Ser Gln Phe Ile Gly Asn Lys Leu Lys Pro Lys
            595                 600                 605

Thr Asn Tyr Val Ile Gln Tyr Val Ile Lys Gly Arg Pro Ala Ile Tyr
        610                 615                 620

Leu Lys Asn Asn Lys Asp Thr Leu Phe Glu Asp Thr Lys Asn Asn Phe
625                 630                 635                 640

Ser Asp Phe Gln Thr Val Thr Lys Lys Phe Asn Ser Gly Val Asn Pro
                645                 650                 655

Ser Glu Ile Tyr Phe Leu Phe Lys Asn Gln Ser Glu Tyr Glu Ala Trp
            660                 665                 670

Gly Asn Asn Phe Ile Ile Leu Glu Ile Lys Ser Leu Glu Phe Leu Pro
            675                 680                 685

Gln Met Leu Lys Pro Glu Asp Trp Ile Pro Ser Gly Asn Val Gln Met
        690                 695                 700

Lys Asp Gly Gly Arg Leu Glu Ile Leu Gly Asp Gly Tyr Phe Lys Gln
705                 710                 715                 720

Phe Ile Lys Leu Glu Asn Asp Ser Thr Tyr His Leu Arg Leu Ser Val
                725                 730                 735

Lys Gly Thr Gly Arg Val Ser Ile Ile Asp Glu Ser Lys Ser Tyr Leu Leu
            740                 745                 750
```

```
Phe Val Asn Val Lys Asp Glu Asp Leu Thr Arg Val Ile Lys Asn Thr
            755                 760                 765

Ser Ser Lys Gly Glu Cys Phe Ile Ala Leu Gly Thr Tyr Val Glu
    770                 775                 780

Asn Ser Ser Thr Ile Phe Ser Asn Val Ser Ile Val Lys Glu
785                 790                 795

<210> SEQ ID NO 36
<211> LENGTH: 2397
<212> TYPE: DNA
<213> ORGANISM: Artificial
<220> FEATURE:
<223> OTHER INFORMATION: A synthetic nucleotide sequence designed for
      expression in a plant cell and encodes the TIC2160 variant,
      TIC2160_21.

<400> SEQUENCE: 36
atgcagcgca tgatcatcgt ggacaacaac aagctgaacg tcagggccct cccgagcttc      60
atcgactact tcaacggcat ctacggcttc gccaccggca tcaaggacat catgggcatg     120
atcttcaaga ctgacaccgg cggtagcaac ctcaccctcg acgagatcct caagaaccag     180
aacctcctca cgacatctc cggcaagctc gacggcatca cggcgacct cggcgacctc     240 atcgcccagg gcaacctcaa ctccgagctg gccaaggagc tgctcaagat ctccaacgag     300
cagaaccaga tgctcaacca cgtgaacgcc cagctcaacg ccatcaactc caccctcaac     360
atctacctcc cgaagatcac ctcgatgctc aacgaggtca tgaagcagaa ccacgtgctc     420
tccctccaga tcgagttcct ctccaagcag ctccaggaga tcagcgacaa gctcgacatc     480
attaacctca acgtgctcat caactccacc ctcaccgaga tcactccggc ctaccagcgc     540
atcaagtacg tgaacgagaa gttcgacgag ctgacctcca cgtggagaa gaacccgaag     600 tcctaccagg acaacgtgac caaggaggtc atcgagaacc tcaacgagct gaccgagctg     660
gccaagtccg tgaccaagaa cgacatggac tccttcgagt tctacctcca gaccttccac     720
gacgtgatga ccggcaacaa tctgttcggc cgctccgccc tcaggaccgc ctcccaactc     780
atcaccaaga acgagacggt cacccgtggc tccgagatcg gcaaggtgta caacttcctg     840
atcgtgctga cctccctgca agccaaggct ttcctgaccc tgaccgcttg ccgcaagctg     900
cttggcctga ccgacatcga ctacactcag atcatgaacc accacatcga cggccagaag     960
cgcgagttcc gcatcaacat cctgcccact ctgagcaaca acttcagcaa cccgagctac    1020
agcaagaacc gtggcagcga catcgacgac cccatcgtgg tcctggaggc tgcgcctggc    1080
tacgctctga tcggcttcga gatcctgaac gaccctctgc ctatcctcaa gggctaccag    1140
gctaggctca gccgaactac caagtggac cgggagagca tgagcgagac tatctacggt    1200
gacatccaca agctgttctg cccgaagcaa ctggagcaga agtactacat caaggacatc    1260
gagttcccgg agggttacgt catcaccaag atcgtcttcg agaagcggct gaaccagctt    1320
ggttacgagg tcactgctaa cttctacgac ccgagcactg gtagcatcga cctgaacaag    1380
gtcaaggtcg agagctggaa ggagaagtcc tgcgaggaag actcttgcga ggacgagtac    1440
agcatcatca ggcggagac tgatggcatc tacatgccgc ttggtgtcgt aagtgagact    1500
ttcctcactc cgatctacgg cttcggtctc actgtcgatg agaagaacca gaagattact    1560
ctcacgggca gtcttacct tcgggagtct ctcctggaga cggatctcct caacaatgag    1620 acgtaccctta ttgcgtctcc ggacgggtac atcagttcca ttgtcgagaa ctggaacatc    1680
acgtctgaca acacgggctc ttggcgtgcg aacaataaca atgcgttcgt cgataaggca    1740
```

```
gatacgatca agggctcttc gtctctttac acgcataagg atggcgagtt ctctcagttc    1800
attgggaaca agctcaagcc gaagacgaac tatgtcattc agtacgtcat caagggtcgt    1860
ccagccatct atcttaagaa taacaaggac acgctcttcg aggatacgaa gaataacttc    1920
tcggacttcc agactgtcac caagaagttc aattcgggtg tcaatccatc ggaaatctac    1980
tttctcttca agaatcagtc ggagtatgag gcgtggggga acaacttcat catccttgag    2040
atcaagtcgc tggagttctt gccacagatg ctcaagccag aggactggat tccctcgggc    2100
aatgtccaaa tgaaggatgg aggacgtctg gaaatcttgg gagatggata cttcaaacag    2160
ttcatcaaac tggagaatga ttcaacctac catctaagac tatcagtcaa agggacaggg    2220
cgggtttcaa tcatcgacga gtcaaagtac ctactgttcg tgaatgtcaa agacgaagac    2280
ctcacacgag tcatcaagaa cactagctca aagggagagt gcttcatagc actcgaaggc    2340
acctacgtcg agaacagcag taccatcttc agtaatgtgt ccatcgtcaa ggagtga       2397
```

<210> SEQ ID NO 37
<211> LENGTH: 798
<212> TYPE: PRT
<213> ORGANISM: Artificial
<220> FEATURE:
<223> OTHER INFORMATION: An amino acid sequence of the TIC2160 variant, TIC2160_21 encoded by SEQ ID NO: 36.

<400> SEQUENCE: 37

```
Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
            20                  25                  30

Gly Ile Lys Asp Ile Met Gly Met Ile Phe Lys Thr Asp Thr Gly Gly
        35                  40                  45

Ser Asn Leu Thr Leu Asp Glu Ile Leu Lys Asn Gln Asn Leu Leu Asn
    50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
    130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
                165                 170                 175

Ala Tyr Gln Arg Ile Lys Tyr Val Asn Glu Lys Phe Asp Glu Leu Thr
            180                 185                 190

Ser Thr Val Glu Lys Asn Pro Lys Ser Tyr Gln Asp Asn Val Thr Lys
        195                 200                 205

Glu Val Ile Glu Asn Leu Asn Glu Leu Thr Glu Leu Ala Lys Ser Val
    210                 215                 220

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Arg Thr
```

```
            245                 250                 255
Ala Ser Gln Leu Ile Thr Lys Asn Glu Thr Val Thr Arg Gly Ser Glu
            260                 265                 270

Ile Gly Lys Val Tyr Asn Phe Leu Ile Val Leu Thr Ser Leu Gln Ala
            275                 280                 285

Lys Ala Phe Leu Thr Leu Thr Ala Cys Arg Lys Leu Leu Gly Leu Thr
            290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
                    325                 330                 335

Asn Pro Ser Tyr Ser Lys Asn Arg Gly Ser Asp Ile Asp Asp Pro Ile
                    340                 345                 350

Val Val Leu Glu Ala Ala Pro Gly Tyr Ala Leu Ile Gly Phe Glu Ile
                    355                 360                 365

Leu Asn Asp Pro Leu Pro Ile Leu Lys Gly Tyr Gln Ala Arg Leu Lys
            370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Lys Gln Leu Glu Gln Lys Tyr Tyr
                    405                 410                 415

Ile Lys Asp Ile Glu Phe Pro Gly Tyr Val Ile Thr Lys Ile Val
                    420                 425                 430

Phe Glu Lys Arg Leu Asn Gln Leu Gly Tyr Glu Val Thr Ala Asn Phe
            435                 440                 445

Tyr Asp Pro Ser Thr Gly Ser Ile Asp Leu Asn Lys Val Lys Val Glu
450                 455                 460

Ser Trp Lys Glu Lys Ser Cys Glu Glu Asp Ser Cys Glu Asp Glu Tyr
465                 470                 475                 480

Ser Ile Ile Lys Ala Glu Thr Asp Gly Ile Tyr Met Pro Leu Gly Val
                    485                 490                 495

Val Ser Glu Thr Phe Leu Thr Pro Ile Tyr Gly Phe Gly Leu Thr Val
            500                 505                 510

Asp Glu Lys Asn Gln Lys Ile Thr Leu Thr Gly Lys Ser Tyr Leu Arg
            515                 520                 525

Glu Ser Leu Leu Glu Thr Asp Leu Leu Asn Asn Glu Thr Tyr Leu Ile
            530                 535                 540

Ala Ser Pro Asp Gly Tyr Ile Ser Ser Ile Val Glu Asn Trp Asn Ile
545                 550                 555                 560

Thr Ser Asp Asn Thr Gly Ser Trp Arg Ala Asn Asn Asn Ala Phe
                    565                 570                 575

Val Asp Lys Ala Asp Thr Ile Lys Gly Ser Ser Leu Tyr Thr His
            580                 585                 590

Lys Asp Gly Glu Phe Ser Gln Phe Ile Gly Asn Lys Leu Lys Pro Lys
            595                 600                 605

Thr Asn Tyr Val Ile Gln Tyr Val Ile Lys Gly Arg Pro Ala Ile Tyr
            610                 615                 620

Leu Lys Asn Asn Lys Asp Thr Leu Phe Glu Asp Thr Lys Asn Asn Phe
625                 630                 635                 640

Ser Asp Phe Gln Thr Val Thr Lys Lys Phe Asn Ser Gly Val Asn Pro
                    645                 650                 655

Ser Glu Ile Tyr Phe Leu Phe Lys Asn Gln Ser Glu Tyr Glu Ala Trp
                    660                 665                 670
```

Gly Asn Asn Phe Ile Ile Leu Glu Ile Lys Ser Leu Glu Phe Leu Pro
            675                 680                 685

Gln Met Leu Lys Pro Glu Asp Trp Ile Pro Ser Gly Asn Val Gln Met
        690                 695                 700

Lys Asp Gly Gly Arg Leu Glu Ile Leu Gly Asp Gly Tyr Phe Lys Gln
705                 710                 715                 720

Phe Ile Lys Leu Glu Asn Asp Ser Thr Tyr His Leu Arg Leu Ser Val
                725                 730                 735

Lys Gly Thr Gly Arg Val Ser Ile Ile Asp Glu Ser Lys Tyr Leu Leu
            740                 745                 750

Phe Val Asn Val Lys Asp Glu Asp Leu Thr Arg Val Ile Lys Asn Thr
                755                 760                 765

Ser Ser Lys Gly Glu Cys Phe Ile Ala Leu Glu Gly Thr Tyr Val Glu
        770                 775                 780

Asn Ser Ser Thr Ile Phe Ser Asn Val Ser Ile Val Lys Glu
785                 790                 795

<210> SEQ ID NO 38
<211> LENGTH: 2403
<212> TYPE: DNA
<213> ORGANISM: Artificial
<220> FEATURE:
<223> OTHER INFORMATION: A synthetic nucleotide sequence designed for
      expression in a plant cell and encodes the TIC2160 variant,
      TIC5420_13.

<400> SEQUENCE: 38

```
atgatgatcg tggacaacac caagctggac accagggccc tcccgagctt catcgactac      60
ttcaacggca tctacggctt cgccaccggc atcaaggaca tcatgggcat gatcttcaag     120
actgacaccg gctctagcaa cctcaccctc gacgagatcc tcaagaacca gaacctcctc     180
aacgacatct ccagcaagct cgacggcatc aacggcaccc tcggcgacct catcgcccag     240
ggcaacctca actccgagct ggccaaggag ctgctcaaga tctccaacga gcagaaccag     300
atgctcaacc acgtgaacgc ccagctcaac gccatcaact ccaccctcaa cgtttacctc     360
ccgaagatca cctcgatgct caacgaggtc atgatgcaga ccacgtgct ctccctccag      420 atcgagttcc tctccaagca gctccaggag atcagcgaca agctcgacat cattaacctc     480
aacgtgctca tcaactccac cctcaccgag atcactccgg cctaccagcg catcaagtac     540
gtgaacgaga agttcgacga gctgacctcc accgtggaca gccgcggtcg ctcctaccag     600
gacaacgtga ccaaggaggt catcaacgag ctcaccgacc tgaccgagct ggccaagtcc     660
gtgaccaaga cgacatgga ctccttcgag ttctacctcc agaccttcca cgacgtgatg      720
accggcaaca atctgttcgg caagtccgcc ctcaggaccg ccgcccaact catcaccaag     780
aacgagacgg tcacccgtgg ctccgagatc ggcaaggtgt acaacttcct gatcgtgctg     840
acctccctgc aagccaaggc tttcctgacc ctgaccgctt gccgcaagct gcttggcctg     900
accgacatcg actacactaa gaccatgaac cagcacctcg acggccagaa gcgcgagttc     960
cgcatcaaca tcctgcccac tctgagcaac agcttcagca acccgagcta caccaggcag    1020
aagggcagcg acatcgacga ccccatcgtg gtcctggagg ctgcgcctgg ctacgctctg    1080
atcggcttcc agatcctgaa cgaccctctg cctatcctca agggctacca ggctaggctc    1140
aagccgaact accaagtgga ccgggagagc atgagcgaga ctatctacgg tgacatccac    1200
aagctgttct gcccgaggga actggagcag aagtactaca tcaggaacat cgacttcccg    1260
```

-continued

```
gagggttacg tcatcaccaa gatcgtcttc gagaagcggc tgaaccagct tggttacgag    1320
gtcactgcta acttctacga cccgagcact ggcaacatcg acctgaacaa ggtcaaggtc    1380
gagagctggc gtcaggaggg ctccgacgac gacacttccc ggaagcggtt ctgcgagcac    1440
gagtacagcc tcatcaaggc ggagactgat ggtatctaca tgccgcttgg tgtcgtaagt    1500
gagactttcc tcactccgat ctacggcttc ggtctcactg tcgatgagaa gaaccagaag    1560
attactctca cgggcaagtc ttaccttcgg gagtctctcc tggagacgga tctcgtcaac    1620
aatgagacgt accttattgc gtctccggac gggtacttca gttccattgt cgagaactgg    1680
aacatcacgt ctgacaactt cggctcttgg cgtgcgaaca ataacaatgc gttcgtcgat    1740
aaggaggata cggtcaaggg ctcttcgtct ctttacacgc ataaggatgg cgagttctct    1800
cagttcattg gaacaagct caagccgaag acgaactatg tcattcagta cgccatcaag    1860
ggtcgtccag ccatctatct taagaataac aaggatacgc tcttcgagga tacgaacaat    1920
aacttctcgg acttccagac tgtcaccaag aaattcaatt cgggtgccaa tccatcggaa    1980
atctacctcc tcttcaagaa tcagggcgag tatgaggcgt gggggaacaa cttcatcatc    2040
cttgagatca agtcgctgga gctgttgcca cagatgctca agccagagga ctggattccc    2100
tcgggcaatg tccaaatgaa ggatgaggga cgtctgcaaa tcttgggaga tggatacttc    2160
aaacaattca tcaaactcca gaatgattca acctaccatc taagactatc agtcaaaggg    2220
acagggcggg tttcaatcat cgacgagtca aactacctgt tcttcgtgaa catcaaagac    2280
gaagacttca aagcgtcat caagaaccgc agctcagagg gagactgctt catagcactc    2340
gaaggcagct acgtcgagaa cagcagtacc atcttcagtt ccgtgtccat cgtcaaggag    2400
tga                                                                 2403
```

<210> SEQ ID NO 39
<211> LENGTH: 800
<212> TYPE: PRT
<213> ORGANISM: Artificial
<220> FEATURE:
<223> OTHER INFORMATION: An amino acid sequence of the TIC2160 variant, TIC5420_13 encoded by SEQ ID NO: 38.

<400> SEQUENCE: 39

```
Met Met Ile Val Asp Asn Thr Lys Leu Asp Thr Arg Ala Leu Pro Ser
1               5                   10                  15

Phe Ile Asp Tyr Phe Asn Gly Ile Tyr Gly Phe Ala Thr Gly Ile Lys
                20                  25                  30

Asp Ile Met Gly Met Ile Phe Lys Thr Asp Thr Gly Ser Ser Asn Leu
            35                  40                  45

Thr Leu Asp Glu Ile Leu Lys Asn Gln Asn Leu Leu Asn Asp Ile Ser
        50                  55                  60

Ser Lys Leu Asp Gly Ile Asn Gly Thr Leu Gly Asp Leu Ile Ala Gln
65                  70                  75                  80

Gly Asn Leu Asn Ser Glu Leu Ala Lys Glu Leu Leu Lys Ile Ser Asn
                85                  90                  95

Glu Gln Asn Gln Met Leu Asn His Val Asn Ala Gln Leu Asn Ala Ile
                100                 105                 110

Asn Ser Thr Leu Asn Val Tyr Leu Pro Lys Ile Thr Ser Met Leu Asn
            115                 120                 125

Glu Val Met Met Gln Asn His Val Leu Ser Leu Gln Ile Glu Phe Leu
        130                 135                 140

Ser Lys Gln Leu Gln Glu Ile Ser Asp Lys Leu Asp Ile Ile Asn Leu
```

```
               145                 150                 155                 160
        Asn Val Leu Ile Asn Ser Thr Leu Thr Glu Ile Thr Pro Ala Tyr Gln
                        165                 170                 175
        Arg Ile Lys Tyr Val Asn Glu Lys Phe Asp Glu Leu Thr Ser Thr Val
                        180                 185                 190
        Asp Ser Arg Gly Arg Ser Tyr Gln Asp Asn Val Thr Lys Glu Val Ile
                        195                 200                 205
        Asn Glu Leu Thr Asp Leu Thr Glu Leu Ala Lys Ser Val Thr Lys Asn
                        210                 215                 220
        Asp Met Asp Ser Phe Glu Phe Tyr Leu Gln Thr Phe His Asp Val Met
        225                 230                 235                 240
        Thr Gly Asn Asn Leu Phe Gly Lys Ser Ala Leu Arg Thr Ala Ala Gln
                        245                 250                 255
        Leu Ile Thr Lys Asn Glu Thr Val Thr Arg Gly Ser Glu Ile Gly Lys
                        260                 265                 270
        Val Tyr Asn Phe Leu Ile Val Leu Thr Ser Leu Gln Ala Lys Ala Phe
                        275                 280                 285
        Leu Thr Leu Thr Ala Cys Arg Lys Leu Leu Gly Leu Thr Asp Ile Asp
                        290                 295                 300
        Tyr Thr Lys Thr Met Asn Gln His Leu Asp Gly Gln Lys Arg Glu Phe
        305                 310                 315                 320
        Arg Ile Asn Ile Leu Pro Thr Leu Ser Asn Ser Phe Ser Asn Pro Ser
                        325                 330                 335
        Tyr Thr Arg Gln Lys Gly Ser Asp Ile Asp Pro Ile Val Val Leu
                        340                 345                 350
        Glu Ala Ala Pro Gly Tyr Ala Leu Ile Gly Phe Gln Ile Leu Asn Asp
                        355                 360                 365
        Pro Leu Pro Ile Leu Lys Gly Tyr Gln Ala Arg Leu Lys Pro Asn Tyr
        370                 375                 380
        Gln Val Asp Arg Glu Ser Met Ser Glu Thr Ile Tyr Gly Asp Ile His
        385                 390                 395                 400
        Lys Leu Phe Cys Pro Arg Glu Leu Glu Gln Lys Tyr Tyr Ile Arg Asn
                        405                 410                 415
        Ile Asp Phe Pro Glu Gly Tyr Val Ile Thr Lys Ile Val Phe Glu Lys
                        420                 425                 430
        Arg Leu Asn Gln Leu Gly Tyr Glu Val Thr Ala Asn Phe Tyr Asp Pro
                        435                 440                 445
        Ser Thr Gly Asn Ile Asp Leu Asn Lys Val Lys Val Glu Ser Trp Arg
                        450                 455                 460
        Gln Glu Gly Ser Asp Asp Asp Thr Ser Arg Lys Arg Phe Cys Glu His
        465                 470                 475                 480
        Glu Tyr Ser Leu Ile Lys Ala Glu Thr Asp Gly Ile Tyr Met Pro Leu
                        485                 490                 495
        Gly Val Val Ser Glu Thr Phe Leu Thr Pro Ile Tyr Gly Phe Gly Leu
                        500                 505                 510
        Thr Val Asp Glu Lys Asn Gln Lys Ile Thr Leu Thr Gly Lys Ser Tyr
                        515                 520                 525
        Leu Arg Glu Ser Leu Leu Glu Thr Asp Leu Val Asn Asn Glu Thr Tyr
                        530                 535                 540
        Leu Ile Ala Ser Pro Asp Gly Tyr Phe Ser Ser Ile Val Glu Asn Trp
        545                 550                 555                 560
        Asn Ile Thr Ser Asp Asn Phe Gly Ser Trp Arg Ala Asn Asn Asn Asn
                        565                 570                 575
```

```
Ala Phe Val Asp Lys Glu Asp Thr Val Lys Gly Ser Ser Leu Tyr
            580                 585                 590

Thr His Lys Asp Gly Glu Phe Ser Gln Phe Ile Gly Asn Lys Leu Lys
        595                 600                 605

Pro Lys Thr Asn Tyr Val Ile Gln Tyr Ala Ile Lys Gly Arg Pro Ala
    610                 615                 620

Ile Tyr Leu Lys Asn Asn Lys Asp Thr Leu Phe Glu Asp Thr Asn Asn
625                 630                 635                 640

Asn Phe Ser Asp Phe Gln Thr Val Thr Lys Lys Phe Asn Ser Gly Ala
                645                 650                 655

Asn Pro Ser Glu Ile Tyr Leu Leu Phe Lys Asn Gln Gly Glu Tyr Glu
            660                 665                 670

Ala Trp Gly Asn Asn Phe Ile Ile Leu Glu Ile Lys Ser Leu Glu Leu
        675                 680                 685

Leu Pro Gln Met Leu Lys Pro Glu Asp Trp Ile Pro Ser Gly Asn Val
    690                 695                 700

Gln Met Lys Asp Glu Gly Arg Leu Glu Ile Leu Gly Asp Gly Tyr Phe
705                 710                 715                 720

Lys Gln Phe Ile Lys Leu Gln Asn Asp Ser Thr Tyr His Leu Arg Leu
                725                 730                 735

Ser Val Lys Gly Thr Gly Arg Val Ser Ile Ile Asp Glu Ser Asn Tyr
            740                 745                 750

Leu Phe Phe Val Asn Ile Lys Asp Glu Asp Phe Thr Ser Val Ile Lys
        755                 760                 765

Asn Arg Ser Ser Glu Gly Asp Cys Phe Ile Ala Leu Glu Gly Ser Tyr
    770                 775                 780

Val Glu Asn Ser Ser Thr Ile Phe Ser Ser Val Ser Ile Val Lys Glu
785                 790                 795                 800

<210> SEQ ID NO 40
<211> LENGTH: 2358
<212> TYPE: DNA
<213> ORGANISM: Artificial
<220> FEATURE:
<223> OTHER INFORMATION: A synthetic nucleotide sequence designed for
      expression in a plant cell and encodes the TIC2160 variant,
      TIC5420_a.

<400> SEQUENCE: 40
atgatgatcg tggacaacaa caagctgaac gtcagggccc tcccgagctt catcgactac      60
ttcaacggca tctacggctt cgccaccggc atcaaggaca tcatgggcat gatcttcaag     120
actgacaccg gcggtagcaa cctcacccctc gacgagatcc tcaagaacca gaacctcctc    180
aacgacatct ccggcaagct cgacggcatc aacggcggcc tcggcgacct catcgcccag     240
ggcaacctca actccgagct ggccaaggag ctgctcaaga tctccaacga gcagaaccag     300
atgctcaacc acgtgaacgc ccagctcaac gccatcaact ccaccctcaa cgtttacctc     360
ccgaagatca cctcgatgct caacgaggtc atgatgcaga accacgtgct ctccctccag     420
atcgagttcc tctccaagca gctccaggag atcagcgaca agctcgacat cattaacctc     480
aacgtgctca tcaactccac cctcaccgag atcactccgg cctaccagcg catcaagtac     540
gtgaacgaga agttcgacga gctgacctcc accgtggaga agaactccaa ggcctaccag     600
gacaacgtga ccaaggaggt catcgagaac ctcaccgacc tgaccgagct ggccaagtcc     660
gtgaccaaga acgacatgga ctccttcgag ttctacctcc agaccttcca cgacgtgatg     720
```

-continued

```
accggcaaca atctgttcgg ccgctccgcc ctcaagaccg ccgccgaact catcaccaag      780
gagaacgtga ccacccgtgg ctccgagatc ggcaaggtgt acaacttcct gatcgtgctg      840
acctccctgc aagccaaggc tttcctgacc ctgaccgctt gccgcaagct gcttggcctg      900
accgacatcg actacactaa gaccatgaac cagcacctcg acggccagaa gcgcgagttc      960
cgcatcaaca tcctgcccac tctgagcaac agcttcagca acccgagcta cagcaagaac     1020
cgtggcagcg acatcgacga ccccatcgtg gtcctggagg ctgcgcctgg ctacgctctg     1080
atcggcttcc agatcctgaa cgaccctctg cctatcctca agggctacca ggctaggctc     1140
aagccgaact accaagtgga ccgggagagc atgagcgaga ctatctacgg tgacatccac     1200
aagctgttct gcccgaagca actggagcag aagtactaca tcaaggacat cgagttcccg     1260
gagggttacg tcatcaccaa gatcgtcttc gagaagcggc tgaaccagct tggttacgag     1320
gtcactgcta acttctacga cccgagcact ggcaacatcg acctgaacaa ggtcaaggtc     1380
gagagcagcg aggcggagta cagcctcatc aaggcggaga ctgatggtat ctacatgccg     1440
cttggtgtcg taagtgagac tttcctcact ccgatctacg gcttcggtct cactgtcgat     1500
gagaagaacc agaagattac tctcacgggc aagtcttacc ttcgggagtc tctcctggag     1560
acggatctcg tcaacaatga gacgtacctt attgcgtctc cggacgggta cttcagttcc     1620
attgtcgaga actggaacat cacgtctgac aacttcggct cttggcgtgc gaacaataac     1680
aatgcgttcg tcgataagga ggatacggtc aagggctctt cgtctcttta cacgcataag     1740
gatggcgagt ctctcagtt cattgggaac aagctcaagc cgaagacgaa ctatgtcatt     1800
cagtacgcca tcaagggtcg tccagccatc tatcttaaga ataacaagga tacgctcttc     1860
gaggatacga acaataactt ctcggacttc cagactgtca ccaagaaatt caattcgggt     1920
gccaatccat cggaaatcta cctcctcttc aagaatcagg gcgagtatga ggcgtggggg     1980
aacaacttca tcatccttga gatcaagtcg ctggagctgt tgccacagat gctcaagcca     2040
gaggactgga ttccctcggg caatgtccaa atgaaggatg agggacgtct ggaaatcttg     2100
ggagatggat acttcaaaca attcatcaaa ctccagaatg attcaaccta ccatctaaga     2160
ctatcagtca aaggacagg gcgggtttca atcatcgacg agtcaaacta cctgttcttc     2220
gtgaacatca agacgaaga cttcacaagc gtcatcaaga accgcagctc agagggagac     2280
tgcttcatag cactcgaagg cagctacgtc gagaacagca gtaccatctt cagttccgtg     2340
tccatcgtca aggagtga                                                   2358
```

<210> SEQ ID NO 41
<211> LENGTH: 785
<212> TYPE: PRT
<213> ORGANISM: Artificial
<220> FEATURE:
<223> OTHER INFORMATION: An amino acid sequence of the TIC2160 variant, TIC5420_a encoded by SEQ ID NO: 40.

<400> SEQUENCE: 41

```
Met Met Ile Val Asp Asn Asn Lys Leu Asn Val Arg Ala Leu Pro Ser
  1               5                  10                  15

Phe Ile Asp Tyr Phe Asn Gly Ile Tyr Gly Phe Ala Thr Gly Ile Lys
                 20                  25                  30

Asp Ile Met Gly Met Ile Phe Lys Thr Asp Thr Gly Gly Ser Asn Leu
             35                  40                  45

Thr Leu Asp Glu Ile Leu Lys Asn Gln Asn Leu Leu Asn Asp Ile Ser
         50                  55                  60
```

Gly Lys Leu Asp Gly Ile Asn Gly Gly Leu Gly Asp Leu Ile Ala Gln
65                  70                  75                  80

Gly Asn Leu Asn Ser Glu Leu Ala Lys Glu Leu Leu Lys Ile Ser Asn
                85                  90                  95

Glu Gln Asn Gln Met Leu Asn His Val Asn Ala Gln Leu Asn Ala Ile
            100                 105                 110

Asn Ser Thr Leu Asn Val Tyr Leu Pro Lys Ile Thr Ser Met Leu Asn
        115                 120                 125

Glu Val Met Met Gln Asn His Val Leu Ser Leu Gln Ile Glu Phe Leu
    130                 135                 140

Ser Lys Gln Leu Gln Glu Ile Ser Asp Lys Leu Asp Ile Ile Asn Leu
145                 150                 155                 160

Asn Val Leu Ile Asn Ser Thr Leu Thr Glu Ile Thr Pro Ala Tyr Gln
                165                 170                 175

Arg Ile Lys Tyr Val Asn Glu Lys Phe Asp Glu Leu Thr Ser Thr Val
            180                 185                 190

Glu Lys Asn Ser Lys Ala Tyr Gln Asp Asn Val Thr Lys Glu Val Ile
        195                 200                 205

Glu Asn Leu Thr Asp Leu Thr Glu Leu Ala Lys Ser Val Thr Lys Asn
    210                 215                 220

Asp Met Asp Ser Phe Glu Phe Tyr Leu Gln Thr Phe His Asp Val Met
225                 230                 235                 240

Thr Gly Asn Asn Leu Phe Gly Arg Ser Ala Leu Lys Thr Ala Ala Glu
                245                 250                 255

Leu Ile Thr Lys Glu Asn Val Thr Thr Arg Gly Ser Glu Ile Gly Lys
            260                 265                 270

Val Tyr Asn Phe Leu Ile Val Leu Thr Ser Leu Gln Ala Lys Ala Phe
        275                 280                 285

Leu Thr Leu Thr Ala Cys Arg Lys Leu Leu Gly Leu Thr Asp Ile Asp
    290                 295                 300

Tyr Thr Lys Thr Met Asn Gln His Leu Asp Gly Gln Lys Arg Glu Phe
305                 310                 315                 320

Arg Ile Asn Ile Leu Pro Thr Leu Ser Asn Ser Phe Ser Asn Pro Ser
                325                 330                 335

Tyr Ser Lys Asn Arg Gly Ser Asp Ile Asp Pro Ile Val Val Leu
            340                 345                 350

Glu Ala Ala Pro Gly Tyr Ala Leu Ile Gly Phe Gln Ile Leu Asn Asp
        355                 360                 365

Pro Leu Pro Ile Leu Lys Gly Tyr Gln Ala Arg Leu Lys Pro Asn Tyr
    370                 375                 380

Gln Val Asp Arg Glu Ser Met Ser Glu Thr Ile Tyr Gly Asp Ile His
385                 390                 395                 400

Lys Leu Phe Cys Pro Lys Gln Leu Glu Gln Lys Tyr Ile Lys Asp
                405                 410                 415

Ile Glu Phe Pro Glu Gly Tyr Val Ile Thr Lys Ile Val Phe Glu Lys
            420                 425                 430

Arg Leu Asn Gln Leu Gly Tyr Glu Val Thr Ala Asn Phe Tyr Asp Pro
        435                 440                 445

Ser Thr Gly Asn Ile Asp Leu Asn Lys Val Lys Glu Ser Ser Glu
    450                 455                 460

Ala Glu Tyr Ser Leu Ile Lys Ala Glu Thr Asp Gly Ile Tyr Met Pro
465                 470                 475                 480

Leu Gly Val Val Ser Glu Thr Phe Leu Thr Pro Ile Tyr Gly Phe Gly

| | | 485 | | | | 490 | | | | 495 | | |
|---|---|---|---|---|---|---|---|---|---|---|---|---|

Leu Thr Val Asp Glu Lys Asn Gln Lys Ile Thr Leu Thr Gly Lys Ser
            500                 505                 510

Tyr Leu Arg Glu Ser Leu Leu Glu Thr Asp Leu Val Asn Asn Glu Thr
            515                 520                 525

Tyr Leu Ile Ala Ser Pro Asp Gly Tyr Phe Ser Ser Ile Val Glu Asn
            530                 535                 540

Trp Asn Ile Thr Ser Asp Asn Phe Gly Ser Trp Arg Ala Asn Asn Asn
545                 550                 555                 560

Asn Ala Phe Val Asp Lys Glu Asp Thr Val Lys Gly Ser Ser Leu
                565                 570                 575

Tyr Thr His Lys Asp Gly Glu Phe Ser Gln Phe Ile Gly Asn Lys Leu
                580                 585                 590

Lys Pro Lys Thr Asn Tyr Val Ile Gln Tyr Ala Ile Lys Gly Arg Pro
                595                 600                 605

Ala Ile Tyr Leu Lys Asn Asn Lys Asp Thr Leu Phe Glu Asp Thr Asn
610                 615                 620

Asn Asn Phe Ser Asp Phe Gln Thr Val Thr Lys Lys Phe Asn Ser Gly
625                 630                 635                 640

Ala Asn Pro Ser Glu Ile Tyr Leu Leu Phe Lys Asn Gln Gly Glu Tyr
                645                 650                 655

Glu Ala Trp Gly Asn Asn Phe Ile Ile Leu Glu Ile Lys Ser Leu Glu
                660                 665                 670

Leu Leu Pro Gln Met Leu Lys Pro Glu Asp Trp Ile Pro Ser Gly Asn
                675                 680                 685

Val Gln Met Lys Asp Glu Gly Arg Leu Glu Ile Leu Gly Asp Gly Tyr
            690                 695                 700

Phe Lys Gln Phe Ile Lys Leu Gln Asn Asp Ser Thr Tyr His Leu Arg
705                 710                 715                 720

Leu Ser Val Lys Gly Thr Gly Arg Val Ser Ile Ile Asp Glu Ser Asn
                725                 730                 735

Tyr Leu Phe Phe Val Asn Ile Lys Asp Glu Asp Phe Thr Ser Val Ile
                740                 745                 750

Lys Asn Arg Ser Ser Glu Gly Asp Cys Phe Ile Ala Leu Glu Gly Ser
                755                 760                 765

Tyr Val Glu Asn Ser Ser Thr Ile Phe Ser Ser Val Ser Ile Val Lys
            770                 775                 780

Glu
785

<210> SEQ ID NO 42
<211> LENGTH: 2427
<212> TYPE: DNA
<213> ORGANISM: Artificial
<220> FEATURE:
<223> OTHER INFORMATION: A synthetic nucleotide sequence which encodes
    TIC2160 with an N-terminal His tag (TIC2160_MGSSHHHHHH, SEQ ID
    NO: 12).

<400> SEQUENCE: 42
atgggcagca gccatcatca tcatcatcac caccaaagga tgataattgt ggataataat    60
aaattaaatg taagagcttt accaagcttt attgattatt ttaacggtat ttatggattt   120
gccactggta tcaaagatat tatgggaatg attttaaaa cagatacagg tggtagtaat   180
ttaacattag atgagatttt aaagaatcaa aatttactaa atgatatctc aggtaagctc   240

```
gatggaatta atggagattt aggggatctt attgcacaag ggaacttgaa ttcagaatta    300
gctaaggaat tgctaaaaat ctctaatgag cagaatcaaa tgttaaatca tgttaatgct    360
caacttaatg caatcaattc aacacttaat atatatcttc caaaaattac atctatgtta    420
aatgaggtga tgaagcaaaa ccatgtttta agtctacaaa tagaatttct tagtaagcaa    480
ttgcaggaaa tttcagataa acttgatatt atcaacttaa acgtattgat taactctaca    540
ttaacagaga ttactcctgc ttatcaacgt attaaatatg taaacgaaaa atttgatgaa    600
ttgacttcta ctgtagagaa aaatccaaaa tcatatcaag ataacgttac taaagaagtt    660
attgaaaact taaatgagct aactgagttg gcgaaaagtg ttaccaaaaa tgatatggat    720
agttttgaat tttatcttca aactttccat gatgtaatga ctggaaataa tttattcggc    780
cgctcagcat taaaaactgc ttcagaatta attacaaaag aaaatgtcac gacaagggga    840
agtgagatag gaaaagttta taatttctta attgttttaa cttctttaca agcaaaagct    900
tttctcactt taactgcatg tcgaaagtta ttaggtttaa cagatatcga ttatactcaa    960
attatgaatc atcatataga tggtcaaaaa agagaatttc gtattaatat tcttccaaca   1020
ctttctaata atttttctaa tcctagttat tcaaaaaata gaggaagtga tatcgatgat   1080
ccaattgttg tgttagaagc agcacctgga tatgccttaa taggatttga aattctaaac   1140
gatccacttc caattttaaa aggatatcag gctaggttaa aaccaaatta tcaagttgac   1200
agggagtcga tgtcagaaac gatttatggg gacattcata aattattttg cccaaaacag   1260
ctggagcaaa aatattatat taaagatatt gaatttcctg agggctatgt aattactaaa   1320
atcgtttttg aaaaaaggct aaatcaattg gggtatgagg taacagcaaa tttttatgac   1380
ccgtctacag gaagtatcga tttaaataag gttaaagtag aatcttggaa ggaaaagtct   1440
tgcgaggagg attcctgcga agatgagtat agtattataa aggccgaaac ggatggcatt   1500
tatatgccat taggcgtagt aagtgagact ttttaaccc ctatttatgg ttttggatta   1560
acagttgacg aaaaaaatca aaaaataact ttaacaggta atcctatttt acgtgaatcc   1620
ttactagaaa cagacttact taacaatgaa acatatttaa ttgcttcacc agacggttat   1680
attagtagta ttgtagaaaa ctggaatata acatcagata atactgggtc ttggagagca   1740
aataataata atgcatttgt cgataaggca gatactataa aaggatcaag ttctctgtat   1800
actcataaag atggggaatt ctcgcaattt attggaaata agctaaaacc taaaactaat   1860
tatgttattc aatatgttat aaaaggaaga cctgctattt atttaaaaaa taataaagat   1920
actttatttg aggataccaa aaataacttt agcgattttc agactgtaac taaaaaattc   1980
aattcaggag taaatccttc ggaaatttat ttccttttta aaaatcaaag tgaatacgaa   2040
gcctggggaa ataactttat tattttagaa attaaatcgc ttgaattctt gccacaaatg   2100
ctgaagcctg aggattggat accatcagga aatgtgcaaa tgaaagatgg aggacgccta   2160
gagattttgg gagatggtta ttttaaacaa ttcattaaat tggaaaatga ttcaacctat   2220
catctaagat tatctgttaa gggaacaggt agggtatcta taattgatga atctaaatat   2280
ttactttttg taaatgttaa ggatgaagat cttactagag ttattaaaaa tacctcttca   2340
aagggtgagt gttttatagc tcttgagggt acttatgtag aaaattcaag tactattttc   2400
tctaatgtat ctattgttaa agagtaa                                       2427
```

<210> SEQ ID NO 43
<211> LENGTH: 2397
<212> TYPE: DNA
<213> ORGANISM: Artificial
<220> FEATURE:
<223> OTHER INFORMATION: A synthetic nucleotide sequence which encodes
the TIC2160 variant, TIC2160_Del8 with an N-terminal His tag
(TIC2160_Del8_MGSSHHHHHHH, SEQ ID NO: 9)

<400> SEQUENCE: 43

```
atgggcagca gccatcatca tcatcatcac caccaaagga tgataattgt ggataataat     60
aaattaaatg taagagcttt accaagcttt attgattatt ttaacggtat ttatggattt    120
gccactggta tcaaagatat tatgggaatg attttttaaaa cagatacagg tggtagtaat   180
ttaacattag atgagatttt aaagaatcaa aatttactaa atgatatctc aggtaagctc    240
gatggaatta atggagattt aggggatctt attgcacaag gaacttgaa ttcagaatta     300
gctaaggaat tgctaaaaat ctctaatgag cagaatcaaa tgttaaatca tgttaatgct    360
caacttaatg caatcaattc aacacttaat atatatcttc aaaaattac atctatgtta    420
aatgaggtga tgaagcaaaa ccatgtttta agtctacaaa tagaatttct tagtaagcaa    480
ttgcaggaaa tttcagataa acttgatatt atcaacttaa acgtattgat taactctaca    540
ttaacagaga ttactcctgc ttatcaacgt attaaatatg taaacgaaaa atttgatgaa    600
ttgacttcta ctgtagagaa aaatccaaaa tcatatcaag ataacgttac taaagaagtt    660
attgaaaact taaatgagct aactgagttg gcgaaaagtg ttaccaaaaa tgatatggat    720
agttttgaat tttatcttca aactttccat gatgtaatga ctggaaataa tttattcggc    780
cgctcagcat taaaaactgc ttcagaatta attacaaaag aaaatgtcac gacaagggga    840
agtgagatag gaaaagttta taatttctta attgttttaa cttctttaca agcaaaagct    900
tttctcactt taactgcatg tcgaaagtta ttaggtttaa cagatatcga ttatactcaa    960
attatgaatc atcatataga tggtcaaaaa agagaatttc gtattaatat tcttccaaca   1020
cttttctaata attttttctaa tcctagttat tcaaaaaata gaggaagtga tatcgatgat  1080
ccaattgttg tgttagaagc agcacctgga tatgccttaa taggatttga aattctaaac   1140
gatccacttc caatttttaaa aggatatcag gctaggttaa aaccaaatta tcaagttgac  1200
agggagtcga tgtcagaaac gatttatggg gacattcata aattattttg cccaaaacag   1260
ctggagcaaa aatattatat taaagatatt gaatttcctg agggctatgt aattactaaa   1320
atcgttttg aaaaaaggct aaatcaattg gggtatgagg taacagcaaa ttttttatgac   1380
ccgtctacag gaagtatcga tttaaataag gttaaagtag aatcttctga agctgagtat  1440
agtattataa aggccgaaac ggatggcatt tatatgccat taggcgtagt aagtgagact   1500
ttttaacccc ctatttatgg ttttggatta acagttgacg aaaaaaatca aaaataact    1560
ttaacaggta atcctatttt acgtgaatcc ttactagaaa cagacttact taacaatgaa  1620
acatatttaa ttgcttcacc agacggttat attagtagta ttgtagaaaa ctggaatata  1680
acatcagata atactgggtc ttggagagca aataataata atgcatttgt cgataaggca  1740
gatactataa aaggatcaag ttctctgtat actcataaag atgggaatt ctcgcaattt    1800
attggaaata agctaaaacc taaaactaat tatgttattc aatatgttat aaaaggaaga  1860
cctgctattt atttaaaaaa taataaagat acttttattg aggataccaa aaataacttt   1920
agcgattttc agactgtaac taaaaaattc aattcaggag taaatccttc ggaaatttat   1980
ttcctttta aaaatcaaag tgaatacgaa gcctgggaa ataactttat tattttagaa    2040
attaaatcgc ttgaattctt gccacaaatg ctgaagcctg aggattggat accatcagga  2100
aatgtgcaaa tgaaagatgg aggacgccta gagattttgg gagatggtta ttttaaacaa  2160
```

```
ttcattaaat tggaaaatga ttcaacctat catctaagat tatctgttaa gggaacaggt    2220
agggtatcta taattgatga atctaaatat ttactttttg taaatgttaa ggatgaagat    2280
cttactagag ttattaaaaa tacctcttca aagggtgagt gttttatagc tcttgagggt    2340
acttatgtag aaaattcaag tactattttc tctaatgtat ctattgttaa agagtaa      2397
```

<210> SEQ ID NO 44
<211> LENGTH: 11
<212> TYPE: PRT
<213> ORGANISM: Artificial
<220> FEATURE:
<223> OTHER INFORMATION: Amino acid sequence of an N-terminal HIS tag

<400> SEQUENCE: 44

```
Met Gly Ser Ser His His His His His His His
1               5                   10
```

PROTEINS TOXIC OR INHIBITORY TO LEPIDOPTERAN INSECTS

REFERENCE TO RELATED APPLICATIONS

This application claims the benefit of U.S. provisional application Ser. No. 62/064,998, filed on Oct. 16, 2014, which is incorporated herein by reference in its entirety.

INCORPORATION OF SEQUENCE LISTING

The file named "P34229US02_SEQ.txt" containing the Sequence Listing was created on Oct. 14, 2015. This file is 191,472 bytes (measured in MS-Windows), is contemporaneously filed by electronic submission (using the United States Patent Office EFS-Web filing system), and is incorporated into this application by reference in its entirety.

FIELD OF THE INVENTION

This invention generally relates to the field of insect inhibitory proteins. A novel class of proteins exhibiting insect inhibitory activity against agriculturally-relevant pests of crop plants and seeds are disclosed. In particular, the disclosed class of proteins is insecticidally active against agriculturally-relevant pests of crop plants and seeds, particularly Lepidopteran species of insect pests. Plants, plant parts, and seeds containing a polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices.

Insects, particularly insects within the order Lepidoptera, are considered a major cause of damage to field crops, thereby decreasing crop yields over infested areas. Lepidopteran pest species which negatively impact agriculture include, but are not limited to, *Helicoverpa zea, Ostrinia nubilalis, Diatraea saccharalis, Diatraea grandiosella, Anticarsia gemmatalis, Spodoptera frugiperda, Spodoptera exigua, Agrotis ipsilon, Trichoplusia ni, Chrysodeixis includens, Heliothis virescens, Plutella xylostella, Pectinophora gossypiella, Helicoverpa armigera, Elasmopalpus lignosellus, Striacosta albicosta* and *Phyllocnistis citrella*.

Strains of the bacterium *Bacillus thuringiensis* (Bt) have historically been used as a source for proteins which exhibit pesticidal activity. For the past seventy years, Bt-derived toxin proteins have been employed in various agricultural applications to preserve agriculturally important plants and increase yields. Bt-derived insect inhibitory proteins are used to control agriculturally-relevant pests of crop plants by mechanical methods, such as spraying to disperse microbial formulations containing various Bt strains onto plant surfaces, and by using genetic transformation techniques to produce transgenic plants and seeds expressing Bt toxin protein.

The use of transgenic plants expressing Bt toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The expanded use of transgenic insect-protected crops and the limited number of commercially available Bt toxin proteins is creating a selection pressure for alleles that impart resistance to the currently-utilized Bt proteins. The development of resistance in target pests to Bt toxin proteins undermines the effectiveness and advantages of this technology. Such advantages include increased crop yields, reduction in chemical pesticide use, and reduction in the costs and labor associated with chemical pesticide use.

The development of new forms of toxin proteins is central to managing the increase in insect resistance to transgenic crops expressing Bt toxin proteins. New protein toxins with improved efficacy and which exhibit control over a broader spectrum of susceptible insect species will reduce the number of surviving insects which can develop resistance alleles. In addition, two or more transgenic toxins, both toxic to the same insect pest and displaying different modes of action when expressed in a single plant, further reduces the probability of the development of resistance to either toxin by the target insect species.

Consequently, there is a critical need to discover and develop insecticidally effective toxin proteins with improved insecticidal properties such as increased efficacy against a broader spectrum of target insect pest species and different modes of action compared to proteins known in the art. A novel protein toxin TIC2160 is disclosed herein along with other similar toxin proteins, variant proteins, and exemplary recombinant proteins similar to TIC2160, that each exhibit insecticidal activity against significant target Lepidopteran pest species.

SUMMARY OF THE INVENTION

The present invention provides a novel class of insect inhibitory polypeptides (insect toxic proteins) which are shown to exhibit inhibitory activity against several Lepidopteran pests of crop plants. Each of the proteins can be used alone or in combination with each other and with other Bt proteins and toxic agents in formulations and in planta, providing alternatives to known Bt proteins and insecticide chemistries.

In one embodiment, a recombinant nucleic acid molecule is disclosed comprising a heterologous promoter fragment operably linked to a polynucleotide segment encoding a pesticidal protein or fragment thereof, wherein said pesticidal protein or pesticidal fragment thereof (a) comprises the amino acid sequence of SEQ ID NO: 2, SEQ ID NO: 35, SEQ ID NO: 37, SEQ ID NO: 39, SEQ ID NO: 10, SEQ ID NO: 41, SEQ ID NO: 23, SEQ ID NO: 25, SEQ ID NO: 27, SEQ ID NO: 29, SEQ ID NO: 31, SEQ ID NO: 33, or SEQ ID NO: 4; or (b) comprises an amino acid sequence having at least from about 81% to about 100% amino acid sequence identity, or any fraction percentage point between 81% and 100%, to the proteins selected from the group consisting of SEQ ID NO: 2, SEQ ID NO: 35, SEQ ID NO: 37, SEQ ID NO: 39, SEQ ID NO: 10, SEQ ID NO: 41, SEQ ID NO: 23, SEQ ID NO: 25, SEQ ID NO: 27, SEQ ID NO: 29, SEQ ID NO: 31, SEQ ID NO: 33, and SEQ ID NO: 4. In another embodiment, said polynucleotide segment hybridizes to a polynucleotide having the nucleotide sequence of SEQ ID NO: 1, SEQ ID NO: 6, SEQ ID NO: 34, SEQ ID NO: 36, SEQ ID NO: 38, SEQ ID NO: 11, SEQ ID NO: 40, SEQ ID NO: 22, SEQ ID NO: 24, SEQ ID NO: 26, SEQ ID NO: 28, SEQ ID NO: 30, SEQ ID NO: 32, SEQ ID NO: 3, or SEQ ID NO: 5 under hybridization conditions of 68° C., followed by washing at 68° C., in 2×SSC containing 0.1% SDS; or (b) said recombinant nucleic acid molecule is in operable linkage with a vector, and said vector is selected from the group consisting of a plasmid, phagemid, bacmid, cosmid, and a bacterial or yeast artificial chromosome. The recombinant nucleic acid molecule can comprise a sequence that functions to express the pesticidal protein in a plant; or is expressed in a plant cell to produce a pesticidally effective amount of pesticidal protein.

In another embodiment, host cells are provided which contain at least one recombinant nucleic acid molecule disclosed herein, wherein the host cell is selected from the group consisting of a bacterial, a yeast, and a plant cell. Bacterial host cells include at least species such as *Agrobacterium, Rhizobium, Bacillus, Brevibacillus, Escherichia, Pseudomonas, Klebsiella*, and *Erwinia*. The *Bacillus* species is a *Bacillus cereus* or a *Bacillus thuringiensis*, the *Brevibacillus* is a *Brevibacillus laterosperous*, and said *Escherichia* is an *Escherichia coli*. Yeast host cells include at least *Pichya* and *Saccharomyces* species. Plant host cells include at least dicotyledonous plant cells and monocotyledonous plant cells, and as applicable, further include at least an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cells.

In another embodiment, the pesticidal protein exhibits activity against an insect species of the order Lepidoptera, including Velvet bean caterpillar, Sugarcane borer, Lesser cornstalk borer, Corn earworm, Tobacco budworm, Soybean looper, Black armyworm, Southern armyworm, Fall armyworm, Beet armyworm, Old World bollworm, Cabage Looper, Wester bean cutworm, Oriental leaf worm, Pink bollworm, Black cutworm, Southwestern corn Borer, Tobacco budworm, and European corn borer.

Also provided are plants comprising a recombinant nucleic acid molecule comprising a polynucleotide segment corresponding to a heterologous promoter operably linked to a segment encoding a pesticidal protein or pesticidal fragment thereof, wherein: (a) said pesticidal protein or pesticidal fragment thereof comprises the amino acid sequence of SEQ ID NO: 2, SEQ ID NO: 35, SEQ ID NO: 37, SEQ ID NO: 39, SEQ ID NO: 10, SEQ ID NO: 41, SEQ ID NO: 23, SEQ ID NO: 25, SEQ ID NO: 27, SEQ ID NO: 29, SEQ ID NO: 31, SEQ ID NO: 33, or SEQ ID NO: 4; or (b) said pesticidal protein or pesticidal fragment thereof comprises an amino acid sequence having at least from about 81% to about 100% amino acid sequence identity, or any fraction percentage point between 81% and 100%, to the proteins selected from the group consisting of SEQ ID NO: 2, SEQ ID NO: 35, SEQ ID NO: 37, SEQ ID NO: 39, SEQ ID NO: 10, SEQ ID NO: 41, SEQ ID NO: 23, SEQ ID NO: 25, SEQ ID NO: 27, SEQ ID NO: 29, SEQ ID NO: 31, SEQ ID NO: 33, and SEQ ID NO: 4; or (c) said polynucleotide segment hybridizes under stringent hybridization conditions to a polynucleotide having the nucleotide sequence of SEQ ID NO: 1, SEQ ID NO: 6, SEQ ID NO: 34, SEQ ID NO: 36, SEQ ID NO: 38, SEQ ID NO: 11, SEQ ID NO: 40, SEQ ID NO: 22, SEQ ID NO: 24, SEQ ID NO: 26, SEQ ID NO: 28, SEQ ID NO: 30, SEQ ID NO: 32, SEQ ID NO: 3, or SEQ ID NO: 5 under hybridization conditions of 68° C., followed by washing at 68° C., in 2×SSC containing 0.1% SDS; or (d) said plant exhibits a detectable amount of said pesticidal protein, wherein the pesticidal protein is chosen from the group consisting of SEQ ID NO: 2, SEQ ID NO: 35, SEQ ID NO: 37, SEQ ID NO: 39, SEQ ID NO: 10, SEQ ID NO: 41, SEQ ID NO: 23, SEQ ID NO: 25, SEQ ID NO: 27, SEQ ID NO: 29, SEQ ID NO: 31, SEQ ID NO: 33, and SEQ ID NO: 4.

In one embodiment, the plant is either a dicotyledonous plant or a monocotyledonous plant. In another embodiment, the plant is further selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In a further embodiment, seeds comprising the recombinant nucleic acid molecules are disclosed.

In another embodiment, an insect inhibitory composition is provided comprising the recombinant nucleic acid molecules as set forth herein. The insect inhibitory composition can further comprise a nucleotide sequence encoding at least one other pesticidal agent that is different from said pesticidal protein. In certain embodiments, the at least one other pesticidal agent is selected from the group consisting of an insect inhibitory protein, an insect inhibitory dsRNA molecule, and an ancillary protein. The at least one other pesticidal agent in the insect inhibitory composition exhibits activity against one or more pest species of the orders Lepidoptera, Coleoptera, Hemiptera, Homoptera, or Thysanoptera. The at least one other pesticidal agent in the insect inhibitory composition is selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC3131, VIP3A, VIP3B, VIP3Ab, AXMI-001, AXMI-002, AXMI-030, AXMI-035, AXMI-036, AXMI-045, Axmi52, Axmi58, Axmi88, Axmi97, Axmi102, Axmi112, Axmi117, Axmi100, AXMI-115, AXMI-113, and AXMI-005, AXMI134, AXMI-150, AXMI171, AXMI-184, axmi196, axmi204, axmi207, axmi209, Axmi205, AXMI218, AXMI220, AXMI221z, AXMI222z, AXMI223z, AXMI224z and AXMI225z, AXMI238, AXMI270, AXMI279, AXMI345, AXMI-R1 and variants thereof, IP3 and variants thereof, DIG-3, DIG-5, DIG-10 and a DIG-11 protein.

Commodity products are provided comprising a detectable amount of the recombinant nucleic acid molecules disclosed herein. Such commodity products include commodity corn which may be bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

Also contemplated is a method of producing seed comprising one or more of the recombinant nucleic acid molecules disclosed herein. The method includes planting at least one such seed; growing a plant from the seed; and harvesting progeny seed from the plant, wherein the harvested seed comprises the one or more recombinant nucleic acid molecules.

In another embodiment, a plant resistant to insect infestation is provided. The cells of said plant optionally comprise: (a) a recombinant nucleic acid molecule encoding an insecticidally effective amount of a pesticidal protein as set forth in SEQ ID NO: 2, SEQ ID NO: 35, SEQ ID NO: 37, SEQ ID NO: 39, SEQ ID NO: 10, SEQ ID NO: 41, SEQ ID NO: 23, SEQ ID NO: 25, SEQ ID NO: 27, SEQ ID NO: 29, SEQ ID NO: 31, SEQ ID NO: 33, or SEQ ID NO: 4; or (b) an insecticidally effective amount of a protein comprising an amino acid sequence having at least 81%, or 85%, or 90%, or 95%, or about 100% amino acid sequence identity to SEQ ID NO: 2, SEQ ID NO: 35, SEQ ID NO: 37, SEQ ID NO: 39, SEQ ID NO: 10, SEQ ID NO: 41, SEQ ID NO: 23, SEQ ID NO: 25, SEQ ID NO: 27, SEQ ID NO: 29, SEQ ID NO: 31, SEQ ID NO: 33, or SEQ ID NO: 4.

Also disclosed are methods for controlling a Lepidopteran species pest, and controlling a Lepidopteran species pest infestation of a plant, particularly a crop plant. The method will comprise contacting the pest with an insecticidally effective amount of a pesticidal proteins as set forth in SEQ ID NO: 2, SEQ ID NO: 35, SEQ ID NO: 37, SEQ ID NO: 39, SEQ ID NO: 10, SEQ ID NO: 41, SEQ ID NO: 23, SEQ ID NO: 25, SEQ ID NO: 27, SEQ ID NO: 29, SEQ ID NO: 31, SEQ ID NO: 33, or SEQ ID NO: 4; or contacting the pest with an insecticidally effective amount of one or more pesticidal proteins comprising an amino acid sequence having at least 81%, or 85%, or 90%, or 95%, or about 100% amino acid sequence identity to SEQ ID NO: 2, SEQ ID NO: 35, SEQ ID NO: 37, SEQ ID NO: 39, SEQ ID NO: 10, SEQ ID NO: 41, SEQ ID NO: 23, SEQ ID NO: 25, SEQ ID NO: 27, SEQ ID NO: 29, SEQ ID NO: 31, SEQ ID NO: 33, or SEQ ID NO: 4.

BRIEF DESCRIPTION OF THE SEQUENCES

SEQ ID NO: 1 is the native nucleotide sequence encoding a TIC2160 toxin protein obtained from the *Bacillus thuringiensis* (Bt) species EG8781.

SEQ ID NO: 2 is the amino acid sequence of a TIC2160 toxin protein.

SEQ ID NO: 3 is the native nucleotide sequence encoding a TIC3244 toxin protein obtained from the *Bacillus thuringiensis* (Bt) species EG8639.

SEQ ID NO: 4 is the amino acid sequence of a TIC3244 toxin protein.

SEQ ID NO: 5 is an artificial nucleotide sequence encoding a TIC2160 toxin protein designed for expression in a plant cell.

SEQ ID NO: 6 is an artificial nucleotide sequence encoding a TIC2160 protein toxin designed for expression in a plant cell.

SEQ ID NO: 7 is an artificial nucleotide sequence encoding a TIC3244 toxin protein designed for expression in a plant cell.

SEQ ID NO: 8 is an artificial nucleotide sequence encoding a TIC2160 variant toxin protein, TIC2160_De18.

SEQ ID NO: 9 is the amino acid sequence of a His-tagged TIC2160 variant toxin protein, TIC2160_De18_MGSSHHHHHHH.

SEQ ID NO: 10 is the amino acid sequence of a TIC2160 variant toxin protein, TIC2160_De18.

SEQ ID NO: 11 is an artificial nucleotide sequence encoding TIC2160_De18 designed for expression in a plant cell.

SEQ ID NO: 12 is the amino acid sequence of a His-tagged TIC2160 protein, TIC2160 MGSSHHHHHHH.

SEQ ID NO: 13 is an artificial nucleotide sequence (TIC2160 forward primer) for use as a probe or primer that corresponds to nucleotide positions 1 to 27 as set forth in SEQ ID NO: 1.

SEQ ID NO: 14 is an artificial nucleotide sequence (TIC2160 reverse primer) for use as a probe or primer that corresponds to the reverse complement of nucleotide positions 2370 to 2396 as set forth in SEQ ID NO: 1.

SEQ ID NO: 15 is an artificial nucleotide sequence (TIC2160 forward primer seq1) for use as a probe or primer that corresponds to nucleotide positions 517 to 539 as set forth in SEQ ID NO: 1.

SEQ ID NO: 16 is an artificial nucleotide sequence (TIC2160 forward primer seq2) for use as a probe or primer that corresponds to nucleotide positions 1350 to 1371 as set forth in SEQ ID NO: 1.

SEQ ID NO: 17 is an artificial nucleotide sequence (TIC2160 reverse primer seq3) for use as a probe or primer that corresponds to nucleotide positions 1350 to 1371 as set forth in SEQ ID NO: 1.

SEQ ID NO: 18 is an artificial nucleotide sequence encoding a TIC2160 variant toxin protein (Variant-a-058).

SEQ ID NO: 19 is the amino acid sequence of the TIC2160 variant toxin protein, Variant-a-058.

SEQ ID NO: 20 is an artificial nucleotide sequence encoding a TIC2160 variant toxin protein, Variant-a-145.

SEQ ID NO: 21 is the amino acid sequence of a TIC2160 variant toxin protein, Variant-a-145.

SEQ ID NO: 22 is an artificial nucleotide sequence encoding a TIC2160 variant toxin protein, TIC2160_13, designed for expression in a plant cell.

SEQ ID NO: 23 is the amino acid sequence of a TIC2160 variant toxin protein, TIC2160_13.

SEQ ID NO: 24 is an artificial nucleotide sequence encoding a TIC2160 variant toxin, TIC2160_14, designed for expression in a plant cell.

SEQ ID NO: 25 is the amino acid sequence of a TIC2160 variant toxin protein, TIC2160_14.

SEQ ID NO: 26 is an artificial nucleotide sequence encoding a TIC2160 variant toxin protein, TIC2160_15, designed for expression in a plant cell.

SEQ ID NO: 27 is the amino acid sequence of a TIC2160 variant toxin protein, TIC2160_15.

SEQ ID NO: 28 is an artificial nucleotide sequence encoding a TIC2160 variant toxin protein, TIC2160_16, designed for expression in a plant cell.

SEQ ID NO: 29 is the amino acid sequence of a TIC2160 variant toxin protein, TIC2160_16, encoded by SEQ ID NO: 28.

SEQ ID NO: 30 is an artificial nucleotide sequence encoding a TIC2160 variant toxin protein, TIC2160_17, designed for expression in a plant cell.

SEQ ID NO: 31 is the amino acid sequence of a TIC2160 variant toxin protein TIC2160_17 encoded by SEQ ID NO: 30.

SEQ ID NO: 32 is an artificial nucleotide sequence encoding a TIC2160 variant toxin protein, TIC2160_18, designed for expression in a plant cell.

SEQ ID NO: 33 is the amino acid sequence of a TIC2160 variant toxin protein, TIC2160_18.

SEQ ID NO: 34 is an artificial nucleotide sequence encoding a TIC2160 variant toxin protein, TIC2160_20, designed for expression in a plant cell.

SEQ ID NO: 35 is the amino acid sequence of a TIC2160 variant toxin protein, TIC2160_20.

SEQ ID NO: 36 is an artificial nucleotide sequence encoding a TIC2160 variant toxin protein, TIC2160_21, designed for expression in a plant cell.

SEQ ID NO: 37 is the amino acid sequence of a TIC2160 variant toxin protein, TIC2160_21.

SEQ ID NO: 38 is an artificial nucleotide sequence encoding a TIC2160 variant toxin protein, TIC5420_13, designed for expression in a plant cell.

SEQ ID NO: 39 is the amino acid sequence of a TIC2160 variant toxin protein, TIC5420_13.

SEQ ID NO: 40 is an artificial nucleotide sequence encoding a TIC2160 variant toxin protein, TIC5420_a, from the ORF as set forth at nucleotide positions 1-2355, and is designed for expression in a plant cell.

SEQ ID NO: 41 is the amino acid sequence of a TIC2160 variant toxin protein, TIC5420_a.

SEQ ID NO: 42 is an artificial nucleotide sequence encoding TIC2160_MGSSHHHHHHH.

SEQ ID NO: 43 is an artificial nucleotide sequence encoding TIC2160_De18_MGSSHHHHHHH.

SEQ ID NO: 44 is the amino acid sequence of an N-terminal HIS tag.

DETAILED DESCRIPTION OF THE INVENTION

New toxin proteins are needed for control of plant pest infestations by Lepidopteran insects. New toxins should exhibit different modes of action (MOA) compared to toxin proteins currently used in commercial embodiments, and should preferably exhibit broad spectrum biological activity. Disclosed in this application are insecticidal proteins exemplified by TIC2160 and synthetic or artificial variants of TIC2160 which address the need for an alternative MOA and exhibit activity against a broad spectrum of Lepidopteran insect pests.

Reference herein to TIC2160, or to "TIC2160 protein," "TIC2160 protein toxins," "TIC2160 toxin proteins," "TIC2160-related toxins," "TIC2160-related protein toxin class or family," "TIC2160-related toxin proteins," "TIC2160-related toxin polypeptides", "TIC2160-related pesticidal proteins", "variants of TIC2160", or "TIC2160 variants" and the like, as used in this application, refer to any novel insect inhibitory protein that comprises, that consists, that is substantially homologous to, that is similar to, or that is derived from any insect inhibitory polypeptide sequence of TIC2160 (SEQ ID NO: 2) and insect inhibitory segments thereof, or combinations thereof, that confer activity against Lepidopteran pests, including any protein exhibiting insect inhibitory activity if alignment of such protein with TIC2160 as set forth in SEQ ID NO: 2 results in at least about 81%, 82%, 83%, 84%, 85%, 86%, 87%, 88%, 89%, 90%, 91%, 92%, 93%, 94%, 95%, 96%, 97%, 98%, 99%, or about 100% amino acid sequence identity (or any fraction percentage in this range).

The term "segment" or "fragment" is used in this application to describe consecutive amino acid or nucleic acid sequences that are shorter than the complete amino acid or nucleic acid sequence describing a TIC2160 protein. A segment or fragment exhibiting insect inhibitory activity is also disclosed in this application if alignment of such segment or fragment, with the corresponding section of the TIC2160 protein set forth in SEQ ID NO: 2, results in at least about 81%, 82%, 83%, 84%, 85%, 86%, 87%, 88%, 89%, 90%, 91%, 92%, 93%, 94%, 95%, 96%, 97%, 98%, 99%, or about 100% amino acid sequence identity (or any fraction percentage in this range) between the segment or fragment and the corresponding section of the TIC2160 protein.

Reference in this application to the term "active" or "activity," "pesticidal activity," "insecticidal activity", or "insect-inhibitory activity" refers to efficacy of a toxic agent, such as a protein toxin, in inhibiting a pest. Pesticidal activity is intended to include the result of providing a toxic protein to a pest where the exposure of the pest to the toxic protein results in morbidity, mortality, or stunting. Pesticidal activity also includes repulsion of the pest from the plant, a tissue of the plant, a plant part, seed, plant cells, or from the particular geographic location where the plant may be growing, as a result of providing a toxic protein in or on the plant. In general, pesticidal activity refers to the ability of a toxic protein to be effective in inhibiting the growth, development, viability or fecundity of a particular target pest, particularly an insect pest, including but not limited to insects of the order Lepidoptera. The toxic protein can be produced by the plant or can be applied to the plant or to the environment within the location where the plant is located.

A pesticidally effective amount of a toxic protein, when provided in the diet of a target pest, exhibits pesticidal activity when the toxic protein contacts the pest. A toxic agent can be a pesticidal protein or one or more chemical agents known in the art. Insecticidal chemical agents and insecticidal protein agents can be used alone or in combinations with each other. Chemical agents include but are not limited to organochlorides, organophosphates, carbamates, pyrethroids, neonicotinoids, ryanoids, and dsRNA molecules targeting specific genes for suppression in a target pest. Insecticidal protein agents include the protein toxins set forth in this application, as well as other proteinaceous toxic agents including those that target Lepidopteran, as well as protein toxins that are used to control other plant pests such as Cry proteins available in the art for use in controlling Coleopteran, Hemipteran, Homopteran, or Thysanopteran species.

It is intended that reference to a pest, particularly a pest of a crop plant, means insect pests of crop plants, particularly those that are controlled by the TIC2160-related protein toxin class. However, reference to a pest can also include other pests such as Coleopteran, Hemipteran, Homopteran, or Thysanopteran plant insect pests, as well as nematodes and fungi when toxic agents targeting these pests are co-localized or present together with one or more proteins of the TIC2160-related protein toxin class.

The individual proteins which comprise the TIC2160-related protein class are related by common function and exhibit insecticidal activity towards insect pests from the Lepidoptera insect species, including adults, pupae, larvae, and neonates. The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), Southern armyworm (*Spodoptera eridania*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leaf worm), *Archips argyrospila* (fruit tree leaf roller), *Archips rosana* (European leafroller) and other *Archips* species, *Chilo suppressalis* (Asiatic rice borer, or rice stem borer), *Cnaphalocrocis medinalis* (rice leaf roller), *Crambus caliginosellus* (corn root webworm), *Crambus teterrellus* (bluegrass webworm), *Diatraea grandiosella* (southwestern corn borer), *Diatraea saccharalis* (surgarcane borer), *Earias insulana* (spiny bollworm), *Earias vittella* (spotted bollworm), *Helicoverpa armigera* (American bollworm), *Helicoverpa zea* (corn earworm, or soybean pod worm, or cotton bollworm), *Heliothis virescens* (tobacco budworm), *Herpetogramma licarsisalis* (sod webworm), *Lobesia botrana* (European grape vine moth), *Phyllocnistis citrella* (citrus leafminer), *Pieris brassicae* (large white butterfly), *Pieris rapae* (imported cabbageworm, or small white butterfly), *Plutella xylostella* (diamondback moth), *Spodoptera exigua* (beet armyworm), *Spodoptera litura* (tobacco cutworm, cluster caterpillar), and *Tuta absoluta* (tomato leafminer).

Reference in this application to an "isolated DNA molecule," or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding a *Bacillus thuringiensis* (Bt) insecticidal protein or any naturally occurring insecticidal variant of that protein would be an isolated nucleotide sequence so long as the nucleotide sequence was not within the DNA of the Bt bacterium from which the sequence encoding the protein is naturally found. An synthetic nucleotide sequence encoding the amino acid sequence of the naturally occurring Bt insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

An open reading frame (ORF) encoding TIC2160 was discovered with DNA obtained from a Bt strain EG8781. High throughput sequencing and bioinformatics were used to screen Bt genomes for TIC2160-related protein-encoding genes, such as the ORF for TIC3244 derived from Bt strain EG8639. Genomes of interest were identified and the respective coding sequences were cloned and expressed in microbial host cells to produce recombinant proteins for use in insect bioassays.

Variants of the TIC2160 protein toxin class were produced by substituting, deleting or inserting amino acids into parent protein sequences, such as TIC2160, and making appropriate changes to the polynucleotides encoding these variants. Multiple rounds of engineering, testing, and selecting of over 500 amino acid sequence variants of TIC2160 resulted in the identification of amino acid residues that may be substituted, inserted or deleted, producing Lepidopteran toxic proteins that exhibit an expanded insect species inhibitory spectrum and improved Lepidopteran inhibitory activity (i.e., more toxic; less protein is required to obtain the same level of mortality) when compared to the spectrum and activity of the baseline protein TIC2160. Neutral amino acid residue substitutions and deletions in TIC2160 that do not change the protein's insect inhibitory spectrum or activity were also identified.

In certain instances, the produced variants in the TIC2160 protein toxin class exhibit an increased Lepidopteran inhibitory activity and target pest species spectrum compared to the activity and target pest species spectrum of the TIC2160 protein (SEQ ID NO: 2). Each of the disclosed TIC2160 toxic protein variants contain at least one, two, three, four, five, six, seven, or eight amino acid substitutions, and can also comprise insertion and deletions of amino acids. These substitutions, deletions and insertions are described with reference to the amino acid sequence positions as numbered according to the amino acid positions of TIC2160_MGSSHHHHHHH (SEQ ID NO: 12) and are presented in Table 4 of Example 3. For example, the exemplary TIC2160 variants Variant-a-058 (SEQ ID NO: 19) and Variant-a-145 (SEQ ID NO: 21), which show improved activity for Fall armyworm, comprise insertions, substitutions or deletions selected from the group consisting of deletion of residues 2 through 11 after residue 1, deletion of residues 12 through 14, insertion of EFCEH after D at position 488, substitution of I at position 15 for M, substitution of D at position 86 for G, substitution of I at position 131 for V, substitution of K at position 145 for M, substitution of E at position 206 for D, substitution of K at position 207 for S or N, substitution of N at position 208 for R or K, substitution of P at position 209 for G or K, substitution of K at position 210 for R or S, substitution of S at position 211 for G, substitution of Q at position 213 for E, substitution of D at position 214 for N, substitution of N at position 215 for D, substitution of T at position 217 for S, substitution of K at position 218 for R, substitution of E at position 219 for Q, substitution of E at position 222 for N, substitution of N at position 223 for E, substitution of N at position 225 for T, substitution of E at position 226 for D, substitution of R at position 261 for K, substitution of K at position 265 for R, substitution of S at position 268 for A, substitution of E at position 269 for Q, substitution of K at position 273 for R, substitution of E at position 274 for N, substitution of N at position 275 for E, substitution of V at position 276 for T, substitution of T at position 277 for V, substitution of Q at position 320 for K, substitution of I at position 321 for T, substitution of E at position 322 for Q, substitution of H at position 324 for Q, substitution of I at position 326 for L, substitution of N at position 344 for S, substitution of E at position 377 for Q, substitution of S at position 465 for N, substitution of D at position 484 for I, substitution of I at position 492 for L, substitution of L at position 547 for V, substitution of I at position 561 for F, substitution of T at position 575 for F, substitution of A at position 590 for E, substitution of I at position 593 for V, substitution of V at position 626 for A, substitution of K at position 647 for N, substitution of V at position 664 for A, substitution of F at position 671 for L, substitution of S at position 677 for G, substitution of F at position 696 for L, substitution of G at position 717 for G, substitution of E at position 735 for Q, substitution of K at position 759 for N, substitution of L at position 762 for F, substitution of V at position 766 for I, substitution of L at position 771 for F, substitution of R at position 773 for S, substitution of T at position 778 for R, substitution of K at position 781 for E, substitution of E at position 783 for D, substitution of T at position 791 for S, and substitution of N at position 802 for S. Other exemplary amino acid insertions, deletions and substitutions are presented in Table 4 of Example 3 below.

Core toxin fragments were processed from the full-length proteins of the TIC2160 toxin protein class. This core toxin processing occurred by incubation with proteolytic enzymes or with insect gut juices, or a combination. The use of non-full-length proteins, or core toxin fragments, of the TIC2160 toxin protein class is contemplated in the disclosure of this application. In addition, the TIC2160 toxin protein class includes functionally equivalent fragments (N- or C-terminal) of the TIC2160-related proteins. The TIC2160 toxin protein class may also be truncated, a process in which one or more amino acids are deleted from the N-terminal end, from the C-terminal end, from positions within the middle of the protein, or using various combinations thereof, so long as the resulting protein exhibits inhibitory activity. These fragments can be naturally occurring or synthetic.

Certain members of the TIC2160 protein toxin class share an N-terminal motif with the sequence MQRMIIVDN. Forward oligonucleotide primers, e.g., SEQ ID NO: 13, hybridize to the minus (−) strand of the DNA sequence encoding for these N-terminal sequences. Certain members of the TIC2160 protein toxin class also share a C-terminal consensus sequence FSNVSIVKE. Reverse oligonucleotide primers, e.g., SEQ ID NO: 14, hybridize to the plus (+) strand of the DNA sequence encoding for the C-terminus sequence of proteins of the present invention. Additional forward and reverse oligonucleotide primers, e.g., SEQ ID NO: 15, SEQ ID NO: 16, SEQ ID NO: 17, hybridize to corresponding minus (−) and plus (+) strands of the DNA sequence encoding for the sequence of certain members of the TIC2160 protein toxin class. Used alone or in combination, as-is or modified, such forward and reserve primers can be used to amplify copies, prime for sequencing, introduce coding substitutions, and/or identify nucleotide sequences encoding for proteins of the TIC2160 protein toxin class.

Through this process, a novel class of proteins which exhibits insect inhibitory activity against Lepidopteran species, the TIC2160 protein toxins, was discovered and is disclosed in this application. The TIC2160 protein toxin class includes TIC2160 and TIC3244 and protein variants derived from TIC2160 and TIC3244. The polypeptides and proteins of the TIC2160 protein toxin class are related by biological toxin activity against Lepidoptera insect pests, by primary structure (conserved amino acid sequence segments or motifs), by length (deduced full-length proteins are about 800 amino acids as full-length), and by size (75-95 kDaltons). The Lepidopteran toxic proteins variants provided herein can be derived from various proteins, including but not limited to, TIC2160 and TIC3244.

Proteins that resemble the TIC2160 protein toxin class can be identified by comparison to each other using various computer based algorithms known in the art. For example, the amino acid identities reported in this application are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson et al (1994) Nucleic Acids Research, 22:4673-4680). Percent amino acid identity is further calculated by the product of 100% multiplied by (amino acid identities/length of subject protein).

It is intended that a query protein exhibiting insect inhibitory activity against a Lepidopteran insect species is member of the TIC2160 protein toxin class if a Clustal W alignment of such query protein with the subject proteins TIC2160 (SEQ ID NO: 2) or TIC3244 (SEQ ID NO: 4) results in at least about (100%×(650/798)=81.45%) between the query and subject proteins; or specifically, at least about 81, 82, 83, 84, 85, 86, 87, 88, 89, 90, 91, 92, 93, 94, 95, 96, 97, 98, 99, 99.1, 99.3, 99.4, 99.5, 99.6, 99.8, 99.9, or 100% amino acid sequence identity between the query and subject proteins, or any fraction percentage in this range.

Exemplary proteins of the TIC2160 protein toxin class, TIC2160 (SEQ ID NO: 2) and TIC3244 (SEQ ID NO: 4), and variants of TIC2160 (TIC2160_De18, SEQ ID NO: 10; TIC2160_13, SEQ ID NO: 23; TIC2160_14, SEQ ID NO: 25; TIC2160_15, SEQ ID NO: 27; TIC2160_16, SEQ ID NO: 29; TIC2160_17, SEQ ID NO: 31; TIC2160_18, SEQ ID NO: 33; TIC2160_20, SEQ ID NO: 35; TIC2160_21, SEQ ID NO: 37; TIC5420_13, SEQ ID NO: 39, and TIC5420_a, SEQ ID NO: 41) were aligned with each other using a Clustal W algorithm. A pair-wise matrix of percent amino acid sequence identities for each pair was created, as reported in Table 1.

TABLE 1

Pair-wise matrix display of exemplary proteins.

| SEQ ID NO: | Y | | | | | |
|---|---|---|---|---|---|---|
| X | 2 | 4 | 25 | 27 | 31 | 33 | 29 |
| 2 | — | 99.9 (797) | 97.6 (779) | 97.5 (778) | 98.6 (787) | 97.9 (781) | 99.2 (792) |
| 4 | 99.9 (797) | — | 97.5 (778) | 97.4 (777) | 98.5 (786) | 97.7 (780) | 99.1 (791) |
| 25 | 97.6 (779) | 97.5 (778) | — | 98.6 (787) | 97.9 (781) | 97.1 (775) | 96.9 (773) |
| 27 | 97.5 (778) | 97.4 (777) | 98.6 (787) | — | 97.7 (780) | 98.5 (786) | 98.2 (784) |
| 31 | 98.6 (787) | 98.5 (786) | 97.9 (781) | 97.7 (780) | — | 99.2 (792) | 97.9 (781) |
| 33 | 97.9 (781) | 97.7 (780) | 97.1 (775) | 98.5 (786) | 99.2 (792) | — | 98.6 (787) |
| 29 | 99.2 (792) | 99.1 (791) | 96.9 (773) | 98.2 (784) | 97.9 (781) | 98.6 (787) | — |
| 37 | 99.2 (792) | 99.1 (791) | 96.9 (773) | 97.7 (780) | 97.9 (781) | 98.1 (783) | 99.5 (794) |
| 35 | 99.9 (797) | 99.7 (796) | 97.5 (778) | 97.6 (779) | 98.5 (786) | 98 (782) | 99.4 (793) |
| 10 | 99.7 (786) | 99.6 (785) | 97.3 (767) | 97.2 (766) | 98.4 (775) | 97.6 (769) | 99 (780) |
| 23 | 98 (783) | 97.9 (782) | 95.6 (764) | 95.5 (763) | 96.6 (772) | 95.9 (766) | 97.2 (777) |
| 39 | 90 (720) | 89.9 (719) | 88.4 (707) | 89.1 (713) | 89.1 (713) | 89.4 (715) | 90.3 (722) |
| 41 | 94.6 (743) | 94.5 (742) | 92.6 (727) | 92.4 (725) | 93.5 (734) | 92.7 (728) | 93.9 (737) |

| SEQ ID NO: | Y | | | | | |
|---|---|---|---|---|---|---|
| X | 37 | 35 | 10 | 23 | 39 | 41 |
| 2 | 99.2 (792) | 99.9 (797) | 98.5 (786) | 98.1 (783) | 90.2 (720) | 93.1 (743) |
| 4 | 99.1 (791) | 99.7 (796) | 98.4 (785) | 98 (782) | 90.1 (719) | 93 (742) |
| 25 | 96.9 (773) | 97.5 (778) | 96.1 (767) | 95.7 (764) | 88.6 (707) | 91.1 (727) |
| 27 | 97.7 (780) | 97.6 (779) | 96 (766) | 95.6 (763) | 89.3 (713) | 90.9 (725) |
| 31 | 97.9 (781) | 98.5 (786) | 97.1 (775) | 96.7 (772) | 89.3 (713) | 92 (734) |
| 33 | 98.1 (783) | 98 (782) | 96.4 (769) | 96 (766) | 89.6 (715) | 91.2 (728) |
| 29 | 99.5 (794) | 99.4 (793) | 97.7 (780) | 97.4 (777) | 90.5 (722) | 92.4 (737) |
| 37 | — | 99.4 (793) | 97.7 (780) | 97.4 (777) | 91 (726) | 92.4 (737) |
| 35 | 99.4 (793) | — | 98.4 (785) | 98 (782) | 90.4 (721) | 93 (742) |
| 10 | 99 (780) | 99.6 (785) | — | 99 (780) | 90.9 (716) | 94.3 (743) |
| 23 | 97.2 (777) | 97.9 (782) | 97.6 (780) | — | 90.7 (725) | 92.2 (737) |
| 39 | 90.8 (726) | 90.1 (721) | 89.5 (716) | 90.6 (725) | — | 94.1 (753) |
| 41 | 93.9 (737) | 94.5 (742) | 94.6 (743) | 93.9 (737) | 95.9 (753) | — |

Table description: Clustal W alignment between (X) and (Y) are reported in a pair-wise matrix. The percent amino acid identity between all pairs is calculated and is represented by the first number in each box. The second number (in parentheses) in each box represents the number of identical amino acids between the pair.

The full-length proteins of the TIC2160 protein toxin class can also be related by primary structure (conserved amino acid motifs) and by length (about 798 amino acids). The full-length proteins from the present invention have a measured mass of about 75-95 kDaltons when run on protein gels under denaturing conditions.

The proteins of the disclosed TIC2160 protein toxin class represent a new class of Bt proteins, exhibiting no greater than 95% amino acid identity to any other Bt protein known in the art. The proteins exhibiting the nearest identity to any of the proteins of the present invention are Axmi335 (WO2013134523), VIP3Ba1 (GI:56069746, ACCESSION AAV70653) and VIP3Aa2 (GenBank accession AAC37037). Axmi335, VIP3Ba1 and VIP3Aa2 were aligned using Clustal W to TIC2160 and TIC3244. The results are of this alignment are shown in Table 2.

TABLE 2

Alignment of TIC2160 and TIC3244 proteins to VIP3B and VIP3A.

|  | TIC2160 (SEQ ID NO: 2) | TIC3244 (SEQ ID NO: 4) |
|---|---|---|
| VIP3Ba1[i] | 596 identities 74.7% | 596 identities 74.2% |
| VIP3Aa2[ii] | 485 identities 61.5% | 484 identities 61.3% |
| Axmi335[iii] | 754 identities 94.3% | 753 identities 94.1% |

Clustal W alignment is reported as number of amino acid identities, and as the percent amino acid identity to the length of TIC2160 (798 AAs) and TIC3244 (798 AAs) respectively.
[i]GenBank accession AAV70653
[ii]GenBank accession AAC37037
[iii]WO2013134523-0002

The TIC2160 proteins disclosed in this application exhibit activity in diet bioassays against Southwestern Corn Borers (SWC, *Diatraea grandiosella*), Sugarcane Borers (SCB, *Diatraea saccharalis*), Corn Earworms (CEW, *Helicoverpa zea*), Fall Armyworms (FAW, *Spodoptera frugiperda*), Cabbage Loopers (CLW, *Trichoplusia ni*), European Corn Borers (ECB, *Ostrinia nubilalis*), Soybean Loopers (SBL, *Chrysodeixis includens*), Western Bean Cutworm (WBC, *Striacosta albicosta*), and Southern Armyworms (SAW, *Spodoptera eridania*). Since *Helicoverpa zea* larva are polyphagous, other common names associated with it include Cotton Bollworm (CBW) and Soybean Podworm (SPW).

As described further in the Examples of this application, polynucleotide sequences encoding TIC2160 toxin proteins were designed for use in plants. Expression cassettes and vectors containing these polynucleotide sequences were constructed and introduced into corn, soybean, cotton and sugarcane plant cells in accordance with transformation methods and techniques known in the art. Transformed cells were regenerated into transformed plants that were observed to be expressing TIC2160 toxin proteins. To test pesticidal activity, bioassays were performed in the presence of Lepidopteran pest larvae using plant leaf disks obtained from the transformed plants.

Table 3 tabulates, by insect species, the insect inhibitory activity of exemplary members of the TIC2160 protein toxin class. The insect inhibitory activity of exemplary members of the TIC2160 protein toxin class is described in more detail in the Examples. Also included in Table 3 are the reported activities for recombinantly expressed Axmi335 and VIP3A proteins. As demonstrated in Table 3, the insecticidal activity of the TIC2160 protein toxin class is unique when compared to Axmi335 and VIP3A reported activities.

TABLE 3

Lepidopteran spectrum of the exemplary proteins of the present invention cf. VIP3A.

| Genus/species | Common name | TIC2160 | TIC2160 Del#8 | TIC3244 | Axmi335 (WO2013134523-0002) | VIP3A (VIP#a reference) |
|---|---|---|---|---|---|---|
| *Diatraea grandiosella* | Southwestern corn borer (SWC) | + | + | + | + | + (U.S. Pat. No. 6,107,279) |
| *Diatraea saccharalis* | Sugarcane borer (SCB) | + | nt | nt | + | + (U.S. Pat. No. 6,107,279) |
| *Helicoverpa zea* | Corn earworm (CEW) | + | − | nt | + | + (PNAS Vol.93 pp.5389-5394) |
| *Spodoptera frugiperda* | Fall armyworm (FAW) | + | − | + | + | + (PNAS Vol.93 pp.5389-5394) |
| *Trichoplusiani* | Cabbage looper (CLW) | + | nt | + | nt | + (U.S. Pat. No. 6,107,279) |
| *Ostrinia nubilalis* | European corn borer (ECB) | + | nt | + | + | − (PNAS Vol.93 pp.5389-5394) |
| *Chrysodeixis includens* | Soybean looper (SBL) | + | + | nt | + | nt |
| *Striacosta albicosta* | Western bean cutworm (WBC) | + | nt | nt | nt | nt |

TABLE 3-continued

Lepidopteran spectrum of the exemplary proteins of the present invention cf. VIP3A.

| Genus/species | Common name | TIC2160 | TIC2160 Del#8 | TIC3244 | Axmi335 (WO2013134523-0002) | VIP3A (VIP#a reference) |
|---|---|---|---|---|---|---|
| *Agrotis ipsilon* | Black cutworm (BCW) | − | − | nt | − | + (PNAS Vol.93 pp.5389-5394) |
| *Anticarsia gemmatalis* | Velvetbean caterpillar (VBC) | − | − | nt | nt | + (U.S. Pat. No. 6,107,279) |

Table description: Lepidopteran-activity spectrum for TIC2160, TIC2160_Del#8, TIC3244, Axmi335 and VIP3A reported as active (+), not active (−), and not-tested (nt). See Examples section for insect testing of TIC2160. See references for insect testing of VIP3A and WO2013134 for Axmi335.

Recombinant polynucleotide compositions that encode TIC2160 proteins are contemplated. For example, TIC2160 proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to the TIC2160 protein encoding sequences for expression of the protein in plants or a Bt-functional promoter operably linked to a TIC2160 protein encoding sequence for expression of the protein in a Bt bacterium or other *Bacillus* species. Other elements can be operably linked to the TIC2160 protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NOs:1, 3, 5, 6, 7, 8, 11, 18, 20, 22, 24, 26, 28, 30, 32, 34, 36, 38, 40, 42 or 43 that encodes the polypeptides or proteins having the amino acid sequence as set forth in SEQ ID NO: 2, 4, 9, 10, 12, 19, 21, 23, 25, 27, 29, 31, 33, 35, 37, 39, or 41. The codons of a recombinant polynucleotide molecule encoding for proteins disclosed herein can be substituted by synonymous codons (known in the art as a silent substitution).

A recombinant DNA construct comprising TIC2160 protein encoding sequences can further comprise a region of DNA that encodes for one or more insect inhibitory agents which can be configured to concomitantly express or co-express with a DNA sequence encoding a TIC2160 protein, a protein different from a TIC2160 protein, an insect inhibitory dsRNA molecule, or an ancillary protein. Ancillary proteins include, but are not limited to, co-factors, enzymes, binding-partners, or other agents that function synergistically to aid in the effectiveness of an insect inhibitory agent, for example, by aiding its expression, influencing its stability in plants, optimizing free energy for oligomerization, augmenting its toxicity, and increasing its spectrum of activity.

A recombinant DNA construct can be assembled so that all proteins or dsRNA molecules are expressed from one promoter or each protein or dsRNA molecules is under separate promoter control or some combination thereof. In one example, a plant multi-gene expression system can utilize multiply-linked expression cassettes, each cassette expressing a different protein or other agent such as one or more dsRNA molecules. Yet in another example, a plant multi-gene expression system can utilize multiply-unlinked expression cassettes each expressing a different protein or other agent such as one or more dsRNA molecules.

Recombinant polynucleotides or recombinant DNA constructs comprising a TIC2160 protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC2160 protein encoding sequence in a host cell, or subsequent expression of the encoded polypeptide. An exogenous recombinant polynucleotide or recombinant DNA construct that comprises a TIC2160 protein encoding sequence and that is introduced into a host cell is referred herein as a "transgene."

Transgenic bacteria, transgenic plant cells, transgenic plants, and transgenic plant parts that contain a recombinant polynucleotide that expresses any one or more of the TIC2160 protein encoding sequences are provided herein. The term "bacterial cell" or "bacterium" can include, but is not limited to, an *Agrobacterium, Rhizobium, Bacillus, Brevibacillus, Escherichia, Pseudomonas, Klebsiella*, and *Erwinia* wherein the *Bacillus* species can be a *Bacillus cereus* or a *Bacillus thuringiensis*, the *Brevibacillus* can be a *Brevibacillus laterosperous*, and the *Escherichia* can be an *Escherichia coli* cell. The term "plant cell" or "plant" can include but is not limited to a monocot, a dicot, an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that can not be induced to form a whole plant or that can not be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect or Lepidoptera-inhibitory amounts of a TIC2160 protein or variants of TIC2160 are provided. Such plants can be made by introducing a recombinant polynucleotide that encodes any of the TIC2160 proteins provided herein into a plant cell, and selecting a plant derived from the plant cell that expresses an insect or Lepidoptera-inhibitory amount of the TIC2160 proteins. Plants can be derived from the plant cells by regeneration, seed, pollen, or meristem transformation techniques. Methods for transforming plants are known in the art.

For expression in plant cells, any of the TIC2160 proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the choloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442, 1987) or the *Petunia hybrida* EPSPS CTP (CTP4) (See, della-Cioppa et al., *Proc. Natl. Acad. Sci. USA* 83:6873-6877, 1986) has been shown to target heterologous EPSPS protein sequences to chloroplasts in transgenic plants (See, U.S. Pat. Nos. 5,627,061; 5,633,435; and 5,312,910; and EP 0218571; EP 189707; EP 508909; and EP 924299). For targeting the TIC5290 protein to the chloroplast, a sequence encoding a chloroplast transit peptide is placed 5' in operable linkage and in frame to a synthetic coding sequence encoding the TIC5290 toxin protein that has been designed for optimal expression in plant cells.

TIC2160 protein-encoding sequences and sequences having a substantial percentage identity to TIC2160 protein-encoding sequences can be identified using methods known to those of ordinary skill in the art such as polymerase chain reaction (PCR) and hybridization. For example, the proteins of the TIC2160 protein toxin class can be used to produce antibodies that bind specifically to this class of proteins, and can be used to screen for and to find other members of the class.

Further, nucleotide sequences encoding the TIC2160 protein toxin class (and reverse complement sequences) can be used as probes and primers for screening to identify other members of the class using thermal-cycle or isothermal amplification and hybridization methods, e.g., oligonucleotides as set forth in SEQ ID NOs:13-17. Nucleotide sequence homologs, e.g., insecticidal proteins encoded by nucleotide sequences that hybridize to each or any of the sequences disclosed in this application under stringent hybridization conditions, are an embodiment of the present invention. The invention also provides a method for detecting a first nucleotide sequence that hybridizes to a second nucleotide sequence, wherein the first nucleotide sequence (or its reverse complement sequence) encodes an insecticidal protein or insecticidal fragment thereof and hybridizes under stringent hybridization conditions to the second nucleotide sequence. In such case, the second nucleotide sequence can be any of the nucleotide sequences disclosed in the TIC2160 protein toxin class under stringent hybridization conditions. Nucleotide coding sequences hybridize to one another under appropriate hybridization conditions and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS. One skilled in the art will recognize that, due to the redundancy of the genetic code, many other sequences are capable of encoding such related proteins, and those sequences, to the extent that they function to express insecticidal proteins either in Bt strains or in plant cells, are embodiments of the present invention, recognizing of course that many such redundant coding sequences will not hybridize under these conditions to the native Bt sequences encoding TIC2160. This application contemplates the use of these, and other identification methods known to those of ordinary skill in the art, to identify TIC2160 protein-encoding sequences and sequences having a substantial percentage identity to TIC2160 protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC2160 proteins to derive additional useful embodiments including assembly of segments of TIC2160 proteins with segments of diverse proteins different from TIC2160 and related proteins. The TIC2160 protein class may be subjected to alignment to each other and to other Bt pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity and/or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

Methods of controlling insects, in particular Lepidoptera infestations of crop plants, with proteins from the TIC2160 toxin protein class are also disclosed in this application. Such methods can comprise growing a plant comprising an insect- or Lepidoptera-inhibitory amount of a protein of the TIC2160 toxin protein class. In certain embodiments, such methods can further comprise any one or more of: (i) applying any composition comprising or encoding a protein of the TIC2160 protein toxin class to the plant or a seed that gives rise to the plant; and (ii) transforming the plant or a plant cell that gives rise to the plant with a polynucleotide encoding a protein of the TIC2160 protein toxin class. In general, it is contemplated that any protein in the TIC2160 protein toxin class can be provided in a composition, provided in a microorganism, or provided in a transgenic plant to confer insect inhibitory activity against Leptidopteran insects.

In certain embodiments, a recombinant polypeptide of the TIC2160 protein toxin class is the insecticidally active ingredient of an insect inhibitory composition prepared by culturing recombinant Bt cells under conditions to express and produce proteins of the TIC2160 protein toxin class. Such a composition can be prepared by desiccation, lyophilization, homogenization, extraction, filtration, centrifugation, sedimentation, or concentration of a culture of recombinant Bt cells expressing/producing said recombinant polypeptide. Such a process can result in a Bt cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the Lepidopteran pest species to provide a refuge for such unprotected plants. One particular example is described in U.S. Pat. No. 6,551,962, which is incorporated by reference in its entirety.

In one embodiment, to reduce the likelihood of resistance development, an insect inhibitory composition or transgenic plant comprising one or more proteins from the TIC2160 protein toxin class can further comprise at least one additional polypeptide that exhibits insect inhibitory activity against the same or other susceptible Lepidopteran insect species, but is different from the TIC2160 protein toxin. Possible additional polypeptides for such a composition include an insect inhibitory protein, an insect inhibitory dsRNA molecule, and an ancillary protein. One example for the use of such ribonucleotide sequences to control insect pests is described in U.S. Patent Publication 2006/0021087. Such additional polypeptide may be selected from the group consisting of a Lepidopteran insect inhibitory protein, such as, but not limited to, Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1Da, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, axmi209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), MT-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO: 2 and derivatives thereof as described in U.S. Patent Publication 2012-0167259 A1, SEQ ID NO: 2 and derivatives thereof as described in U.S. Patent Publication 2012-0047606 A1, SEQ ID NO: 2 and derivatives thereof as described in U.S. Patent Publication 2011-0154536 A1, SEQ ID NO: 2 and derivatives thereof as described in U.S. Patent Publication 2011-0112013 A1, SEQ ID NO: 2 and 4 and derivatives thereof as described in U.S. Patent Publication 2010-0192256 A1, SEQ ID NO: 2 and derivatives thereof as described in U.S. Patent Publication 2010-0077507 A1, SEQ ID NO: 2 and derivatives thereof as described in U.S. Patent Publication 2010-0077508 A1, SEQ ID NO: 2 and derivatives thereof as described in U.S. Patent Publication 2009-0313721 A1, SEQ ID NO: 2 or 4 and derivatives thereof as described in U.S. Patent Publication 2010-0269221 A1, SEQ ID NO: 2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO: 2 and derivatives thereof as described in U.S. Pat. No. 7,510,878(B2), SEQ ID NO: 2 and derivatives thereof as described in U.S. Pat. No. 7,812,129(B1); DIG-911 and DIG-180 as described in US Patent Publication No. 2015-0264940A1, and the like.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Coleopteran pests, combinations of insect inhibitory proteins of the present invention can be used with Coleopteran-active proteins such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), and $\overline{\omega}$-Hexatoxin-Hv1a (U.S. Patent Application Publication US2014-0366227 A1). For control of Hemipteran pests, combinations of insect inhibitory proteins of the present invention can be used with Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range, such as Lepidopteran or Hemipteran species or other plant pest species such as Coleopteran species that are not effectively controlled.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

EXAMPLES

In view of the foregoing, those of skill in the art should appreciate that changes can be made in the specific aspects which are disclosed and still obtain a like or similar result without departing from the spirit and scope of the invention. Thus, specific details disclosed herein are not to be interpreted as limiting. It should be understood that the entire disclosure of each reference cited herein is incorporated by reference in its entirety within the disclosure of this application.

Example 1: Discovery of Novel Bt Genes

This Example describes the discovery of the pesticidal proteins TIC2160 and TIC3244.

A sequence encoding a novel *Bacillus thuringiensis* (Bt) pesticidal protein was identified, cloned, sequence confirmed and tested in bioassay. The pesticidal protein TIC2160, presented herein as SEQ ID NOs: 1 (DNA) and 2 (protein), was isolated from the *Bacillus thuringiensis* strain EG8781. High throughput sequencing and bioinformatics were used to screen Bt genomes for genes (open reading frames) encoding proteins exhibiting similarity to TIC2160. A highly related gene, TIC3244, presented herein as SEQ ID NO: 3 (DNA) and SEQ ID NO: 4 (Protein) and derived from *Bacillus thuringiensis* (Bt) strain EG8639, was identified using this method. No proteins were identified in the prior art that exhibited insect toxic properties having any identity to these proteins greater than 94.6% with respect to the amino acid sequences as set forth in SEQ ID NO:2 and SEQ ID NO:4.

Example 2: Expression of Insect Inhibitory Proteins in Bacteria

This Example describes the characterization of a new class of Bt genes described in Example 1.

Nucleotide segments encoding this new class of Bt genes were made (a) by PCR amplification from corresponding genomic samples from which each open reading frame was identified in Example 1, (b) by molecular methods to introduce deletions, additions, and/or substitutions, and (c) by DNA synthesis to replace codons with synonymous codons. Nucleotide segments encoding this new class of Bt genes were also made by DNA synthesis to introduce deletions, additions, and/or substitutions.

Nucleotide segments set forth in SEQ ID NO: 1 (encodes TIC2160), SEQ ID NO: 8 (encodes TIC2160_De18), and SEQ ID NO: 3 (encodes TIC3244) were separately operably linked to a Bt sporulation stage promoter. A single clone for each construct was replicated in a Bt expression system. A population of Bt cells were harvested during the sporulation growth stage, and protein was extracted from cell lysate.

Nucleotide segments encoding an N-terminal HIS tag (SEQ ID NO: 44) fusion with TIC2160 (TIC2160_MGSSHHHHHHH, SEQ ID NO:12) and TIC2160_De18 (TIC2160_De18_MGSSHHHHHHH, SEQ ID NO:9) were separately operably linked to requisite *E. coli* expression elements. A single clone for each construct was replicated in an *E. coli* expression system. A population of *E. coli* cells were induced for recombinant protein expression, and protein was extracted and enriched for on HIS affinity columns.

The resulting bacterial transformants described in this Example were grown in culture media. Proteins from sample extractions were separated on denaturing gels. Western blots were performed to confirm the expression of the intended recombinant proteins having the deduced amino acid sequences as set forth in SEQ ID NO: 2 (TIC2160), SEQ ID NO: 8 (TIC2160_Del8), SEQ ID NO: 12 (TIC2160_MGSSHHHHHHH), SEQ ID NO: 9 (TIC2160_Del8_MGSSHHHHHHH), and SEQ ID NO: 4 (TIC3244). The bacterial transformants were observed to exhibit insect inhibitory properties to a variety of Lepidopteran pest species as described in Examples 3 and 4 below.

Example 3: Creation of TIC2160 Variants

Different strategies were employed to generate insecticidal toxin-variants disclosed in this application.

One exemplary strategy employed was to predict the secondary structure of the insecticidal protein of interest, e.g. TIC2160. Another exemplary strategy was to perform multiple sequence alignments of the insecticidal protein of interest, such as TIC2160, with close homologs to identify amino acid positions in the loop regions that might be important for receptor binding. Several amino acid variants were introduced into stretches of about eighty (80) amino acids of the N-terminal helical domain. Additional variants were designed with alternative sequences in loop regions in the putative C-terminal domain. These loop designs were generated such that subsequent combinations of loop designs are feasible.

Table 4 tabulates TIC2160 variants of the present invention with amino acid sequence changes compared to TIC2160_MGSSHHHHHHH (SEQ ID NO: 12). These variants contain an N-terminal His-tag (MGSSHHHHHHH) to facilitate protein purification and quantitation of TIC2160 and variants of TIC2160. A person skilled in the art will appreciate that the amino acid changes for individual variants shown in Table 4 can be combined to design other Lepidopteran active variants of the present invention. The nomenclature used to describe amino acid changes of the variants compared to TIC2160_MGSHHHHHH (SEQ ID NO: 12) is as follows: "i" is insertion, "d" is deletion, ":" means "through", and "_" means "and". For example, "d-Q12:14" means that residues 12 through 14 from TIC2160 MGSSHHHHHH are deleted in the variant. "i-D488EFCEH" means that the sequence "EFCEH" is inserted after D at position 488. "d-M1GSSHHHHHHH" for TIC2160 (SEQ ID NO: 2) means that GSSHHHHHHH is inserted after M at position 1 to produce TIC2160_MGSHHHHHH (SEQ ID NO: 12). Another example is "K273R_E274NN275E_V276T_T277V_E282Q". This variant (Variant-b-101) contains the following substitutions: K was substituted by R at position 273, N was substituted by N at position 274, N was substituted at position 275 by E, V was substituted by T at position 276, T was substituted by V at position 277, and E was substituted by Q at position 282.

The resulting variants were assayed for activity against the Lepidopteran insect pests Corn earworm (CEW, *Helicoverpa zea*), Fall armyworm (FAW, *Spodoptera frugiperda*), Soybean looper (SBL, *Chrysodeixis includens*), European corn borer (ECB, *Ostrinia nubilalis*), Southwestern corn borer (SWC, *Diatraea grandiosella*), Sugarcane borer (SCB, *Diatraea saccharalis*), Black cutworm (BCW, *Agrotis ipsilon*), Southern armyworm (SAW, *Spodoptera eridania*), Cabbage looper (CLW, *Trichoplusia ni*), and Velvetbean caterpillar (VBC, *Anticarsia gemmatalis*) in diet bioassays as described in Table 4 below.

TABLE 4

TIC2160 variants exhibiting Lepidopteran activity

| Bacterial Variant ID | Amino acid changes compared to TIC2160_MGSSHHHHHHH (SEQ ID NO: 12) | CEW | FAW | SBL | % ID to SEQ ID NO: 12 | ECB | SWC | SCB | BCW | SAW | CLW | VBC |
|---|---|---|---|---|---|---|---|---|---|---|---|---|
| TIC2160_MGSSHHHHHHH (SEQ ID NO: 12) | NA | ++ | + | ++ | NA | Y | Y | Y | N | N | Y | N |
| TIC2160_Del8 (SEQ ID NO: 10) | d-476:485_C486s_D488A | - | - | + | 98.6 | NT | Y | NT | N | NT | Y | NT |
| Variant-b-192 TIC2160_13 (SEQ ID NO: 23) | K419R_Q420E_K428R_D429N_E431D_K477E_E478K_K479R_S480T_C481S_E482D_E483Q_S485G_C486S_E487D_i-E489Q | ++ | + | ++ | 98 | Y | Y | Y | N | N | NT | N |
| Variant-b-139 TIC2160_15 (SEQ ID NO: 27) | K207R_N208P_P209G_K210A_S211K_Y212R_Q213R_N215P_V216G_T217S_K218R_E219Q_V220L_I221L_K273R_E274N_N275E_V276T_T277V_E282Q | ++ | ++ | ++ | 97.5 | Y | Y | Y | N | N | NT | N |
| Variant-b-101 TIC2160_16 (SEQ ID NO: 29) | K273R_E274N_N275E_V276T_T277V_E282Q | ++ | ++ | ++ | 99.3 | Y | Y | Y | N | N | NT | N |
| Variant-b-096 TIC2160_17 (SEQ ID NO: 31) | K207N_N208K_P209K_K210S_S211G_Q213E_D214N_N215D_J217S_K218R_E219Q | + | + | + |  | Y | Y | Y | N | N | NT | N |
| Variant-b-145 TIC2160_18 (SEQ ID NO: 33) | K207N_N208K_P209K_K210S_S211G_Q213E_D214N_N215D_T217S_K218R_E219Q_K273R_E274N_N275E_V276T_T277V_E282Q | +++ | +++ | ++ | 97.9 | Y | Y | Y | N | N | NT | N |

TABLE 4-continued

TIC2160 variants exhibiting Lepidopteran activity

| Bacterial Variant ID | Amino acid changes compared to TIC2160_MGSSHHHHHH (SEQ ID NO: 12) | CEW | FAW | SBL | % ID to SEQ ID NO: 12 | ECB | SWC | SCB | BCW | SAW | CLW | VBC |
|---|---|---|---|---|---|---|---|---|---|---|---|---|
| Variant-b-228 TIC2160_14 (SEQ ID NO: 25) | K207R_N208P_P209G_K210A_S211K_Y212R_ Q213R_N215P_V216G_T217S_K218R_ E219Q_V220L_I221L_E735N_N736Q_D737S_ S738D_T739S | + | + | + | 97.6 | NT | NT | NT | NT | NT | NT | NT |
| Variant-d-274 TIC2160_20 (SEQ ID NO: 35) | V276T | +++ | ++ | +++ | 99.9 | Y | Y | Y | N | N | NT | N |
| Variant-d-259 TIC2160_21 (SEQ ID NO: 37) | K265R_E269Q_E274N_N275E_V276T_T276V | +++ | ++ | +++ | 99.3 | Y | Y | Y | N | N | NT | N |
| Variant-c-287 TIC5420_13 (SEQ ID NO: 39) | d-Q12:14_I15M_N20T_N23D_V24T_G58S_ G78S_D86T_I131V_K145M_E206D_K207S_ N208R_P209G_K210R_E222N_N223E_N225T_ E226D_R261K_K265R_S268A_E269Q_E274N_ N275E_V276T_T277V_Q320K_I321T_H324Q_ I326L_N344S_S351T_K352R_N353Q_ R354K_E377Q_K419R_Q420E_K428R_D429N_ E431D_S465N_K477R_E478Q_K479E_ S480G_C481S_E482D_E483D_S485T_i- S485SRKRF_D488H_I492L_L547V_I561F_ T575F_A590E_I593V_V626A_K647N_V664A_ F671L_S677G_F696L_G717E_E735Q_K759N_ L762F_V766I_L771F_R773S_T778R_K781E_ E783D_T791S_N802S | +++ | ++ | ++ | 89.8 | Y | Y | Y | N | Y | NT | N |
| Variant-a-058 (SEQ ID NO: 19) | d- Q12:14_I15M_D86G_I131V_K145M_E206D K207S_N208R_P209G_K210R_E222N_N223E_ N225T_E226D_R261K_K265R_S268A_ E269Q_E274N_N275E_V276T_T277V_Q320K_ I321T_H324Q_I326L_N344S_E377Q_S465N_ D484E_i- D488EFCEH_I492L_L547V_I561F_T575F_ A590E_I593V_V626A_K647N_V664A_F671L_ S677G_F696L_G717E_E735Q_K759N_L762F_ V766I_L771F_R773S_T778R_K781E_E783D_ T791S_N802S | ++ | ++ | +++ | 92.3 | Y | Y | Y | N | Y | NT | N |
| Variant-a-145 (SEQ ID NO: 21) | d-Q12: 14_I15M_N20T_N23D_V24T_G58S_G78S_ D86T_I131V_K145M_E206D_K207S_N208R_ P209G_K210R_E222N_N223E_N225T_ E226D_R261K_K265R_S268A_E269Q_E274N_ N275E_V276T_T277V_Q320K_I321T_H324Q_ I326L_N344S_E377Q_S465N_D484E_i- D488EFCEH_I492L_L547V_I561F_T575F_ A590E_I593V_V626A_K647N_V664A_F671L_ S677G_F696L_G717E_E735Q_K759N_L762F_ V766I_L771F_R773S_T778R_K781E_E783D_ T791S_N802S | ++ | ++ | ++ | 92.3 | Y | Y | Y | N | Y | NT | N |
| TIC5420_a-b TIC5420_a (SEQ ID NO: 41) | d- Q12:14_I15M_D85G_I131V_K144M_P208S_ S210A_N224T_E225D_S267A_Q319M_I320T_ H323Q_I325L_N343S_E377Q_S464N_d- 475:485_C486S_D488A_I492L_L547V_ I561F_T575F_A590E_I593V_V625A_K646N_ V663A_F671L_S677G_F696L_G717E_E735Q_ K759N_L782F_V766I_L771F_R773S_T778R_ K781E_E783D_T791S_N8025 | - | + | NT | 94.6 | NT | NT | NT | NT | NT | NT | NT |

-: no activity;
+: activity against insect pest;
++: strong activity against insect pest;
+++: no survivors in diet bioassay;
NT: not tested;
NA: not applicable;
Y: activity observed;
N: no activity observed;
% ID describes the percent of sequence identity of the respective variants when aligned with TIC2160_MGSSHHHHHH using alignment tools such as ClustAl W.

Example 4: TIC2160 and TIC2160 Variants Demonstrate Activity Against Lepidopteran Insect Pests This Example illustrates diet bioassay toxicity of exemplary proteins TIC2160 (SEQ ID NO: 2), TIC3244 (SEQ ID NO: 4), TIC2160_MGSSHHHHHHH (SEQ ID NO: 12), TIC2160_De18_MGSSHHHHHHH (SEQ ID NO: 9), and the TIC2160 variants listed in Table 4 of Example 3 above. The respective Bt and E. coli samples were prepared as described in Example 2 and were provided in an insect diet and used in diet bioassays against the Lepidopteran insect pests Corn earworm (CEW, Helicoverpa zea), Fall armyworm (FAW, Spodoptera frugiperda), Soybean looper (SBL, Chrysodeixis includens), European corn borer (ECB, Ostrinia nubilalis), Southwestern corn borer (SWC, Diatraea grandiosella), Sugarcane borer (SCB, Diatraea saccharalis), Black cutworm (BCW, Agrotis ipsilon), Southern armyworm (SAW, Spodoptera eridania), Cabbage looper (CLW, Trichoplusia ni), and Velvetbean caterpillar (VBC, Anticarsia gemmatalis).

Protocols for bioassays and scoring insects for mortality and stunting are known in the art, examples of which are described in PCT Patent Application Publication No. WO 2012/139004 and in U.S. Pat. No. 7,927,598.

Table 3 located in the detailed description of the invention correlates the exemplary proteins TIC2160, TIC2160_De18, and TIC3244 to pesticidal activity by insect species in diet bioassay and compares the activity of these exemplary proteins with Axmi335 and VIP3A.

Table 4 compares the activity of variants against FAW, SL and CEW and other Lepidopteran pests to TIC2160_MGSSHHHHHHH (SEQ ID NO: 12). Some of the variants of TIC2160 demonstrated improved activity relative to TIC2160, such as, Variant-b-139 and Variant-b-101, which showed improved FAW activity. Other variants of TIC2160 demonstrated a reduced efficacy against specific Lepidoptera, such as, TIC2160_De18 which lost activity against FAW and CEW and TIC5420_a which demonstrated lost activity for CEW.

TIC2160 and variants of TIC2160 were also assayed against European corn borer, Southwestern corn borer, Sugarcane borer, Black cutworm, Southern armyworm, and Velvetbean caterpillar demonstrating activity against many of these insect pest species.

It is concluded that TIC2160, TIC2160MGSSHHHHHHH, TIC2160De18MGSSHHHHHHH, TIC3244 and the TIC2160 variants are active against Lepidopteran pests.

Example 5: Design of Synthetic Coding Sequences Encoding TIC2160 and Variants of TIC2160 for Expression in Plant Cells Synthetic coding sequences were constructed for use in expression of the encoded protein in plants, cloned into a binary plant transformation vectors, and used to transform plant cells. The synthetic sequences were synthesized according to methods generally described in U.S. Pat. No. 5,500,365, avoiding certain inimical problem sequences such as ATTTA and A/T rich plant polyadenylation sequences while preserving the amino acid sequence of the original protein. The synthetic coding sequences encode TIC2160 and variants of TIC2160 comprising amino acid substitutions, deletions and insertions as described in Example 4 above. In some instances the synthetic coding sequences for TIC2160 and the TIC2160 variants were also designed to be targeted to the chloroplast by operably linking 5' to the TIC2160 or TIC2160 variant coding sequence a sequence encoding a chloroplast targeting signal. Table 5 below shows the description of each of the TIC2160 variants along with the corresponding SEQ ID NOs for the synthetic coding sequence and the encoded amino acid sequence. The column "Corresponding Bacterial Variant from Table 4" shows the relationship between the plant variant designation and the assayed bacterial TIC2160 variant wherein the amino acid substitutions, deletions, and insertions in the plant variant correspond to the same substitutions, deletions, and insertions in the corresponding bacterial variant.

TABLE 5

TIC2160 and TIC2160 variant synthetic coding sequences.

| Plant Variant Description | Corresponding Bacterial Variant from Table 4 | Synthetic Plant DNA SEQ ID NO: | Protein SEQ ID NO: |
|---|---|---|---|
| TIC2160_Del8 | TIC2160_Del8 | 11 | 10 |
| TIC2160_13 | Variant-b-192 | 22 | 23 |
| TIC2160_14 | Variant-b-228 | 24 | 25 |
| TIC2160_15 | Variant-b-139 | 26 | 27 |
| TIC2160_16 | Variant-b-101 | 28 | 29 |
| TIC2160_17 | Variant-b-096 | 30 | 31 |
| TIC2160_18 | Variant-b-145 | 32 | 33 |
| TIC2160_20 | Variant-d-274 | 34 | 35 |
| TIC2160_21 | Variant-d-259 | 36 | 37 |
| TIC5420_13 | Variant-c-287 | 38 | 39 |
| TIC5420_a | TIC5420_a-b | 40 | 41 |

The TIC2160 variant synthetic coding sequences presented in Table 5 above were used in binary plant transformation vectors to generate transgenic plants expressing the TIC22160 variant toxin proteins and assayed for activity against Lepidopteran insect pests.

Example 6: Assay of Activity of TIC2160 and TIC2160 Variants in Stably Transformed Corn Plants Against Lepidopteran Insect Pests This Example illustrates the Lepidopteran-inhibitory activity of TIC2160 and TIC2160 variants against various Lepidopteran insect pests when expressed in stably transformed corn plants.

Binary plant transformation vectors comprising transgene cassettes designed to express both plastid targeted and untargeted TIC2160 and variants of TIC2160 pesticidal proteins (TIC2160_De18, TIC5420_a, and TIC2160_18) were cloned using methods known in the art. The resulting vectors were used to stably transform corn plants. Tissues were harvested from the transformants and used in insect bioassay against various Lepidopteran insect pests.

The resulting plant transformation vectors comprised a first transgene cassette for expression of the TIC2160 and variants of TIC2160 pesticidal proteins which comprised a plant expressible promoter, operably linked 5' to a leader, operably linked 5' to an intron, operably linked 5' to a synthetic coding sequence encoding a plastid targeted or untargeted TIC2160 or TIC2160 variant protein, which was in turn operably linked 5' to a 3' UTR; and a second transgene cassette for the selection of transformed plant cells using glyphosate selection. The synthetic coding sequence encoding the TIC2160 protein is presented as SEQ ID NO: 6 and encodes the protein presented herein as SEQ ID NO:

2. The synthetic coding sequence encoding the TIC2160 variant TIC2160_De18 is presented as SEQ ID NO: 11 and encodes the protein presented as SEQ ID NO: 10. The synthetic coding sequence encoding the TIC2160 variant TIC5420_a is presented as SEQ ID NO: 40 and encodes the protein presented as SEQ ID NO: 41. The synthetic coding sequence encoding TIC2160_18 is presented as SEQ ID NO: 32 and encodes the protein presented as SEQ ID NO: 33.

Corn variety LH244 was transformed with the binary transformation vectors described above using an *Agrobacterium*-mediated transformation method. The transformed cells were induced to form plants by methods known in the art. Bioassays using plant leaf disks were performed analogous to those described in U.S. Pat. No. 8,344,207. A non-transformed LH244 plant was used to obtain tissue to be used as a negative control. Multiple $R_0$ transformation events from each binary vector were assessed against Corn earworm (CEW, *Helicoverpa zea*), Fall armyworm (FAW, *Spodoptera frugiperda*), Southwestern Corn Borer (SWC, *Diatraea grandiosella*), and Black cutworm (BCW, *Agrotis ipsilon*). For some selected events, $F_1$ leaf, ears, and stalk were assessed for damage using a rating scale. Events expressing TIC2160 were also assessed in field trials. Table 6 below shows the activity of TIC2160 and the variants of TIC2160 against Lepidpoteran insect pests wherein "+" indicates activity, "−" indicates no activity observed, and "NT" indicates testing was not performed or data is still pending against the insect and tissue.

Binary plant transformation vectors comprising transgene cassettes designed to express both plastid targeted and untargeted TIC2160 and variants of TIC2160 pesticidal proteins (TIC2160_De18, TIC5420_a, TIC2160_13, TIC2160_14, TIC2160_15, TIC2160_16, TIC2160_17, and TIC2160_18) were cloned using methods known in the art. The resulting vectors were used to stably transform soybean plants. Tissues were harvested from the transformants and used in insect bioassay against various Lepidop TABLE 7-continued Assay of activity TIC2160 and TIC2160 variants against Leptidopteran insect pests in stably transformed soybean plants.

| Toxin | SEQ ID NO: | SPW $R_0$ Leaf | SPW $R_1$ Leaf | SAW $R_0$ Leaf | SAW $R_1$ Leaf | SBL $R_0$ Leaf | SBL $R_1$ Leaf | VBC $R_0$ Leaf | VBC $R_1$ Leaf |
|---|---|---|---|---|---|---|---|---|---|
| TIC5420_a | 41 | + | NT | − | NT | + | NT | NT | NT |
| TIC2160_13 | 23 | + | NT | + | NT | + | NT | NT | NT |
| TIC2160_14 | 25 | − | NT | − | NT | − | NT | NT | NT |
| TIC2160_15 | 27 | + | NT | + | NT | − | NT | NT | NT |
| TIC2160_16 | 29 | + | NT | + | NT | + | NT | NT | NT |
| TIC2160_17 | 31 | − | NT | − | NT | − | NT | NT | NT |
| TIC2160_18 | 33 | + | NT | + | NT | − | NT | NT | NT |

As can be seen in Table 7 above, the TIC2160 pesticidal protein and TIC2160 variants TIC2160_De18, TIC5420_a, TIC2160_13, TIC2160_15, and TIC2160_18 demonstrated activity against Lepidopteran insect pests in stably transformed soybean plants.

Transgenic events expressing TIC2160 were also grown in screen house trials in the United States and infested with SAW, SBL, and SPW. Resistance was defined as being less than or equal to fifteen percent defoliation in the soybean plants. Plants expressing TIC2160 demonstrated resistance against SL and SPW in these trials based upon this criteria.

Example 8: Assay of Activity of TIC2160 and TIC2160 Variants in Stably Transformed Cotton Plants Against Lepidopteran Insect Pests This Example illustrates the Lepidopteran-inhibitory activity of TIC2160 and the TIC2160 variant, TIC2160_18 against various Lepidopteran insect pests when expressed in stably transformed cotton plants.

Binary plant transformation vectors comprising transgene cassettes designed to express both plastid targeted and untargeted TIC2160 and TIC2160_18 pesticidal proteins were cloned using methods known in the art. The resulting vectors were used to stably transform cotton plants. Tissues were harvested from the transformants and used in insect bioassay against various Lepidopteran insect pests.

The resulting plant transformation vectors were as described in example 7 above where spectinomycin selection was used to select for transformed cotton cells.

TIC2160 (SEQ ID NO: 2 and encoded by SEQ ID NO: 6) and the TIC2160 variant, TIC2160_18 encoded by the sequence as presented in Table 5 above were cloned into binary plant transformation vectors and used to transform cotton plant cells using an *Agrobacterium*-mediated transformation method. The transformed cells were induced to form plants by methods known in the art. Bioassays using plant tissues were performed in a similar manner as described above against the Lepidopteran insect pests Cotton bollworm (CBW, *Helicoverpa zea*), Fall armyworm (FAW, *Spodoptera frugiperda*), Soybean looper (SBL, *Chrysodeixis includens*), and Tobacco budworm (TBW, *Heliothis virescens*). For TIC2160, the tissues used in bioassay were $R_0$ leaf, $R_1$ leaf, $R_1$ squares and $R_1$ bolls. For TIC2160_18 $R_0$ leaf tissues were used in bioassay. Tables 8 and 9 below show the activity observed for TIC2160 and TIC2160_18 in bioassay against the Lepidopteran insect pests wherein "+" indicates activity, "−" indicates no activity observed, and "NT" indicates testing was not performed against the insect.

TABLE 8

Assay of activity TIC2160 and TIC2160_18 against Lepidopteran insect pests in stably transformed cotton plants.

| Toxin | SEQ ID NO: | CBW $R_0$ Leaf | CBW $R_1$ Leaf | CBW $R_1$ Boll | FAW $R_0$ Leaf | FAW $R_1$ Leaf |
|---|---|---|---|---|---|---|
| TIC2160 | 2 | + | + | + | + | + |
| TIC2160_18 | 33 | + | NT | NT | NT | NT |

TABLE 9

Assay of activity TIC2160 and TIC2160_18 against Lepidopteran insect pests in stably transformed cotton plants.

| Toxin | SEQ ID NO: | SBL $R_0$ Leaf | SBL $R_1$ Leaf | TBW $R_0$ Leaf | TBW $R_1$ Leaf |
|---|---|---|---|---|---|
| TIC2160 | 2 | + | + | + | + |
| TIC2160_18 | 33 | + | NT | NT | NT |

As can be seen in Tables 8 and 9 above, the TIC2160 and TIC2160_18 pesticidal proteins demonstrated activity against Lepidopteran insect pests in stably transformed cotton plants.

Example 9: Assay of Activity of TIC2160 and TIC2160 Variants in Stably Transformed Sugarcane Plants Against Sugarcane Borer This Example illustrates the Lepidopteran-inhibitory activity of TIC2160 against the Lepidopteran insect pest, Sugarcane borer when expressed in stably transformed sugarcane plants.

A binary plant transformation vector comprising a transgene cassette designed to express untargeted TIC2160 pesticidal protein was cloned using methods known in the art. The resulting vector as described in Example 6 above was used to stably transform sugarcane plants. The transformed plants were assayed for copy number of the inserted transgene cassette. Transgenic sugarcane plants comprising one or two insertions of the transgene cassette driving TIC2160 expression were infested with the Lepidopteran insect pest, Sugarcane borer (*Diatraea saccharalis*). Leaf damage ratings were assayed after infestation and were compared to non-transgenic controls. Of the seventeen sugarcane events possessing one or two copies of the transgene cassette, ten events demonstrated resistance. Four events of the eight single copy events demonstrated resistance. The transgenic sugarcane plants expressing TIC2160 demonstrated resistance to Sugarcane borers.

Example 10: Assay of Activity of TIC5420_13 in Stably Transformed Cotton Against Lepidopteran Insect Pests This Example describes assaying the TIC2160 variant, TIC5420_13 for Lepidopteran-inhibitory activity in stably transformed cotton.

Binary plant transformation vectors comprising transgene cassettes designed to express both plastid targeted and untargeted TIC5420_13 pesticidal protein are cloned using methods known in the art. The resulting vectors were used to stably transform cotton plants. Tissues are harvested from the transformants and used in insect bioassay against various Lepidopteran insect pests.

The resulting plant transformation vectors are as described in Example 7 above where spectinomycin selection is used to select for transformed cotton cells.

TIC5420_13 (SEQ ID NO: 39 and encoded by SEQ ID NO: 38) are cloned into binary plant transformation vectors and used to transform cotton plant cells using an *Agrobacterium*-mediated transformation method. The transformed cells are induced to form plants by methods known in the art. Bioassays using plant tissues are performed in a similar manner as described above against the Lepidopteran insect pests Cotton bollworm (CBW, *Helicoverpa zea*), Fall armyworm (FAW, *Spodoptera frugiperda*), Soybean looper (SBL, *Chrysodeixis includens*), and Tobacco budworm (TBW, *Heliothis virescens*). Tissues such as $R_0$ leaf, $R_0$ squares, $R_0$ bolls, $R_1$ leaf, $R_1$ squares and $R_1$ bolls are used in bioassay to determine the activity of TIC5420_13 against the Lepidopteran insect pest species.

Example 11: Assay of Activity of TIC2160 and TIC2160 Variants in Stably Transformed Plants Against Lepidopteran Insect Pests This Example describes assaying TIC2160 or variants of TIC2160 for Lepidopteran-inhibitory activity in stably transformed plants such as corn, soybean, cotton, and sugarcane; as well as other monocot and dicot species.

The synthetic coding sequences encoding TIC2160 or variants of TIC2160 such as those presented in Table 5 of example 5 above, or other synthetic coding sequences encoding new variants of TIC2160 used for expression in transformed plant cells are cloned into binary plant transformation vectors as previously described in examples 6 and 7 above. The binary plant transformation vectors can comprise plastid targeted or untargeted TIC2160 or TIC2160 variant coding sequences. The binary plant transformation vectors are used to transform plant cells derived from corn, soybean, cotton, or sugarcane; or other plant cells derived from other monocot or dicot plant species. The transformed cells are induced to form whole plants.

Tissues such as leaf, flower, pod, kernel, seed, square, boll, or other plant tissue susceptible to Lepidopteran damage can be used in bioassay to determine the Lepidopteran-inhibitory property of the TIC2160 variant. Such Lepitdopteran insect pests used in bioassay can include species such as Corn Earworm (CEW, also known as Soybean podworm, and Cotton bollworm, *Helicoverpa zea*), Fall Armyworm (FAW, *Spodoptera frugiperda*), Soybean Looper (SBL, *Chrysodeixis includens*), European Corn Borer (ECB, *Ostrinia nubilalis*), Southwestern Corn Borer (SWC, *Diatraea grandiosella*), Sugarcane Borer (SCB, *Diatraea saccharalis*), Black cutworm (BCW, *Agrotis ipsilon*), Southern armyworm (SAW, *Spodoptera eridania*), Cabbage looper (CLW, *Trichoplusia ni*), Tobacco budworm (TBW, *Heliothis virescens*), and Velvetbean caterpillar (VBC, *Anticarsia gemmatalis*); or other Lepidopteran pests which feed on the particular plant species.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide segment encoding a pesticidal protein wherein
said pesticidal protein comprises an amino acid sequence having at least 95% amino acid sequence identity to SEQ ID NO: 39,
wherein said protein exhibits activity against an insect species of the order Lepidoptera.

2. A plant cell comprising the recombinant nucleic acid molecule of claim 1, wherein said recombinant nucleic acid molecule is expressed to produce a pesticidally effective amount of the pesticidal protein.

3. A host cell comprising the recombinant nucleic acid molecule of claim 1, wherein said host cell is selected from the group consisting of a bacterial cell and a plant cell.

4. The bacterial host cell of claim 3, wherein said bacterial host cell is from a genus of bacteria selected from the group consisting of: *Agrobacterium, Rhizobium, Bacillus, Brevibacillus, Escherichia, Pseudomonas, Klebsiella,* and *Erwinia.*

5. The plant host cell of claim 3, wherein said plant host cell is a dicotyledonous plant cell or a monocotyledonous plant cell.

6. The plant host cell of claim 3, wherein said plant host cell is selected from the group consisting of an alfalfa, banana, barley, bean, broccoli, cabbage, carrot, cassava, castor, cauliflower, celery, chickpea, Chinese cabbage, coconut, coffee, corn, clover, cotton, cucumber, Douglas fir, eggplant, *eucalyptus*, flax, garlic, grape, hops, leek, lettuce, Loblolly pine, millets, melons, nut, oat, olive, onion, palm, pasture grass, pea, peanut, pepper, pigeon pea, potato, poplar, pumpkin, *Radiata* pine, radish, rapeseed, rice, rye, safflower, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

7. A plant comprising a recombinant nucleic acid molecule comprising a heterologous promoter operably linked to a polynucleotide segment encoding a pesticidal protein, wherein:
a) said pesticidal protein comprises an amino acid sequence having at least 95% amino acid sequence identity to SEQ ID NO: 39,
wherein said protein exhibits activity against an insect species of the order Lepidoptera.

8. The plant of claim 7, wherein said plant is a monocotyledonous plant or a dicotyledonous plant.

9. The plant of claim 7, wherein the plant is selected from the group consisting of an alfalfa, banana, barley, bean, broccoli, cabbage, carrot, cassava, castor, cauliflower, celery, chickpea, Chinese cabbage, coconut, coffee, corn, clover, cotton, cucumber, Douglas fir, eggplant, *eucalyptus*, flax, garlic, grape, hops, leek, lettuce, Loblolly pine, millets, melons, nut, oat, olive, onion, palm, pasture grass, pea, peanut, pepper, pigeon pea, potato, poplar, pumpkin, *Radiata* pine, radish, rapeseed, rice, rye, safflower, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

10. A seed from the plant of claim 7, wherein said seed comprises said recombinant nucleic acid molecule.

11. An insect inhibitory composition comprising the pesticidal protein of claim 1.

12. The insect inhibitory composition of claim 11, further comprising a nucleotide sequence encoding at least one other pesticidal agent that is different from said pesticidal protein.

13. The insect inhibitory composition of claim 12, wherein said at least one other pesticidal agent is selected from the group consisting of an insect inhibitory protein, an insect inhibitory dsRNA molecule, and an ancillary protein.

14. The insect inhibitory composition of claim 13, wherein said at least one other pesticidal agent exhibits activity against one or more pest species of the orders Lepidoptera, Coleoptera, Hemiptera, Homoptera, or Thysanoptera.

15. The insect inhibitory composition of claim 14, wherein said at least one other pesticidal protein is selected from the group consisting of a Cry1A, Cry1Ab, Cry1Ac, Cry1A.105, Cry1Ae, Cry1B, Cry1C, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC3131, VIP3A, VIP3B, VIP3Ab, AXMI-001, AXMI-002, AXMI-030, AXMI-035, AXMI-036, AXMI- 045, Axmi52, Axmi58, Axmi88, Axmi97, Axmi102, Axmi112, Axmi117, Axmi100, AXMI-115, AXMI-113, AXMI-005, AXMI134, AXMI-150, Axmi171, AXMI-184, axmi196, axmi204, axmi207, axmi209, Axmi205, AXMI218, AXMI220, AXMI221z, AXMI222z, AXMI223z, AXMI224z, AXMI225z, AXMI238, AXMI270, AXMI279, AXMI345, AXMI-R1, IP3, DIG-3, DIG-5, DIG-10, and a DIG-11.

16. A commodity product produced from the host cell of claim 3, said commodity product comprising a detectable amount of said recombinant nucleic acid molecule or said pesticidal protein.

17. The commodity product of claim 16, selected from the group consisting of flakes, cakes, flour, meal, syrup, oil, silage, starch, cereal, juices, concentrates, jams, jellies, marmalades, whole seed, processed seed, lint, fiber, paper, biomass, fuel products, pellets protein, bran, milk, cheese, wine, animal feed, and cream; wherein said commodity product is produced from a host cell derived from a plant selected from the group consisting of soybean, rice, wheat, sorghum, pigeon pea, peanut, and melon.

18. A method of producing seed comprising the recombinant nucleic acid molecule of claim 1, said method comprising:
   a) planting at least one seed comprising said recombinant nucleic acid molecule of claim 1;
   b) growing a plant from said at least one seed; and
   c) harvesting seeds from said plant, wherein said harvested seeds comprise said recombinant nucleic acid molecule of claim 1.

19. A method for controlling a Lepidopteran species pest, said method comprising contacting said pest with an insecticidally effective amount of at least one pesticidal protein comprising an amino acid sequence having at least 95% amino acid sequence identity to SEQ ID NO: 39,
   wherein said protein exhibits activity against an insect species of the order Lepidoptera.

* * * * *